United States Patent [19]

Valenzuela et al.

[11] Patent Number: 5,851,797
[45] Date of Patent: Dec. 22, 1998

[54] TIE LIGAND-3, METHODS OF MAKING AND USES THEREOF

[75] Inventors: David M. Valenzuela, Franklin Square, N.Y.; Pamela F. Jones, Fairfield, Conn.; George D. Yancopoulos, Yorktown Heights, N.Y.

[73] Assignee: Regeneron Pharmaceuticals, Inc., Tarrytown, N.Y.

[21] Appl. No.: 665,926

[22] Filed: Jun. 19, 1996

[51] Int. Cl.$^6$ .......................... C07K 14/475; C12N 5/10; C12N 5/12; C12N 15/64
[52] U.S. Cl. .................. 435/69.1; 536/23.5; 530/350; 530/402; 435/320.1; 435/325; 435/348; 435/252.3; 435/254.11; 424/1.69; 424/178.1
[58] Field of Search .................... 435/69.1, 320.1, 435/91.1, 325, 252.3, 254.11, 348; 530/350, 402, 866, 387.1; 424/1.69, 178.1; 514/12; 536/23.5

[56] References Cited

U.S. PATENT DOCUMENTS

| 5,447,860 | 9/1995 | Ziegler ................................. 435/240.1 |
| 5,521,073 | 5/1996 | Davis et al. ............................ 435/69.5 |
| 5,643,755 | 7/1997 | Davis et al. ............................ 435/69.5 |
| 5,650,490 | 7/1997 | Davis et al. ............................ 530/350 |

FOREIGN PATENT DOCUMENTS

| WO 94/11499 | 5/1994 | WIPO . |
| WO 95/13387 | 5/1995 | WIPO . |
| 95/21866 | 8/1995 | WIPO . |
| 95/26364 | 10/1995 | WIPO . |
| 96/11269 | 4/1996 | WIPO . |

OTHER PUBLICATIONS

Oncogene, vol. 9, No. 11, issued Nov. 1994, Fletcher et al "LERK-2, a binding protein for the receptor-tyrosine kinase ELK, is evolutionarily conserved and expressed in a developmentally regulated pattern", pp. 3241–3247.

Oncogene, vol. 10, No. 2, issued Jan. 1995, Kozlosky et al., "Ligands for the receptor tyrosine kinases hek and elk: isolation of cDNAs encoding a family of proteins", pp. 299–306.

Oncogene, vol. 8, No. 6, Jun. 1993, P.C. Maisonpierre, et al., "Distinct rat genes with related profiles of expression define a TIE receptor tyrosine kinase family", pp. 1631–1637.

The Embo Journal, vol. 13, No. 16, issued 1994, Beckmann et al., "Molecular characterization of a family of ligands for eph-related tyrosine kinase receptors", pp. 3757–3762.

Nature, vol. 368, issued Apr. 7, 1994, Bartley et al., "B61 is a ligand for the ECK receptor protein-tyrosine kinase", pp. 558–560.

Nature, vol. 347, issued Oct. 25, 1990, Cattaneo et al., "Proliferation and differentiation of neuronal stem cells regulated by nerve growth factor", pp. 762–765.

Biochemistry, vol. 29, 1990, Derynck, et al., "Recombinant Expression, Biochemical Characterization, and Biological Activities of the Human MGSA/gro Protein" pp. 10225–10233.

Proc. Natl. Acad. Sci. USA, vol. 77, No. 12, 1980, Weissenbach, et al., Two interferon mRNAs in human fibroblasts: In vitro translation and *Escherichia coli* cloning studies, pp. 7152–7156.

Proc. Natl. Acad. Sci. USA, vol. 87, 1990, Partanen, et al., "Putative tyrosine kinases expressed in K-562 human leukemia cells", pp. 8913–8917.

Molecular and Cellular Biology, vol. 12, No. 4,, 1992, Partanen, et al., "A Novel Endothelial Cell Surface Receptor Tyrosine Kinase with Extracellular Epidermal Growth Factor Homology Domains", pp. 1698–1707.

Sato et al., Distinct roles of the receptor tyrosine kinases Tie-1 and Tie-2 in blood vessels formation, Nature, 376(6535): 70–74, Jul. 6, 1995.

Sato et al., tie-1 and tie-2 define antoher class of putative recepotr tyrosine kinase genes expressed in early embryonic vascular system, Proc. Natl. Acad. Sci. USA, 90:9355–9358, Oct. 1993.

Dumont et al., Dominant-negative and targeted null mutations in the endothelial recptor tyrosine kinase, tek, reveal, a critical role in vasculogenesis of the embryo, Genes Dev., 8:1897–1909, Aug. 1994.

*Primary Examiner*—Lorraine M. Spector
*Assistant Examiner*—Claire M. Kaufman
*Attorney, Agent, or Firm*—Robert J. Cobert

[57] ABSTRACT

The present invention provides for an isolated nucleic acid molecule encoding TIE ligand-3. In addition, the invention provides for a receptorbody which specifically binds TIE ligand-3. The invention also provides an antibody which specifically binds TIE ligand-3. The invention further provides for an antagonist of TIE. The invention also provides for therapeutic compositions as well as a method of blocking blood vessel growth, a method of promoting neovascularization, a method of promoting the growth or differentiation of a cell expressing the TIE receptor, a method of blocking the growth or differentiation of a cell expressing the TIE receptor and a method of attenuating or preventing tumor growth in a human.

15 Claims, 23 Drawing Sheets

Fig. 4A.

```
              10        20        30        40        50        60        70        80
               •         •         •         •         •         •         •         •
          CAGCTGACTCAGGCAGGCTCCATGCTGAACGGTCACACAGAGAGGAAACAATAAATCTCAGCTACTATGCAATAAATATC 90       100       110       120       130       140       150       160
               •         •         •         •         •         •         •         •
          TCAAGTTTTAACGAAGAAAAACATCATTGCAGTGAAATAAAAAATTTTAAAATTTTAGAACAAAGCTAACAAATGGCTAG 170       180       190       200       210       220       230       240
               •         •         •         •         •         •         •         •
          TTTTCTATGATTCTTCTTCAAACGCTTTCTTTGAGGGGGAAAGAGTCAAACAAACAAGCAGTTTTACCTGAAATAAAGAA 250       260       270       280       290       300       310
               •         •         •         •         •         •         •
          CTAGTTTTAGAGGTCAGAAGAAAGGAGCAAGTTTTGCGAGAGGCACGGAAGGAGTGTGCTGGCAGTACA ATG ACA
                                                                              M   T>

320       330       340       350       360       370
               •         •         •         •         •         •
          GTT TTC CTT TCC TTT GCT TTC CTC GCT GCC ATT CTG ACT CAC ATA GGG TGC AGC AAT CAG
           V   F   L   S   F   A   F   L   A   A   I   L   T   H   I   G   C   S   N   Q>

380       390       400       410       420       430
               •         •         •         •         •         •
          CGC CGA AGT CCA GAA AAC AGT GGG AGA AGA TAT AAC CGG ATT CAA CAT GGG CAA TGT GCC
           R   R   S   P   E   N   S   G   R   R   Y   N   R   I   Q   H   G   Q   C   A>

440       450       460       470       480       490
               •         •         •         •         •         •
          TAC ACT TTC ATT CTT CCA GAA CAC GAT GGC AAC TGT CGT GAG AGT ACG ACA GAC CAG TAC
           Y   T   F   I   L   P   E   H   D   G   N   C   R   E   S   T   T   D   Q   Y>

500       510       520       530       540       550
               •         •         •         •         •         •
          AAC ACA AAC GCT CTG CAG AGA GAT GCT CCA CAC GTG GAA CCG GAT TTC TCT TCC CAG AAA
           N   T   N   A   L   Q   R   D   A   P   H   V   E   P   D   F   S   S   Q   K>

560       570       580       590       600       610
               •         •         •         •         •         •
          CTT CAA CAT CTG GAA CAT GTG ATG GAA AAT TAT ACT CAG TGG CTG CAA AAA CTT GAG AAT
           L   Q   H   L   E   H   V   M   E   N   Y   T   Q   W   L   Q   K   L   E   N>

620       630       640       650       660       670
               •         •         •         •         •         •
          TAC ATT GTG GAA AAC ATG AAG TCG GAG ATG GCC CAG ATA CAG CAG AAT GCA GTT CAG AAC
           Y   I   V   E   N   M   K   S   E   M   A   Q   I   Q   Q   N   A   V   Q   N>

680       690       700       710       720       730
               •         •         •         •         •         •
          CAC ACG GCT ACC ATG CTG GAG ATA GGA ACC AGC CTC CTC TCT CAG ACT GCA GAG CAG ACC
           H   T   A   T   M   L   E   I   G   T   S   L   L   S   Q   T   A   E   Q   T>

740       750       760       770       780       790
               •         •         •         •         •         •
          AGA AAG CTG ACA GAT GTT GAG ACC CAG GTA CTA AAT CAA ACT TCT CGA CTT GAG ATA CAG
           R   K   L   T   D   V   E   T   Q   V   L   N   Q   T   S   R   L   E   I   Q>

800       810       820       830       840       850
               •         •         •         •         •         •
          CTG CTG GAG AAT TCA TTA TCC ACC TAC AAG CTA GAG AAG CAA CTT CTT CAA CAG ACA AAT
           L   L   E   N   S   L   S   T   Y   K   L   E   K   Q   L   L   Q   Q   T   N>

860       870       880       890       900       910
               •         •         •         •         •         •
          GAA ATC TTG AAG ATC CAT GAA AAA AAC AGT TTA TTA GAA CAT AAA ATC TTA GAA ATG GAA
           E   I   L   K   I   H   E   K   N   S   L   L   E   H   K   I   L   E   M   E>

920       930       940       950       960       970
               •         •         •         •         •         •
          GGA AAA CAC AAG GAA GAG TTG GAC ACC TTA AAG GAA GAG AAA GAG AAC CTT CAA GGC TTG
           G   K   H   K   E   E   L   D   T   L   K   E   E   K   E   N   L   Q   G   L>

980       990      1000      1010      1020      1030
               •         •         •         •         •         •
          GTT ACT CGT CAA ACA TAT ATA ATC CAG GAG CTG GAA AAG CAA TTA AAC AGA GCT ACC ACC
           V   T   R   Q   T   Y   I   I   Q   E   L   E   K   Q   L   N   R   A   T   T>

1040      1050      1060      1070      1080      1090
               •         •         •         •         •         •
          AAC AAC AGT GTC CTT CAG AAG CAG CAA CTG GAG CTG ATG GAC ACA GTC CAC AAC CTT GTC
           N   N   S   V   L   Q   K   Q   Q   L   E   L   M   D   T   V   H   N   L   V>
```

Fig. 4B.

```
     1100        1110        1120        1130        1140        1150
       .           .           .           .           .           .
AAT CTT TGC ACT AAA GAA GGT GTT TTA CTA AAG GGA GGA AAA AGA GAG GAA GAG AAA CCA
 N   L   C   T   K   E   G   V   L   L   K   G   G   K   R   E   E   K   P>

1160        1170        1180        1190        1200        1210
       .           .           .           .           .           .
TTT AGA GAC TGT GCA GAT GTA TAT CAA GCT GGT TTT AAT AAA AGT GGA ATC TAC ACT ATT
 F   R   D   C   A   D   V   Y   Q   A   G   F   N   K   S   G   I   Y   T   I>

1220        1230        1240        1250        1260        1270
       .           .           .           .           .           .
TAT ATT AAT AAT ATG CCA GAA CCC AAA AAG GTG TTT TGC AAT ATG GAT GTC AAT GGG GGA
 Y   I   N   N   M   P   E   P   K   K   V   F   C   N   M   D   V   N   G   G>

1280        1290        1300        1310        1320        1330
       .           .           .           .           .           .
GGT TGG ACT GTA ATA CAA CAT CGT GAA GAT GGA AGT CTA GAT TTC CAA AGA GGC TGG AAG
 G   W   T   V   I   Q   H   R   E   D   G   S   L   D   F   Q   R   G   W   K>

1340        1350        1360        1370        1380        1390
       .           .           .           .           .           .
GAA TAT AAA ATG GGT TTT GGA AAT CCC TCC GGT GAA TAT TGG CTG GGG AAT GAG TTT ATT
 E   Y   K   M   G   F   G   N   P   S   G   E   Y   W   L   G   N   E   F   I>

1400        1410        1420        1430        1440        1450
       .           .           .           .           .           .
TTT GCC ATT ACC AGT CAG AGG CAG TAC ATG CTA AGA ATT GAG TTA ATG GAC TGG GAA GGG
 F   A   I   T   S   Q   R   Q   Y   M   L   R   I   E   L   M   D   W   E   G>

1460        1470        1480        1490        1500        1510
       .           .           .           .           .           .
AAC CGA GCC TAT TCA CAG TAT GAC AGA TTC CAC ATA GGA AAT GAA AAG CAA AAC TAT AGG
 N   R   A   Y   S   Q   Y   D   R   F   H   I   G   N   E   K   Q   N   Y   R>

1520        1530        1540        1550        1560        1570
       .           .           .           .           .           .
TTG TAT TTA AAA GGT CAC ACT GGG ACA GCA GGA AAA CAG AGC AGC CTG ATC TTA CAC GGT
 L   Y   L   K   G   H   T   G   T   A   G   K   Q   S   S   L   I   L   H   G>

1580        1590        1600        1610        1620        1630
       .           .           .           .           .           .
GCT GAT TTC AGC ACT AAA GAT GCT GAT AAT GAC AAC TGT ATG TGC AAA TGT GCC CTC ATG
 A   D   F   S   T   K   D   A   D   N   D   N   C   M   C   K   C   A   L   M>

1640        1650        1660        1670        1680        1690
       .           .           .           .           .           .
TTA ACA GGA GGA TGG TGG TTT GAT GCT TGT GGC CCC TCC AAT CTA AAT GGA ATG TTC TAT
 L   T   G   G   W   W   F   D   A   C   G   P   S   N   L   N   G   M   F   Y>

1700        1710        1720        1730        1740        1750
       .           .           .           .           .           .
ACT GCG GGA CAA AAC CAT GGA AAA CTG AAT GGG ATA AAG TGG CAC TAC TTC AAA GGG CCC
 T   A   G   Q   N   H   G   K   L   N   G   I   K   W   H   Y   F   K   G   P>

1760        1770        1780        1790        1800        1810
       .           .           .           .           .           .
AGT TAC TCC TTA CGT TCC ACA ACT ATG ATG ATT CGA CCT TTA GAT TTT TGA AAG CGCAATGT
 S   Y   S   L   R   S   T   T   M   M   I   R   P   L   D   F   *

1820        1830        1840        1850        1860        1870        1880        1890
  .           .           .           .           .           .           .           .
CAGAAGCGATTATGAAAGCAACAAAGAAATCCGGAGAAGCTGCCAGGTGAGAAACTGTTTGAAAACTTCAGAAGCAAACA 1900        1910        1920        1930        1940        1950        1960        1970
  .           .           .           .           .           .           .           .
ATATTGTCTCCCTTCCAGCAATAAGTGGTAGTTATGTGAAGTCACCAAGGTTCTTGACCGTGAATCTGGAGCCGTTTGAG 1980        1990        2000        2010        2020        2030        2040        2050
  .           .           .           .           .           .           .           .
TTCACAAGAGTCTCTACTTGGGGTGACAGTGCTCACGTGGCTCGACTATAGAAAACTCCACTGACTGTCGGGCTTTAAAA 2060        2070        2080        2090        2100        2110        2120        2130
  .           .           .           .           .           .           .           .
AGGGAAGAAACTGCTGAGCTTGCTGTGCTTCAAACTACTACTGGACCTTATTTTGGAACTATGGTAGCCAGATGATAAAT

2140
  .
ATGGTTAATTTC
```

Fig. 5A.

```
              10          20          30          40          50          60          70          80
               •           •           •           •           •           •           •           •
    CAGCTGACTCAGGCAGGCTCCATGCTGAACGGTCACACAGAGAGGAAACAATAAATCTCAGCTACTATGCAATAAATATC 90         100         110         120         130         140         150         160
               •           •           •           •           •           •           •           •
    TCAAGTTTTAACGAAGAAAAACATCATTGCAGTGAAATAAAAAATTTTAAAATTTTAGAACAAAGCTAACAAATGGCTAG 170         180         190         200         210         220         230         240
               •           •           •           •           •           •           •           •
    TTTTCTATGATTCTTCTTCAAACGCTTTCTTTGAGGGGGAAAGAGTCAAACAAACAAGCAGTTTTACCTGAAATAAAGAA 250         260         270         280         290         300         310
               •           •           •           •           •           •           •
    CTAGTTTTAGAGGTCAGAAGAAAGGAGCAAGTTTTGCGAGAGGCACGGAAGGAGTGTGCTGGCAGTACA ATG ACA
                                                                             M   T>

320             330             340             350             360             370
           •               •               •               •               •               •
    GTT TTC CTT TCC TTT GCT TTC CTC GCT GCC ATT CTG ACT CAC ATA GGG TGC AGC AAT CAG
     V   F   L   S   F   A   F   L   A   A   I   L   T   H   I   G   C   S   N   Q>

380             390             400             410             420             430
           •               •               •               •               •               •
    CGC CGA AGT CCA GAA AAC AGT GGG AGA AGA TAT AAC CGG ATT CAA CAT GGG CAA TGT GCC
     R   R   S   P   E   N   S   G   R   R   Y   N   R   I   Q   H   G   Q   C   A>

440             450             460             470             480             490
           •               •               •               •               •               •
    TAC ACT TTC ATT CTT CCA GAA CAC GAT GGC AAC TGT CGT GAG AGT ACG ACA GAC CAG TAC
     Y   T   F   I   L   P   E   H   D   G   N   C   R   E   S   T   T   D   Q   Y>

500             510             520             530             540             550
           •               •               •               •               •               •
    AAC ACA AAC GCT CTG CAG AGA GAT GCT CCA CAC GTG GAA CCG GAT TTC TCT TCC CAG AAA
     N   T   N   A   L   Q   R   D   A   P   H   V   E   P   D   F   S   S   Q   K>

560             570             580             590             600             610
           •               •               •               •               •               •
    CTT CAA CAT CTG GAA CAT GTG ATG GAA AAT TAT ACT CAG TGG CTG CAA AAA CTT GAG AAT
     L   Q   H   L   E   H   V   M   E   N   Y   T   Q   W   L   Q   K   L   E   N>

620             630             640             650             660             670
           •               •               •               •               •               •
    TAC ATT GTG GAA AAC ATG AAG TCG GAG ATG GCC CAG ATA CAG CAG AAT GCA GTT CAG AAC
     Y   I   V   E   N   M   K   S   E   M   A   Q   I   Q   Q   N   A   V   Q   N>

680             690             700             710             720             730
           •               •               •               •               •               •
    CAC ACG GCT ACC ATG CTG GAG ATA GGA ACC AGC CTC CTC TCT CAG ACT GCA GAG CAG ACC
     H   T   A   T   M   L   E   I   G   T   S   L   L   S   Q   T   A   E   Q   T>

740             750             760             770             780             790
           •               •               •               •               •               •
    AGA AAG CTG ACA GAT GTT GAG ACC CAG GTA CTA AAT CAA ACT TCT CGA CTT GAG ATA CAG
     R   K   L   T   D   V   E   T   Q   V   L   N   Q   T   S   R   L   E   I   Q>

800             810             820             830             840             850
           •               •               •               •               •               •
    CTG CTG GAG AAT TCA TTA TCC ACC TAC AAG CTA GAG AAG CAA CTT CTT CAA CAG ACA AAT
     L   L   E   N   S   L   S   T   Y   K   L   E   K   Q   L   L   Q   Q   T   N>

860             870             880             890             900             910
           •               •               •               •               •               •
    GAA ATC TTG AAG ATC CAT GAA AAA AAC AGT TTA TTA GAA CAT AAA ATC TTA GAA ATG GAA
     E   I   L   K   I   H   E   K   N   S   L   L   E   H   K   I   L   E   M   E>

920             930             940             950             960             970
           •               •               •               •               •               •
    GGA AAA CAC AAG GAA GAG TTG GAC ACC TTA AAG GAA GAG AAA GAG AAC CTT CAA GGC TTG
     G   K   H   K   E   E   L   D   T   L   K   E   E   K   E   N   L   Q   G   L>

980             990            1000            1010            1020            1030
           •               •               •               •               •               •
    GTT ACT CGT CAA ACA TAT ATA ATC CAG GAG CTG GAA AAG CAA TTA AAC AGA GCT ACC ACC
     V   T   R   Q   T   Y   I   I   Q   E   L   E   K   Q   L   N   R   A   T   T>

1040            1050            1060            1070            1080            1090
           •               •               •               •               •               •
    AAC AAC AGT GTC CTT CAG AAG CAG CAA CTG GAG CTG ATG GAC ACA GTC CAC AAC CTT GTC
     N   N   S   V   L   Q   K   Q   Q   L   E   L   M   D   T   V   H   N   L   V>
```

Fig. 5B.

```
              1100          1110         1120         1130         1140         1150
               .             .            .            .            .            .
         AAT CTT TGC ACT AAA GAA GTT TTA CTA AAG GGA GGA AAA AGA GAG GAA GAG AAA CCA TTT
          N   L   C   T   K   E   V   L   L   K   G   G   K   R   E   E   E   K   P   F>

1160          1170         1180         1190         1200         1210
               .             .            .            .            .            .
         AGA GAC TGT GCA GAT GTA TAT CAA GCT GGT TTT AAT AAA AGT GGA ATC TAC ACT ATT TAT
          R   D   C   A   D   V   Y   Q   A   G   F   N   K   S   G   I   Y   T   I   Y>

1220          1230         1240         1250         1260         1270
               .             .            .            .            .            .
         ATT AAT AAT ATG CCA GAA CCC AAA AAG GTG TTT TGC AAT ATG GAT GTC AAT GGG GGA GGT
          I   N   N   M   P   E   P   K   K   V   F   C   N   M   D   V   N   G   G   G>

1280          1290         1300         1310         1320         1330
               .             .            .            .            .            .
         TGG ACT GTA ATA CAA CAT CGT GAA GAT GGA AGT CTA GAT TTC CAA AGA GGC TGG AAG GAA
          W   T   V   I   Q   H   R   E   D   G   S   L   D   F   Q   R   G   W   K   E>

1340          1350         1360         1370         1380         1390
               .             .            .            .            .            .
         TAT AAA ATG GGT TTT GGA AAT CCC TCC GGT GAA TAT TGG CTG GGG AAT GAG TTT ATT TTT
          Y   K   M   G   F   G   N   P   S   G   E   Y   W   L   G   N   E   F   I   F>

1400          1410         1420         1430         1440         1450
               .             .            .            .            .            .
         GCC ATT ACC AGT CAG AGG CAG TAC ATG CTA AGA ATT GAG TTA ATG GAC TGG GAA GGG AAC
          A   I   T   S   Q   R   Q   Y   M   L   R   I   E   L   M   D   W   E   G   N>

1460          1470         1480         1490         1500         1510
               .             .            .            .            .            .
         CGA GCC TAT TCA CAG TAT GAC AGA TTC CAC ATA GGA AAT GAA AAG CAA AAC TAT AGG TTG
          R   A   Y   S   Q   Y   D   R   F   H   I   G   N   E   K   Q   N   Y   R   L>

1520          1530         1540         1550         1560         1570
               .             .            .            .            .            .
         TAT TTA AAA GGT CAC ACT GGG ACA GCA GGA AAA CAG AGC AGC CTG ATC TTA CAC GGT GCT
          Y   L   K   G   H   T   G   T   A   G   K   Q   S   S   L   I   L   H   G   A>

1580          1590         1600         1610         1620         1630
               .             .            .            .            .            .
         GAT TTC AGC ACT AAA GAT GCT GAT AAT GAC AAC TGT ATG TGC AAA TGT GCC CTC ATG TTA
          D   F   S   T   K   D   A   D   N   D   N   C   M   C   K   C   A   L   M   L>

1640          1650         1660         1670         1680         1690
               .             .            .            .            .            .
         ACA GGA GGA TGG TGG TTT GAT GCT TGT GGC CCC TCC AAT CTA AAT GGA ATG TTC TAT ACT
          T   G   G   W   W   F   D   A   C   G   P   S   N   L   N   G   M   F   Y   T>

1700          1710         1720         1730         1740         1750
               .             .            .            .            .            .
         GCG GGA CAA AAC CAT GGA AAA CTG AAT GGG ATA AAG TGG CAC TAC TTC AAA GGG CCC AGT
          A   G   Q   N   H   G   K   L   N   G   I   K   W   H   Y   F   K   G   P   S>

1760          1770         1780         1790         1800         1810
               .             .            .            .            .            .
         TAC TCC TTA CGT TCC ACA ACT ATG ATG ATT CGA CCT TTA GAT TTT TGA AAGCGCAATGTCAGAA
          Y   S   L   R   S   T   T   M   M   I   R   P   L   D   F   *>

1820        1830          1840         1850         1860         1870        1880         1890
    .           .             .            .            .            .           .            .
  GCGATTATGAAAGCAACAAAGAAATCCGGAGAAGCTGCCAGGTGAGAAACTGTTTGAAAACTTCAGAAGCAAACAATATT 1900        1910          1920         1930         1940         1950        1960         1970
    .           .             .            .            .            .           .            .
  GTCTCCCTTCCAGCAATAAGTGGTAGTTATGTGAAGTCACCAAGGTTCTTGACCGTGAATCTGGAGCCGTTTGAGTTCAC 1980        1990          2000         2010         2020         2030        2040         2050
    .           .             .            .            .            .           .            .
  AAGAGTCTCTACTTGGGGTGACAGTGCTCACGTGGCTCGACTATAGAAAACTCCACTGACTGTCGGCTTTAAAAAGGGA 2060        2070          2080         2090         2100         2110        2120         2130
    .           .             .            .            .            .           .            .
  AGAAACTGCTGAGCTTGCTGTGCTTCAAACTACTACTGGACCTTATTTTGGAACTATGGTAGCCAGATGATAAATATGGT

2140
    .
  TAATTTC
```

Fig. 6A.

```
              10         20         30         40         50         60         70         80
               .          .          .          .          .          .          .          .
     GAATTCCTGGGTTGGTGTTTATCTCCTCCCAGCCTTGAGGGAGGGAACAACACTGTAGGATCTGGGGAGAGAGGAACAAA 90        100        110        120        130        140        150        160
               .          .          .          .          .          .          .          .
     GGACCGTGAAAGCTGCTCTGTAAAAGCTGACACAGCCCTCCCAAGTGAGCAGGACTGTTCTTCCCACTGCAATCTGACAG 170        180        190        200        210        220        230        240
               .          .          .          .          .          .          .          .
     TTTACTGCATGCCTGGAGAGAACACAGCAGTAAAAACCAGGTTTGCTACTGGAAAAAGAGGAAAGAGAAGACTTTCATTG 250        260        270        280        290        300        310        320
               .          .          .          .          .          .          .          .
     ACGGACCCAGCCATGGCAGCGTAGCAGCCCTGCGTTTCAGACGGCAGCAGCTCGGGACTCTGGACGTGTGTTTGCCCTCA 330        340        350        360        370        380
               .          .          .          .          .          .
     AGTTTGCTAAGCTGCTGGTTTATTACTGAAGAAAGA ATG TGG CAG ATT GTT TTC TTT ACT CTG AGC TGT
                                           M   W   Q   I   V   F   F   T   L   S   C>

390             400             410             420             430             440
       .               .               .               .               .               .
     GAT CTT GTC TTG GCC GCA GCC TAT AAC AAC TTT CGG AAG AGC ATG GAC AGC ATA GGA AAG
      D   L   V   L   A   A   A   Y   N   N   F   R   K   S   M   D   S   I   G   K>

450             460             470             480             490             500
       .               .               .               .               .               .
     AAG CAA TAT CAG GTC CAG CAT GGG TCC TGC AGC TAC ACT TTC CTC CTG CCA GAG ATG GAC
      K   Q   Y   Q   V   Q   H   G   S   C   S   Y   T   F   L   L   P   E   M   D>

510             520             530             540             550             560
       .               .               .               .               .               .
     AAC TGC CGC TCT TCC TCC AGC CCC TAC GTG TCC AAT GCT GTG CAG AGG GAC GCG CCG CTC
      N   C   R   S   S   S   S   P   Y   V   S   N   A   V   Q   R   D   A   P   L>

570             580             590             600             610             620
       .               .               .               .               .               .
     GAA TAC GAT GAC TCG GTG CAG AGG CTG CAA GTG CTG GAG AAC ATC ATG GAA AAC AAC ACT
      E   Y   D   D   S   V   Q   R   L   Q   V   L   E   N   I   M   E   N   N   T>

630             640             650             660             670             680
       .               .               .               .               .               .
     CAG TGG CTA ATG AAG CTT GAG AAT TAT ATC CAG GAC AAC ATG AAG AAA GAA ATG GTA GAG
      Q   W   L   M   K   L   E   N   Y   I   Q   D   N   M   K   K   E   M   V   E>

690             700             710             720             730             740
       .               .               .               .               .               .
     ATA CAG CAG AAT GCA GTA CAG AAC CAG ACG GCT GTG ATG ATA GAA ATA GGG ACA AAC CTG
      I   Q   Q   N   A   V   Q   N   Q   T   A   V   M   I   E   I   G   T   N   L>

750             760             770             780             790             800
       .               .               .               .               .               .
     TTG AAC CAA ACA GCT GAG CAA ACG CGG AAG TTA ACT GAT GTG GAA GCC CAA GTA TTA AAT
      L   N   Q   T   A   E   Q   T   R   K   L   T   D   V   E   A   Q   V   L   N>

810             820             830             840             850             860
       .               .               .               .               .               .
     CAG ACC ACG AGA CTT GAA CTT CAG CTC TTG GAA CAC TCC CTC TCG ACA AAC AAA TTG GAA
      Q   T   T   R   L   E   L   Q   L   L   E   H   S   L   S   T   N   K   L   E>

870             880             890             900             910             920
       .               .               .               .               .               .
     AAA CAG ATT TTG GAC CAG ACC AGT GAA ATA AAC AAA TTG CAA GAT AAG AAC AGT TTC CTA
      K   Q   I   L   D   Q   T   S   E   I   N   K   L   Q   D   K   N   S   F   L>

930             940             950             960             970             980
       .               .               .               .               .               .
     GAA AAG AAG GTG CTA GCT ATG GAA GAC AAG CAC ATC ATC CAA CTA CAG TCA ATA AAA GAA
      E   K   K   V   L   A   M   E   D   K   H   I   I   Q   L   Q   S   I   K   E>

990            1000            1010            1020            1030            1040
       .               .               .               .               .               .
     GAG AAA GAT CAG CTA CAG GTG TTA GTA TCC AAG CAA AAT TCC ATC ATT GAA GAA CTA GAA
      E   K   D   Q   L   Q   V   L   V   S   K   Q   N   S   I   I   E   E   L   E>

1050            1060            1070            1080            1090            1100
       .               .               .               .               .               .
     AAA AAA ATA GTG ACT GCC ACG GTG AAT AAT TCA GTT CTT CAA AAG CAG CAA CAT GAT CTC
      K   K   I   V   T   A   T   V   N   N   S   V   L   Q   K   Q   Q   H   D   L>
```

Fig. 6B.

```
      1110        1120        1130        1140        1150        1160
       •           •           •           •           •           •
      ATG GAG ACA GTT AAT AAC TTA CTG ACT ATG ATG TCC ACA TCA AAC TCA GCT AAG GAC CCC
       M   E   T   V   N   N   L   L   T   M   M   S   T   S   N   S   A   K   D   P>

1170        1180        1190        1200        1210        1220
       •           •           •           •           •           •
      ACT GTT GCT AAA GAA GAA CAA ATC AGC TTC AGA GAC TGT GCT GAA GTA TTC AAA TCA GGA
       T   V   A   K   E   E   Q   I   S   F   R   D   C   A   E   V   F   K   S   G>

1230        1240        1250        1260        1270        1280
       •           •           •           •           •           •
      CAC ACC ACA AAT GGC ATC TAC ACG TTA ACA TTC CCT AAT TCT ACA GAA GAG ATC AAG GCC
       H   T   T   N   G   I   Y   T   L   T   F   P   N   S   T   E   E   I   K   A>

1290        1300        1310        1320        1330        1340
       •           •           •           •           •           •
      TAC TGT GAC ATG GAA GCT GGA GGA GGC GGG TGG ACA ATT ATT CAG CGA CGT GAG GAT GGC
       Y   C   D   M   E   A   G   G   G   G   W   T   I   I   Q   R   R   E   D   G>

1350        1360        1370        1380        1390        1400
       •           •           •           •           •           •
      AGC GTT GAT TTT CAG AGG ACT TGG AAA GAA TAT AAA GTG GGA TTT GGT AAC CCT TCA GGA
       S   V   D   F   Q   R   T   W   K   E   Y   K   V   G   F   G   N   P   S   G>

1410        1420        1430        1440        1450        1460
       •           •           •           •           •           •
      GAA TAT TGG CTG GGA AAT GAG TTT GTT TCG CAA CTG ACT AAT CAG CAA CGC TAT GTG CTT
       E   Y   W   L   G   N   E   F   V   S   Q   L   T   N   Q   Q   R   Y   V   L>

1470        1480        1490        1500        1510        1520
       •           •           •           •           •           •
      AAA ATA CAC CTT AAA GAC TGG GAA GGG AAT GAG GCT TAC TCA TTG TAT GAA CAT TTC TAT
       K   I   H   L   K   D   W   E   G   N   E   A   Y   S   L   Y   E   H   F   Y>

1530        1540        1550        1560        1570        1580
       •           •           •           •           •           •
      CTC TCA AGT GAA GAA CTC AAT TAT AGG ATT CAC CTT AAA GGA CTT ACA GGG ACA GCC GGC
       L   S   S   E   E   L   N   Y   R   I   H   L   K   G   L   T   G   T   A   G>

1590        1600        1610        1620        1630        1640
       •           •           •           •           •           •
      AAA ATA AGC AGC ATC AGC CAA CCA GGA AAT GAT TTT AGC ACA AAG GAT GGA GAC AAC GAC
       K   I   S   S   I   S   Q   P   G   N   D   F   S   T   K   D   G   D   N   D>

1650        1660        1670        1680        1690        1700
       •           •           •           •           •           •
      AAA TGT ATT TGC AAA TGT TCA CAA ATG CTA ACA GGA GGC TGG TGG TTT GAT GCA TGT GGT
       K   C   I   C   K   C   S   Q   M   L   T   G   G   W   W   F   D   A   C   G>

1710        1720        1730        1740        1750        1760
       •           •           •           •           •           •
      CCT TCC AAC TTG AAC GGA ATG TAC TAT CCA CAG AGG CAG AAC ACA AAT AAG TTC AAC GGC
       P   S   N   L   N   G   M   Y   Y   P   Q   R   Q   N   T   N   K   F   N   G>

1770        1780        1790        1800        1810        1820
       •           •           •           •           •           •
      ATT AAA TGG TAC TAC TGG AAA GGC TCA GGC TAT TCG CTC AAG GCC ACA ACC ATG ATG ATC
       I   K   W   Y   Y   W   K   G   S   G   Y   S   L   K   A   T   T   M   M   I>

1830        1840        1850        1860        1870        1880        1890        1900
       •           •           •           •           •           •           •           •
      CGA CCA GCA GAT TTC TAAACATCCCAGTCCACCTGAGGAACTGTCTCGAACTATTTTCAAAGACTTAAGCCCAGT
       R   P   A   D   F>

1910        1920        1930        1940        1950        1960        1970        1980
          •           •           •           •           •           •           •           •
      GCACTGAAAGTCACGGCTGCGCACTGTGTCCTCTTCCACCACAGAGGGCGTGTGCTCGGTGCTGACGGGACCCACATGCT 1990        2000        2010        2020        2030        2040        2050        2060
          •           •           •           •           •           •           •           •
      CCAGATTAGAGCCTGTAAACTTTATCACTTAAACTTGCATCACTTAACGGACCAAAGCAAGACCCTAAACATCCATAATT 2070        2080        2090        2100        2110        2120        2130        2140
          •           •           •           •           •           •           •           •
      GTGATTAGACAGAACACCTATGCAAAGATGAACCCGAGGCTGAGAATCAGACTGACAGTTTACAGACGCTGCTGTCACAA 2150        2160        2170        2180        2190        2200        2210        2220
          •           •           •           •           •           •           •           •
      CCAAGAATGTTATGTGCAAGTTTATCAGTAAATAACTGGAAAACAGAACACTTATGTTATACAATACAGATCATCTTGGA 2230        2240        2250        2260        2270        2280
          •           •           •           •           •           •
      ACTGCATTCTTCTGAGCACTGTTTATACACTGTGTAAATACCCATATGTCCTGAATTC
```

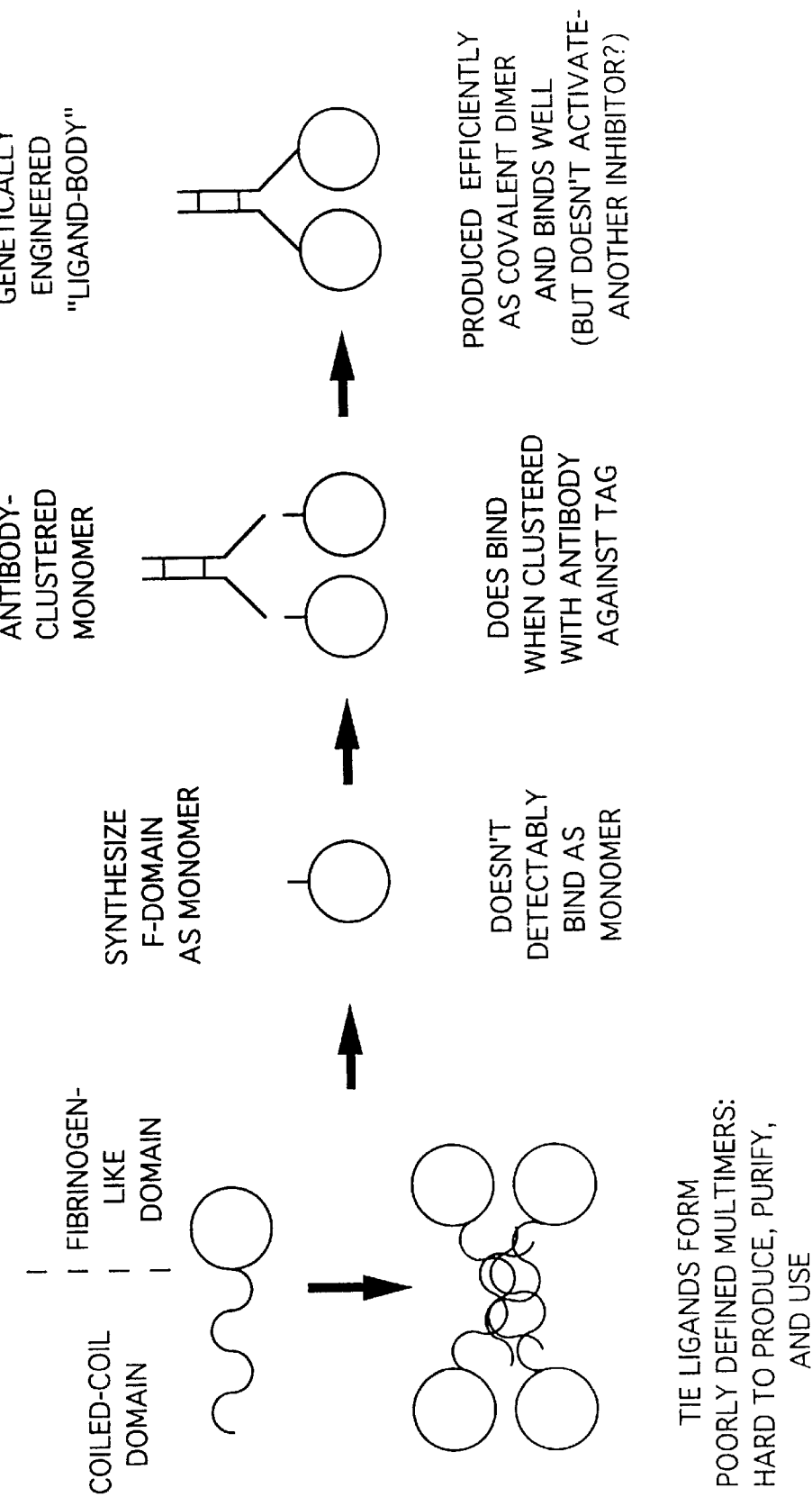

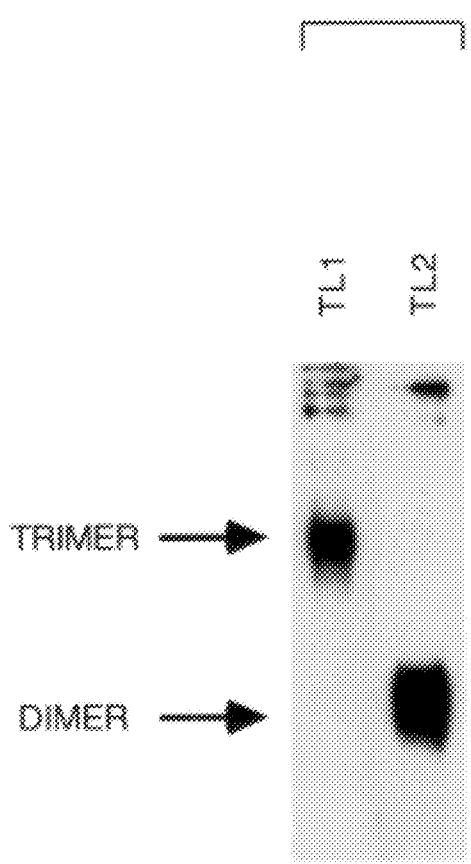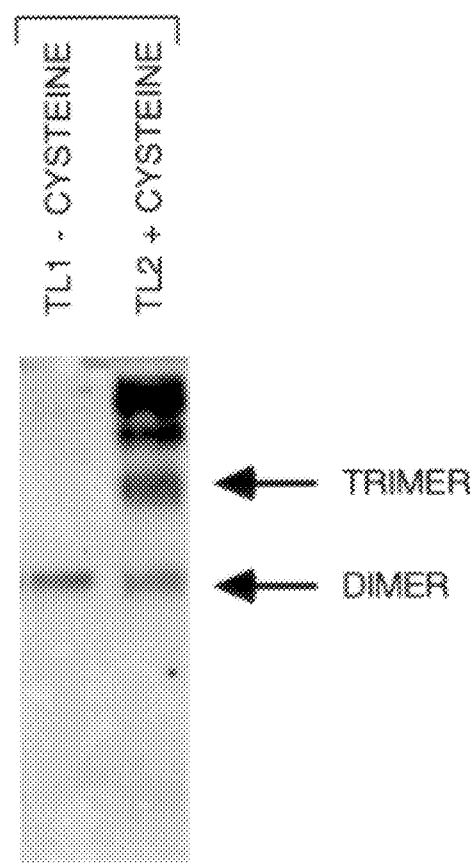

Fig. 21A.

```
           10         20         30         40         50         60         70         80         90
            *          *          *          *          *          *          *          *          *
CTGTCCTGGT ACCTGACAAG ACCACCTCAC CACCACTTGG TCTCAG ATG CTC TGC CAG CCA GCT ATG CTA CTA GAT GGC CTC CTC CTG CTG
                                                     M   L   C   Q   P   A   M   L   L   D   G   L   L   L   L>

100        110        120        130        140        150        160        170
            *          *          *          *          *          *          *          *          *
GCC ACC ATG GCT GCA GCC CAG CAC AGA GGG CCA GAA GCC GGT GGG CAC CGC CAG ATT CAC CAG GTC CGG CGT GGC CAG TGC AGC
 A   T   M   A   A   A   Q   H   R   G   P   E   A   G   G   H   R   Q   I   H   Q   V   R   R   G   Q   C   S>

180        190        200        210        220        230        240        250
        *          *          *          *          *          *          *          *          *
TAC ACC TTT GTG GTG CCG GAG CCT GAT ATC TGC CAG CTG GCG CCG ACA GCG GCG CCT GAG GCT TTG GGG GGC TCC AAT AGC CTC
 Y   T   F   V   V   P   E   P   D   I   C   Q   L   A   P   T   A   A   P   E   A   L   G   G   S   N   S   L>

260        270        280        290        300        310        320        330        340
  *          *          *          *          *          *          *          *          *
CAG AGG GAC TTG CCT GCC TCG AGG CTG CAC CTA ACA GAC TGG CGA GCC CAG AGG GCC CAG CGG GCC CAG CGT GTG AGC CAG CTG
 Q   R   D   L   P   A   S   R   L   H   L   T   D   W   R   A   Q   R   A   Q   R   A   Q   R   V   S   Q   L>

350        360        370        380        390        400        410        420
         *          *          *          *          *          *          *          *          *
GAG AAG ATA CTA GAG AAT AAC ACT CAG TGG CTG CTG AAG CTG GAG CAG TCC ATC AAG GTG AAC TTG AGG TCA CAC CTG GTG CAG
 E   K   I   L   E   N   N   T   Q   W   L   L   K   L   E   Q   S   I   K   V   N   L   R   S   H   L   V   Q>

430        440        450        460        470        480        490        500        510
  *          *          *          *          *          *          *          *          *
GCC CAG CAG GAC ACA ATC CAG AAC CAG ACA ACT ACC ATG CTG GCA CTG GGT GCC AAC CTC ATG AAC CAG ACC AAA GCT CAG ACC
 A   Q   Q   D   T   I   Q   N   Q   T   T   T   M   L   A   L   G   A   N   L   M   N   Q   T   K   A   Q   T>

520        530        540        550        560        570        580        590
         *          *          *          *          *          *          *          *          *
CAC AAG CTG ACT GCT GTG GAG GCA CAG GTC CTA AAC CAG ACA TTG CAC ATG AAG ACC CAA ATG CTG GAG AAC TCA CTG TCC ACC
 H   K   L   T   A   V   E   A   Q   V   L   N   Q   T   L   H   M   K   T   Q   M   L   E   N   S   L   S   T>

600        610        620        630        640        650        660        670
        *          *          *          *          *          *          *          *          *
AAC AAG CTG GAG CGG CAG ATG CTG ATG CAG AGC CGA GAG CTG CAG CGG CTG CAG GGT CGC AAC AGG GCC CTG GAG ACC AGG CTG
 N   K   L   E   R   Q   M   L   M   Q   S   R   E   L   Q   R   L   Q   G   R   N   R   A   L   E   T   R   L>

680        690        700        710        720        730        740        750        760
  *          *          *          *          *          *          *          *          *
CAG GCA CTG GAA GCA CAA CAT CAG GCC CAG CTT AAC AGC CTC CAA GAG AAG AGG GAA CAA CTG CAC AGT CTC CTG GGC CAT CAG
 Q   A   L   E   A   Q   H   Q   A   Q   L   N   S   L   Q   E   K   R   E   Q   L   H   S   L   L   G   H   Q>

770        780        790        800        810        820        830        840
             *          *          *          *          *          *          *          *          *
ACC GGG ACC CTG GCT AAC CTG AAG CAC AAT CTG CAC GCT CTC AGC AGC AAT TCC AGC TCC CTG CAG CAG CAG CAG CAG CAA CTG
 T   G   T   L   A   N   L   K   H   N   L   H   A   L   S   S   N   S   S   S   L   Q   Q   Q   Q   Q   Q   L>

850        860        870        880        890        900        910        920        930
  *          *          *          *          *          *          *          *          *
ACG GAG TTT GTA CAG CGC CTG GTA CGG ATT GTA GCC CAG GAC CAG CAT CCG GTT TCC TTA AAG ACA CCT AAG CCA GTG TTC CAG
 T   E   F   V   Q   R   L   V   R   I   V   A   Q   D   Q   H   P   V   S   L   K   T   P   K   P   V   F   Q>

940        950        960        970        980        990       1000       1010
          *          *          *          *          *          *          *          *          *
GAC TGT GCA GAG ATC AAG CGC TCC GGG GTT AAT ACC AGC GGT GTC TAT ACC ATC TAT GAG ACC AAC ATG ACA AAG CCT CTC AAG
 D   C   A   E   I   K   R   S   G   V   N   T   S   G   V   Y   T   I   Y   E   T   N   M   T   K   P   L   K>

1020       1030       1040       1050       1060       1070       1080       1090
      *          *          *          *          *          *          *          *          *
GTG TTC TGT GAC ATG GAG ACT GAT GGA GGT GGC TGG ACC CTC ATC CAG CAC CGG GAG GAT GGA AGC GTA AAT TTC CAG AGG ACC
 V   F   C   D   M   E   T   D   G   G   G   W   T   L   I   Q   H   R   E   D   G   S   V   N   F   Q   R   T>

1100       1110       1120       1130       1140       1150       1160       1170       1180
   *          *          *          *          *          *          *          *          *
TGG GAA GAA TAC AAA GAG GGT TTT GGT AAT GTG GCC AGA GAG CAC TGG CTG GGC AAT GAG GCT GTG CAC CGC CTC ACC AGC AGA
 W   E   E   Y   K   E   G   F   G   N   V   A   R   E   H   W   L   G   N   E   A   V   H   R   L   T   S   R>

1190       1200       1210       1220       1230       1240       1250       1260
          *          *          *          *          *          *          *          *          *
ACG GCC TAC TTG CTA CGC GTG GAA CTG CAT GAC TGG GAA GGC CGC CAG ACC TCC ATC CAG TAT GAG AAC TTC CAG CTG GGC AGC
 T   A   Y   L   L   R   V   E   L   H   D   W   E   G   R   Q   T   S   I   Q   Y   E   N   F   Q   L   G   S>

1270       1280       1290       1300       1310       1320       1330       1340       1350
   *          *          *          *          *          *          *          *          *
GAG AGG CAG CGG TAC AGC CTC TCT GTG AAT GAC AGC AGC AGT TCA GCA GGG CGC AAG AAC AGC CTG GCT CCT CAG GGC ACC AAG
 E   R   Q   R   Y   S   L   S   V   N   D   S   S   S   S   A   G   R   K   N   S   L   A   P   Q   G   T   K>

1360       1370       1380       1390       1400       1410       1420       1430
           *          *          *          *          *          *          *          *          *
TTC AGC ACC AAA GAC ATG GAC AAT GAT AAC TGC ATG TGT AAA TGT GCT CAG ATG CTG TCT GGA GGG TGG TGG TTT GAT GCC TGT
 F   S   T   K   D   M   D   N   D   N   C   M   C   K   C   A   Q   M   L   S   G   G   W   W   F   D   A   C>
```

Fig. 21B.

```
        1440         1450         1460         1470         1480         1490         1500         1510
         .            .            .            .            .            .            .            .
         *            *            *            *            *            *            *            *
GGC CTC TCC AAC CTC AAT GGC ATC TAC TAT TCA GTT CAT CAG CAC TTG CAC AAG ATC AAT GGC ATC CGC TGG CAC TAC TTC CGA
 G   L   S   N   L   N   G   I   Y   Y   S   V   H   Q   H   L   H   K   I   N   G   I   R   W   H   Y   F   R>

1520         1530         1540         1550         1560         1570         1580         1590         1600
 .            .            .            .            .            .            .            .            .
 *            *            *            *            *            *            *            *            *
GGC CCC AGC TAC TCA CTG CAC GGC ACA CGC ATG ATG CTG AGG CCA ATG GGT GCC TGA CACA CAGCCCTGCA GAGACTGATG
 G   P   S   Y   S   L   H   G   T   R   M   M   L   R   P   M   G   A   *>

1610         1620         1630         1640         1650         1660         1670         1680         1690         1700
          .            .            .            .            .            .            .            .            .            .
          *            *            *            *            *            *            *            *            *            *
CCGTAGGAGG ATTCTCAACC CAGGTGACTC TGTGCACGCT GGGCCCTGCC CAGAAATCAG TGCCCAGGGC TCATCTTGAC ATTCTGGAAC ATCGGAACCA 1710         1720         1730         1740         1750         1760         1770         1780         1790         1800
          .            .            .            .            .            .            .            .            .            .
          *            *            *            *            *            *            *            *            *            *
GCTTACCTTG CCCCTGAATT ACAAGAATTC ACCTGCCTCC CTGTTGCCCT CTAATTGTGA AATTGCTGGG TGCTTGAAGG CACCTGCCTC TGTTGGAACC 1810         1820         1830         1840
          .            .            .            .
          *            *            *            *
ATACTCTTTC CCCCTCCTGC TGCATGCCCG GGAATCCCTG CCATGAACT
```

TIE LIGAND-3, METHODS OF MAKING AND USES THEREOF

Throughout this application various publications are referenced. The disclosures of these publications in their entireties are hereby incorporated by reference into this application.

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to a novel mammalian ligand, known as TIE ligand-3, that binds TIE receptor, as well as to methods of making and using the TIE ligand-3.

The invention further provides a nucleic acid sequence encoding a mammalian TIE ligand-3, and methods for the generation of nucleic acid encoding TIE ligand-3 and the gene product. The mammalian TIE ligand-3, as well as nucleic acid encoding it, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. In addition, the mammalian ligand may be used to promote the proliferation and/or differentiation of hematopoietic stem cells.

More generally, biologically active mammalian TIE ligand-3 may be used to promote the growth, survival, migration, and/or differentiation and/or stabilization or destabilization of cells expressing TIE receptor. Biologically active TIE ligand-3 may be used for the in vitro maintenance of TIE receptor expressing cells in culture. Cells and tissues expressing TIE receptor include, for example, cardiac and vascular endothelial cells, lens epithelium and heart epicardium and early hematopoietic cells. Alternatively, such mammalian ligand may be used to support cells which are engineered to express TIE receptor. Further, TIE ligand-3 and its cognate receptor may be used in assay systems to identify agonists or antagonists of TIE receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosine residues in proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235: 442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "TIE" which is an abbreviation for "tyrosine kinase with Ig and EGF homology domains." Partanen, et al. Mol. Cell. Biol. 5 12: 1698–1707 (1992).

It has been reported that tie mRNA is present in all human fetal and mouse embryonic tissues. Upon inspection, tie message has been localized to the cardiac and vascular endothelial cells. Specifically, tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus the TIEs have been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene, which, like tie, has been reported to be expressed in the mouse exclusively in endothelial cells and their presumptive progenitors. Dumont, et al. Oncogene 8: 1293–1301 (1993). The human homolog of tie-2 is described in Ziegler, U.S. Pat. No. 5,447,860 which issued on Sept. 5, 1995 (wherein it is referred to as "ork"), which is incorporated in its entirety herein.

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. Analyses of mouse embryos deficient in TIE-2 illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

The TIE receptors are also expressed in primitive hematopoietic stem cells, B cells and a subset of megakaryocytic cells, thus suggesting the role of ligands which bind these receptors in early hematopoiesis, in the differentiation and/ or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

SUMMARY OF THE INVENTION

The present invention provides for a composition comprising TIE ligand-3 substantially free of other proteins. The invention also provides for an isolated nucleic acid molecule encoding TIE ligand-3. The isolated nucleic acid may be DNA, cDNA or RNA. The invention also provides for a vector comprising an isolated nucleic acid molecule encoding TIE ligand-3. The invention further provides for a host-vector system for the production in a suitable host cell of a polypeptide having the biological activity of TIE ligand-3. The suitable host cell may be bacterial, yeast, insect or mammalian. The invention also provides for a method of producing a polypeptide having the biological activity of TIE ligand-3 which comprises growing cells of the host-vector system under conditions permitting production of the polypeptide and recovering the polypeptide so produced.

The invention herein described of an isolated nucleic acid molecule encoding TIE ligand-3 further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds TIE ligand-3. The antibody may be monoclonal or polyclonal. Thus the invention further provides for therapeutic compositions comprising an antibody which specifically binds TIE ligand-3 in a pharmaceutically acceptable vehicle. The invention also provides for a method of blocking blood vessel growth in a mammal by administering an effective amount of a therapeutic composition comprising an antibody which specifically binds TIE ligand-3 in a pharmaceutically acceptable vehicle.

The invention further provides for therapeutic compositions comprising TIE ligand-3 in a pharmaceutically acceptable vehicle. The invention also provides for a method of promoting neovascularization in a patient by administering an effective amount of a therapeutic composition comprising TIE ligand-3 in a pharmaceutically acceptable vehicle. In one embodiment, the method may be used to promote wound healing. In another embodiment, the method may be used to treat ischemia. In yet another embodiment, TIE ligand-3 is used, alone or in combination with other hematopoietic factors, to promote the proliferation or differentiation of hematopoietic stem cells, B cells or megakaryocytic cells.

Alternatively, the invention provides that TIE ligand-3 may be conjugated to a cytotoxic agent and a therapeutic composition prepared therefrom. The invention further provides for a receptorbody which specifically binds TIE ligand-3. The invention further provides for therapeutic compositions comprising a receptorbody which specifically binds TIE ligand-3 in a pharmaceutically acceptable vehicle. The invention also provides for a method of blocking blood vessel growth in a mammal by administering an effective amount of a therapeutic composition comprising a receptorbody which specifically binds TIE ligand-3 in a pharmaceutically acceptable vehicle.

The invention also provides for a TIE receptor antagonist as well as a method of inhibiting TIE ligand-3 biological activity in a mammal comprising administering to the mammal an effective amount of a TIE antagonist. According to the invention, the antagonist may be the TIE ligand-3 as described herein, an antibody or other molecule capable of specifically binding either TIE ligand-3 or TIE receptor, or ligandbody comprising the fibrinogen-like domain of TIE ligand-3.

BRIEF DESCRIPTION OF THE FIGURES

FIG. 1A: embryos treated with EHK-1 RB (rEHK-1 ecto/hIgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIG. 4A and 4B—Nucleic acid and deduced amino acid (single letter code) sequences of human TIE-2 ligand 1 from clone λgt10 encoding htie-2 ligand 1 (SEQ.ID NOS.1&2)

FIG. 5A and 5B—Nucleic acid and deduced amino acid (single letter code) sequences of human TIE-2 ligand 1 from T98G clone (SEQ. ID NOS.3&4).

FIG. 6A and 6B—Nucleic acid and deduced amino acid (single letter code) sequences of human TIE-2 ligand 2 from clone pBluescript KS encoding human TIE 2 ligand 2 (SEQ. ID NOS.5&6)

FIG. 17—Diagrammatic representation of the TIE-2 ligands, showing the "coiled coil" and fibrinogen-like domains and the engineering of multimers of the fibrinogen-like domains using antibodies to myc-tags as well as Fc tagging.

FIG. 18A and 18B—Western blot of the covalent multimeric structure of TL1 and TL2 (FIG. 18A) and the interconversion of TL1 and TL2 by the mutation of one cysteine (FIG. 18B).

FIGS. 21A and 21B—Nucleotide and deduced amino acid (single letter code) sequences of TIE ligand-3 (SEQ. ID NOS.7&8). The coding sequence starts at position 47. The fibrinogen-like domain starts at position 929.

DETAILED DESCRIPTION OF THE INVENTION

Figure 1A:
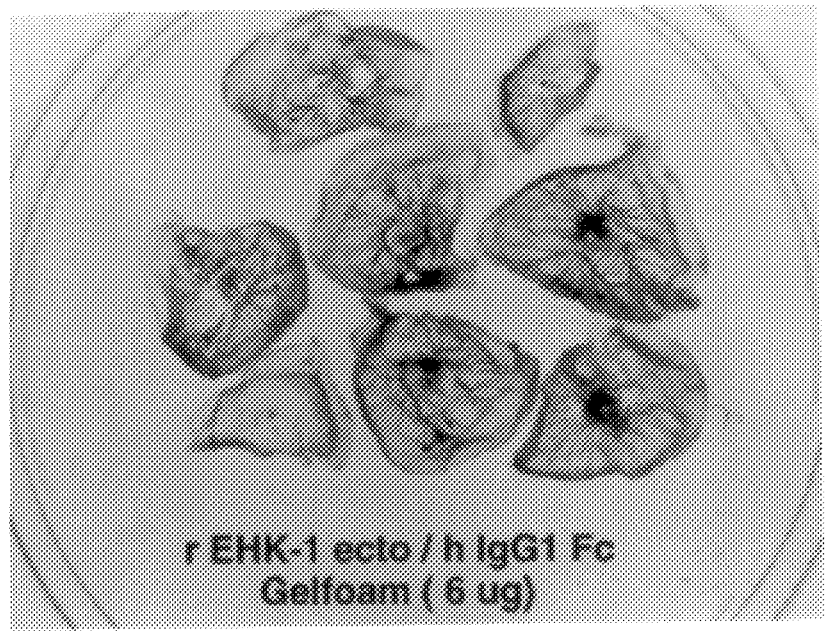
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 µg of RB was inserted immediately under the CAM of 1-day chick embryos. After 3 further days of incubation, 4 day old embryos and surrounding CAM were removed and examined.

As described in greater detail below, applicants have isolated and identified a novel mammalian ligand related to the TIE-2 ligands that bind the TIE-2 receptor. The novel mammalian ligand, which may be purified from nature, or made recombinantly, is referred to herein as TIE ligand-3 (or TL3). The TIE-2 ligands are referred to herein as TIE-2 ligand 1 (or TL1) and TIE-2 ligand 2 (or TL2).

The present invention comprises the TIE ligand-3, as defined by its amino acid sequence, as well as functionally equivalent variants thereof comprising naturally occurring allelic variations, as well as proteins or peptides comprising substitutions, deletions or insertional mutants of the described sequences, which bind TIE receptor and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity as the TIE ligand-3 described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. E. coli) expression systems. Functional equivalents also include mutants in which amino acid substitutions are made for cysteine molecules to improve stability of the molecules and to prevent unwanted crosslinking. As used herein, the term "TIE ligand-3" also includes fragments of TIE ligand-3 which are associated with the binding of the ligand to TIE receptor. In a preferred embodiment, TIE ligand-3 comprises a fibrinogen-like domain as described herein.

The present invention also encompasses the nucleotide sequence that encodes the protein described herein as TIE ligand-3, as well as host cells, including yeast, bacteria, viruses, and mammalian cells, which are genetically engineered to produce the protein, by e.g. transfection, transduction, infection, electroporation, or microinjection of nucleic acid encoding the TIE ligand-3 described herein in a suitable expression vector. The present invention also encompasses introduction of the nucleic acid encoding TIE ligand-3 through gene therapy techniques such as is described, for example, in Finkel and Epstein FASEB J. 9:843–851 (1995); Guzman, et al. PNAS (USA) 91:10732–10736 (1994).

One skilled in the art will also recognize that the present invention encompasses DNA and RNA sequences that hybridize to a deduced TIE ligand-3 encoding sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a sequence deduced from an amino acid sequence of a TIE ligand-3 prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds TIE receptor and which has an amino acid sequence and other primary, secondary and tertiary characteristics that are sufficiently duplicative of the ligand described herein so as to confer on the molecule the same biological activity as the TIE ligand-3 described herein.

Accordingly, the present invention encompasses an isolated and purified nucleic acid molecule comprising a nucleotide sequence encoding a mammalian TIE ligand-3, wherein the nucleotide sequence is selected from the group consisting of:
(a) the nucleotide sequence comprising the coding region of TIE ligand-3 as set forth in FIGS. 21A and 21B (SEQ. ID NO.7);
(b) the nucleotide sequence comprising the coding region of the fibrinogen-like domain of TIE ligand-3 as set forth in FIGS. 21A and 21B (SEQ. ID NO.7);
(c) a nucleotide sequence that hybridizes under moderately stringent conditions to the nucleotide sequence of (a) or (b) and which encodes a ligand that binds TIE receptor; and
(d) a nucleotide sequence which, but for the degeneracy of the genetic code would hybridize to a nucleotide sequence of (a), (b) or (c), and which encodes a ligand that binds TIE receptor.

The present invention further provides for an isolated and purified TIE ligand-3 encoded by an isolated nucleic acid molecule of the invention. The invention also provides for a vector which comprises an isolated nucleic acid molecule comprising a nucleic acid sequence encoding mammalian TIE ligand-3.

Any of the methods known to one skilled in the art for the insertion of DNA fragments into a vector may be used to construct expression vectors encoding TIE ligand-3 using appropriate transcriptional/translational control signals and the protein coding sequences. These methods may include in vitro recombinant DNA and synthetic techniques and in vivo recombinations (genetic recombination). Expression of a nucleic acid sequence encoding TIE ligand-3 or peptide fragments thereof may be regulated by a second nucleic acid sequence which is operably linked to the TIE ligand-3 encoding sequence such that the TIE ligand-3 protein or peptide is expressed in a host transformed with the recombinant DNA molecule. For example, expression of TIE ligand-3 described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the met-allothionein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals; elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells [Hanahan, Nature 315:115–122 (1985)]; immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocytes in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding TIE ligand-3 to modulate its expression. Ecker, U.S. Pat. No. 5,166,195, issued Nov. 24, 1992.

Thus, according to the invention, expression vectors capable of being replicated in a bacterial or eukaryotic host comprising a nucleic acid encoding TIE ligand-3 as described herein, are used to transfect a host and thereby direct expression of such nucleic acid to produce TIE ligand-3, which may then be recovered in a biologically active form. As used herein, a biologically active form includes a form capable of binding to TIE receptor and causing a biological response such as a differentiated function or influencing the phenotype of the cell expressing the receptor. Such biologically active forms could, for example, induce phosphorylation of the tyrosine kinase domain of TIE receptor. Alternatively, the biological activity may be an effect as an antagonist to the TIE receptor. In alternative embodiments, the active form of TIE ligand-3 is one that can recognize TIE receptor and thereby act as a targeting agent for the receptor for use in both diagnostics and therapeutics. In accordance with such embodiments, the active form need not confer upon any TIE expressing cell any change in phenotype.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE ligand-3 encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a TIE ligand-3 is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE ligand-3 gene product, for example, by binding of the ligand to TIE receptor or a portion thereof which may be tagged with, for example, a detectable antibody or portion thereof or by binding to antibodies produced against the TIE ligand-3 protein or a portion thereof. Cells of the present invention may transiently or, preferably, constitutively and permanently express TIE ligand-3 as described herein. In the fourth approach, DNA nucleotide primers can be prepared corresponding to a tie specific DNA sequence. These primers could then be used to PCR a tie gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein. Preferably, the ligand is secreted into the culture medium from which it is recovered. Alternatively, the ligand may be recovered from cells either as soluble proteins or as inclusion bodies, from which it may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

In additional embodiments of the invention, as described in greater detail in the Examples, a recombinant TIE ligand-3 encoding gene may be used to inactivate or "knock out" the endogenous gene by homologous recombination, and thereby create a TIE ligand-3 deficient cell, tissue, or animal. For example, and not by way of limitation, the recombinant TIE ligand-3 encoding gene may be engineered to contain an insertional mutation, for example the neo gene, which would inactivate the native TIE ligand-3 encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE ligand-3 encoding gene may then be identified, e.g. by Southern blotting, PCR detection, Northern blotting or assay of expression. Cells lacking an intact TIE ligand-3 encoding gene may then be fused to early embryo cells to generate transgenic animals deficient in such ligand. Such an animal may be used to define specific in vivo processes, normally dependent upon the ligand.

The present invention also provides for antibodies to TIE ligand-3 described herein which are useful for detection of the ligand in, for example, diagnostic applications. For preparation of monoclonal antibodies directed toward TIE ligand-3, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of TIE ligand-3 described herein. For the production of antibody, various host animals, including but not limited to rabbits, mice and rats can be immunized by injection with TIE ligand-3, or a fragment or derivative thereof. Various adjuvants may be used to increase the immunological response, including on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

A molecular clone of an antibody to a selected TIE ligand-3 epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of TIE ligand-3 in a biological sample by
a) contacting the biological sample with at least one antibody which specifically binds TIE ligand-3 so that the antibody forms a complex with any TIE ligand-3 present in the sample; and
b) measuring the amount of the complex and thereby measuring the amount of the TIE ligand-3 in the biological sample.

The invention further encompasses an assay for measuring the amount of TIE receptor in a biological sample by
a) contacting the biological sample with at least one ligand of the invention so that the ligand forms a complex with the TIE receptor; and
b) measuring the amount of the complex and thereby measuring the amount of the TIE receptor in the biological sample.

The present invention also provides for the utilization of TIE ligand-3 to support the survival and/or growth and/or migration and/or differentiation of TIE receptor expressing cells. Thus, the ligand may be used as a supplement to support, for example, endothelial cells in culture.

Further, the discovery by applicants of a cognate ligand for the TIE receptor enables the utilization of assay systems useful for the identification of agonists or antagonists of the TIE receptor. Such assay systems would be useful in identifying molecules capable of promoting or inhibiting angiogenesis. For example, in one embodiment, antagonists of the TIE receptor may be identified as test molecules that are capable of interfering with the interaction of the TIE receptor with biologically active TIE ligand-3. Such antagonists are identified by their ability to 1) block the binding of biologically active TIE ligand-3 to the receptor as measured, for example, using BIAcore biosensor technology (BIAcore; Pharmacia Biosensor, Piscataway, N.J.); or 2) block the ability of biologically active TIE ligand-3 to cause a biological response. Such biological responses include, but are not limited to, phosphorylation of the TIE receptor or downstream components of the TIE signal transduction pathway, or survival, growth or differentiation of TIE receptor bearing cells.

In one embodiment, cells engineered to express the TIE receptor may be dependent for growth on the addition of TIE ligand-3. Such cells provide useful assay systems for identifying additional agonists of the TIE receptor, or antagonists capable of interfering with the activity of TIE ligand-3 on such cells. Alternatively, autocrine cells, engineered to be capable of co-expressing both TIE ligand-3 and receptor, may provide useful systems for assaying potential agonists or antagonists.

Therefore, the present invention provides for introduction of a TIE receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of a TIE receptor (or a chimeric receptor comprising the extracellular domain of another receptor tyrosine kinase such as, for example, trkC and the intracellular domain of a TIE receptor) into a fibroblast cell line (e.g., NIH3T3 cells) thus such a receptor which does not normally mediate proliferative or other responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE ligand-3, thus creating an autocrine system useful for assaying for molecules that act as antagonists/agonists of this interaction. Thus, the present invention provides for host cells comprising nucleic acid encoding TIE ligand-3 and nucleic acid encoding TIE receptor.

The TIE receptor/TIE ligand-3 interaction also provides a useful system for identifying small molecule agonists or antagonists of the TIE receptor. For example, fragments, mutants or derivatives of TIE ligand-3 may be identified that bind TIE receptor but do not induce any other biological activity. Alternatively, the characterization of TIE ligand-3 enables the determination of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to TIE receptor may be measured in a number of ways. For example, the actual binding of test molecule to cells expressing TIE may be detected or measured, by detecting or measuring (i) test molecule bound to the surface of intact cells; (ii) test molecule cross-linked to TIE protein in cell lysates; or (iii) test molecule bound to TIE in vitro. The specific interaction between test molecule and TIE may be evaluated by using reagents that demonstrate the unique properties of that interaction.

As a specific, nonlimiting example, the methods of the invention may be used as follows. Consider a case in which the TIE ligand-3 in a sample is to be measured. Varying dilutions of the sample (the test molecule), in parallel with a negative control (NC) containing no TIE ligand-3 activity, and a positive control (PC) containing a known amount of a TIE ligand-3, may be exposed to cells that express TIE in the presence of a detectably labeled TIE ligand-3 (in this example, radioiodinated ligand). The amount of TIE ligand-3 in the test sample may be evaluated by determining the amount of $^{125}$I-labeled TIE ligand-3 that binds to the controls and in each of the dilutions, and then comparing the sample values to a standard curve. The more TIE ligand-3 in the sample, the less $^{125}$I-ligand that will bind to TIE.

The amount of $^{125}$I-ligand bound may be determined by measuring the amount of radioactivity per cell, or by cross-linking the TIE ligand-3 to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE receptor/TIE ligand-3. The specific test molecule/TIE interaction may further be tested by adding to the assays various dilutions of an unlabeled control ligand that does not bind the TIE receptor and therefore should have no substantial effect on the competition between labeled TIE ligand-3 and test molecule for TIE binding. Alternatively, a molecule known to be able to disrupt TIE receptor/TIE ligand-3 binding, such as, but not limited to, anti-TIE antibody, or TIE receptorbody as described herein, may be expected to interfere with the competition between $^{125}$I-TIE ligand-3 and test molecule for TIE receptor binding.

Detectably labeled TIE ligand-3 includes, but is not limited to, TIE ligand-3 linked covalently or noncovalently to a radioactive substance, a fluorescent substance, a substance that has enzymatic activity, a substance that may serve as a substrate for an enzyme (enzymes and substrates associated with colorimetrically detectable reactions are preferred) or to a substance that can be recognized by an antibody molecule that is preferably a detectably labeled antibody molecule.

Alternatively, the specific binding of test molecule to TIE may be measured by evaluating the secondary biological effects of TIE ligand-3/TIE receptor binding, including, but not limited to, cell growth and/or differentiation or immediate early gene expression or phosphorylation of TIE. For example, the ability of the test molecule to induce differentiation can be tested in cells that lack tie and in comparable cells that express tie; differentiation in tie-expressing cells but not in comparable cells that lack tie would be indicative of a specific test molecule/TIE interaction. A similar analysis could be performed by detecting immediate early gene (e.g. fos and jun) induction in tie-minus and tie-plus cells, or by detecting phosphorylation of TIE using standard phosphorylation assays known in the art. Such analysis might be useful in identifying agonists or antagonists that do not competitively bind to TIE.

Similarly, the present invention provides for a method of identifying a molecule that has the biological activity of TIE ligand-3 comprising (i) exposing a cell that expresses tie to a test molecule and (ii) detecting the specific binding of the test molecule to TIE receptor, in which specific binding to TIE positively correlates with TIE-like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-minus or engineered to be tie-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE ligand-like activity or identifying a molecule as having such activity comprising (i) exposing a test molecule to a TIE receptor protein in vitro under conditions that permit binding to occur and (ii) detecting binding of the test molecule to the TIE receptor protein, in which binding of test molecule to TIE receptor correlates with TIE ligand-like activity. According to such methods, the TIE receptor may or may not be substantially purified, may be affixed to a solid support (e.g. as an affinity column or as an ELISA assay), or may be incorporated into an artificial membrane. Binding of test molecule to TIE receptor may be evaluated by any method known in the art. In preferred embodiments, the binding of test molecule may be detected or measured by evaluating its ability to compete with detectably labeled known TIE ligands for TIE receptor binding.

The present invention also provides for a method of detecting the ability of a test molecule to function as an antagonist of TIE ligand-like activity comprising detecting the ability of the molecule to inhibit an effect of TIE ligand binding to TIE receptor on a cell that expresses the receptor. Such an antagonist may or may not interfere with TIE receptor/TIE ligand-3 binding. Effects of TIE ligand-3 binding to TIE receptor are preferably biological or biochemical effects, including, but not limited to, cell survival or proliferation, cell transformation, immediate early gene induction, or TIE phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of TIE ligand-3 which has been Myc-tagged may then be introduced to the well and any tagged TIE ligand-3 which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or TIE ligand-3 or ligandbody is covalently attached to a solid support (e.g. carboxymethyl dextran on a gold surface), one of skill in the art would be able to determine if the blocker molecule is binding specifically to the ligand, ligandbody or to the receptorbody. To determine if the blocker molecule can neutralize the biological activity of the ligand, one of skill in the art could perform a phosphorylation assay (see Example 5) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE receptor.

In addition, the invention further contemplates compositions wherein the TIE ligand is the receptor binding domain of the TIE ligand-3 described herein. For example, TIE-2 ligand 1 consists of a "coiled coil" domain (beginning at the 5' end and extending to the nucleotide at about position 1160 of FIGS. 4A and 4B (SEQ. ID NO.1) and about position 1157 of FIGS. 5A and 5B (SEQ. ID NO.3)) and a fibrinogen-like domain (which is encoded by the nucleotide sequence of FIGS. 4A and 4B (SEQ. ID NO.1) beginning at about position 1161 and about position 1158 of FIGS. 5A and 5B (SEQ. ID NO.3)). The fibrinogen-like domain of TIE-2 ligand 2 is believed to begin on or around the same amino acid sequence as in ligand 1 (FRDCA) which is encoded by nucleotides beginning around 1197 of FIGS. 6A and 6B (SEQ. ID NO.5). The fibrinogen-like domain of TIE ligand-3 is believed to begin on or around the amino acid sequence which is encoded by nucleotides beginning around position 929 as set forth in FIGS. 21A and 21B (SEQ. ID NO.7). Multimerization of the coiled coil domains during production of the ligand hampers purification. As described in Example 19, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor. [Methods of production of "clustered ligands and ligandbodies are described in Davis, et al. Science 266:816–819 (1994)). Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of TIE ligand-3 ligandbodies which may be used as targeting agents, in diagnostics or in therapeutic applications, such as targeting agents for tumors and/or associated vasculature wherein a TIE antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE receptor. Such molecules may be used in a method of treatment of the human or animal body, or in a method of diagnosis.

Because TIE receptor has been identified in association with endothelial cells and, as demonstrated herein, blocking of TIE-2 ligand 1 appears to prevent vascularization, applicants expect that the TIE ligand-3 may be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic.

Ferrara, et al. U.S. Pat. No. 5,332,671 issued Jul. 26, 1994. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al. European Patent Application 0 550 296 A2 published Jul. 7, 1993; Banai, et al. Circulation 89:2183–2189 (1994); Unger, et al. Am. J. Physiol. 266:H1588–H1595 (1994); Lazarous, et al. Circulation 91:145–153 (1995)]. According to the invention, TIE ligand-3 may be used alone or in combination with one or more additional pharmaceutically active compounds such as, for example, VEGF or basic fibroblast growth factor (bFGF), as well as cytokines, neurotrophins, etc.

Conversely, antagonists of the TIE receptor, such as receptorbodies as described herein in Examples 2 and 3, and TIE-2 ligand 2 as described in Example 9, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. Applicants expect that the TIE ligand-3 described herein may also be used in combination with agents, such as cytokine antagonists such as IL-6 antagonists, that are known to block inflammation.

For example, applicants have determined that TIE ligands are expressed in cells within, or closely associated with, tumors. For example, TIE-2 ligand 2 appears to be tightly associated with tumor endothelial cells. Accordingly, it and other TIE antagonists may also be useful in preventing or attenuating, for example, tumor growth. In addition, TIE ligands or ligandbodies may be useful for the delivery of toxins to a receptor bearing cell. Alternatively, other molecules, such as growth factors, cytokines or nutrients, may be delivered to a TIE receptor bearing cell via TIE ligands or ligandbodies. TIE ligands or ligandbodies such as TIE ligand-3 may also be used as diagnostic reagents for TIE receptor, to detect the receptor in vivo or in vitro. Where the TIE receptor is associated with a disease state, TIE ligands or ligandbodies such as TIE ligand-3 may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 published Oct. 5, 1995 and Burrows, F. and P. Thorpe, PNAS (USA) 90:8996–9000 (1993) which is incorporated herein in its entirety.

In other embodiments, the TIE ligands, such as TIE ligand-3, described herein are used as hematopoietic factors. A variety of hematopoietic factors and their receptors are involved in the proliferation and/or differentiation and/or migration of the various cells types contained within blood. Because the TIE receptors are expressed in early hematopoietic cells, the TIE ligands are expected to play a comparable role in the proliferation or differentiation or migration of these cells. Thus, for example, TIE containing compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. NatI. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly, TIE ligand-3 may be used to diagnose or treat conditions in which normal hematopoiesis is suppressed, including, but not limited to anemia, thrombocytopenia, leukopenia and granulocytopenia. In a preferred embodiment, TIE ligand-3 may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The TIE ligand-3 of the present invention may be used alone, or in combination with another pharmaceutically active agent such as, for example, ctyokines, neurotrophins, interleukins, etc. In a preferred embodiment, the ligand may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE receptor antagonists are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the TIE ligand-3, TIE antibody, TIE receptorbody, a conjugate of TIE ligand-3, or a ligandbody or fFC as described herein.

The present invention also provides for pharmaceutical compositions comprising the TIE ligand-3 or ligandbodies described herein, peptide fragments thereof, or derivatives in a pharmacologically acceptable vehicle. The TIE ligand-3 proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a TIE ligand-3 or ligandbody and a cytotoxic agent conjugated thereto. In one embodiment, the cytotoxic agent may be a radioisotope or toxin.

The invention also provides for an antibody which specifically binds a TIE ligand-3. The antibody may be monoclonal or polyclonal.

The invention further provides for a method of purifying TIE ligand-3 comprising:

a) coupling at least one TIE binding substrate to a solid matrix;

b) incubating the substrate of a) with a cell lysate so that the substrate forms a complex with any TIE ligand-3 in the cell lysate;

c) washing the solid matrix; and d) eluting the TIE ligand-3 from the coupled substrate.

The substrate may be any substance that specifically binds the TIE ligand-3. In one embodiment, the substrate is selected from the group consisting of anti-TIE ligand-3 antibody, TIE receptor and TIE receptorbody. The invention further provides for a receptorbody which specifically binds TIE ligand-3, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising TIE ligand-3 or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE receptor which comprises contacting a cell with a detectably labeled TIE ligand-3 or ligandbody, under conditions permitting binding of the detectably labeled ligand to the TIE receptor and determining whether the detectably labeled ligand is bound to the TIE receptor, thereby identifying the cell as one which expresses TIE receptor. The present invention also provides for a therapeutic composition comprising a TIE ligand-3 or ligandbody and a cytotoxic agent conjugated thereto. The cytotoxic agent may be a radioisotope or toxin.

The invention also provides a method of detecting expression of TIE ligand-3 by a cell which comprises obtaining mRNA from the cell, contacting the mRNA so obtained with a labeled nucleic acid molecule encoding TIE ligand-3, under hybridizing conditions, determining the presence of mRNA hybridized to the labeled molecule, and thereby detecting the expression of the TIE ligand-3 in the cell.

The invention further provides a method of detecting expression of TIE ligand-3 in tissue sections which comprises contacting the tissue sections with a labeled nucleic acid molecule encoding a TIE ligand-3, under hybridizing conditions, determining the presence of mRNA hybridized to the labelled molecule, and thereby detecting the expression of TIE ligand-3 in tissue sections.

EXAMPLE 1

IDENTIFICATION OF THE ABAE CELL LINE AS REPORTER CELLS FOR THE TIE-2 RECEPTOR

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at $14,000 \times G$ for 10 minutes, at 40° C. and the supernatants were subjected to immunoprecipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

CLONING AND EXPRESSION OF TIE-2 RECEPTORBODY FOR AFFINITY-BASED STUDY OF TIE-2 LIGAND INTERACTIONS

An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1-4 may be used. DNA encoding the TIE-2 RB was cloned as an Eco RI-NotI fragment into the baculovirus transfer plasmid pVL1393. Plasmid DNA purified by cesium chloride density gradient centrifugation was recombined into viral DNA by mixing 3 µg of plasmid DNA with 0.5 µg of Baculo-Gold DNA (Pharminigen), followed by introduction into liposomes using 30 µg Lipofectin (GIBCO-BRL). DNA- liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 µg/mL X-gal (5-bromo-4-chloro-3-indolyl-µ-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 µg/mL MTT (3-[4,5-dimethylthiazol-2-yl]2, 5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1×antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~$2 \times 10^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5M NaCI until the absorbance at 280 nm decreased to baseline. The column was washed in PBS and eluted with 0.5M acetic acid. Column fractions were immediately neutralized by eluting into tubes containing 1M Tris pH 9. The peak fractions containing the TIE-2 receptorbody were pooled and dialyzed versus PBS.

EXAMPLE 3

DEMONSTRATION THAT TIE-2 HAS A CRITICAL ROLE IN DEVELOPMENT OF THE VASCULATURE

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Figure 1B:
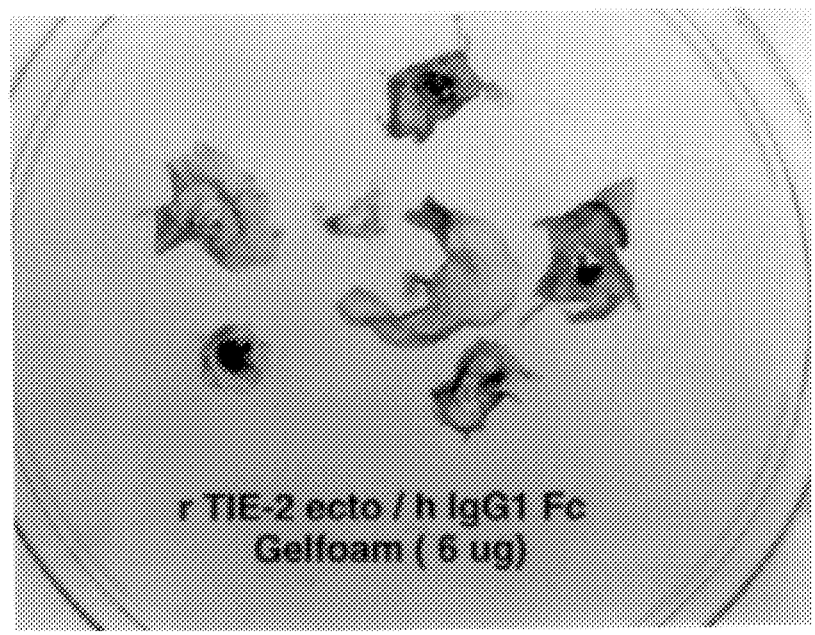

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

IDENTIFICATION OF A TIE-2-SPECIFIC BINDING ACTIVITY IN CONDITIONED MEDIUM FROM THE ras ONCOGENE-TRANSFORMED C2C12 MOUSE MYOBLAST CELL LINE Screening of ten-fold-concentrated cell-conditioned media (10× CCM) from various cell lines for the presence of soluble, TIE-2-specific binding activity (BIAcore; Pharmacia Biosensor, Piscataway, N.J.) revealed binding activity in serum-free medium from oncogenic-ras-transformed C2C12 cells (C2C12-ras), RAT 2-ras (which is a ras transformed fibroblast cell line), human glioblastoma T98G and the human neuroblastoma cell line known as SHEP-1.

The C2C12-ras 10× CCM originated from a stably transfected line of C2C12 myoblasts that was oncogenically transformed by transfection with the T-24 mutant of H-ras by standard calcium phosphate-based methods. An SV40 based neomycin-resistance expression plasmid was physically linked with the ras expression plasmid in order to permit selection of transfected clones. Resulting G418-resistant ras-C2C12 cells were routinely maintained as a monolayer on plastic dishes in DMEM/glutamine/penicillin-streptomycin supplemented with 10% fetal calf serum (FCS). Serum-free C2C12-ras 10×CCM was made by plating the cells at 60% confluence in a serum free defined media for 12 hours. [Zhan and Goldfarb, Mol. Cell. Biol. 6: 3541–3544 (1986)); Zhan, et al. Oncogene 1: 369–376 (1987)]. The medium was discarded and replaced with fresh DMEM/Q/P-S for 24 hours. This medium was harvested and cells were re-fed fresh DMEM/Q/P-S, which was also harvested after a further 24 hours. These CCM were supplemented with the protease inhibitors PMSF (1 mM) and aprotinin (10 μg/ml), and ten-fold concentrated on sterile size-exclusion membranes (Amicon). TIE-2-binding activity could be neutralized by incubation of the medium with an excess of TIE-2 RB, but not by incubation with EHK-1 RB, prior to BIAcore analysis.

Binding activity of the 10×CCM was measured using biosensor technology (BIAcore; Pharmacia Biosensor, Piscataway, N.J.) which monitors biomolecular interactions in real-time via surface plasmon resonance. Purified TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 μg/mL, pH 4.5) and deactivation of unreacted sites with 1.0M ethanolamine (pH 8.5). A negative control surface of the EHK-1 receptorbody was prepared in a similar manner.

The running buffer used in the system was HBS (10 mM Hepes, 3.4 mM EDTA, 150 mM NaCI, 0.005% P20 surfactant, pH 7.4). The 10×CCM samples were centrifuged for 15 min at 4° C. and further clarified using a sterile, low protein-binding 0.45 μm filter (Millipore; Bedford, Mass.). Dextran (2 mg/ml) and P20 surfactant (0.005%) were added to each CCM sample. Aliquots of 40, μL were injected across the immobilized surface (either TIE-2 or EHK-1) at a flow rate of 5 μL/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 12 μL pulse of 3M $MgCl_2$.

The instrument noise level is 20 RU; therefore, any binding activity with a signal above 20 RU may be interpreted as a real interaction with the receptor. For C2C12-ras conditioned media, the binding activities were in the range 60–90 RU for the TIE-2 RB immobilized surface. For the same samples assayed on a EHK-1 RB immobilized surface, the measured activities were less than 35 RU. Specific binding to the TIE-2 receptorbody was evaluated by incubating the samples with an excess of either soluble TIE-2 or EHK-1 RB prior to assaying the binding activity. The addition of soluble EHK-1 RB had no effect on the TIE-2 binding activity of any of the samples, while in the presence of soluble TIE-2 binding to the surface is two-thirds less than that measured in the absence of TIE-2. A repeat assay using >50× concentrated C2C12-ras CCM resulted in a four-fold enhancement over background of the TIE-2 specific binding signal.

EXAMPLE 5

C2C12-ras CCM CONTAINS AN ACTIVITY THAT INDUCES TYROSINE PHOSPHORYLATION OF TIE-2 RECEPTOR C2C12-ras 10×CCM was examined for its ability to induce tyrosine phosphorylation of TIE-2 in ABAE cells. Serum-starved ABAE cells were briefly incubated with C2C12-ras CCM, lysed and subjected to immunoprecipitation and Western analyses as described above. Stimulation of serum-starved ABAE cells with serum-free C2C12-ras 10×CCM was done as follows. The medium of ABAE cells starved as described above was removed and replaced with either defined medium or 10×CCM that had been pre-warmed to 37° C. After 10 minutes, the media were removed and the cells were twice rinsed on ice with an excess of chilled PBS supplemented with orthovanadate/NaF/benzamidine. Cell lysis and TIE-2-specific immunoprecipitation was done as described above.

ABAE cells incubated for 10 minutes with defined medium showed no induction of TIE-2 tyrosine phosphorylation, whereas incubation with C2C12-ras CCM stimulated at least a 100× increase in TIE-2 phosphorylation. This activity was almost totally depleted by pre-incubation of the C2C12-ras 10×CCM for 90 minutes at room temperature with 13 μg of TIE-2 RB coupled to protein G-Sepharose beads. Medium incubated with protein G Sepharose alone was not depleted of this phosphorylating activity.

EXAMPLE 6

EXPRESSION CLONING OF TIE-2 LIGAND

Figure 2:
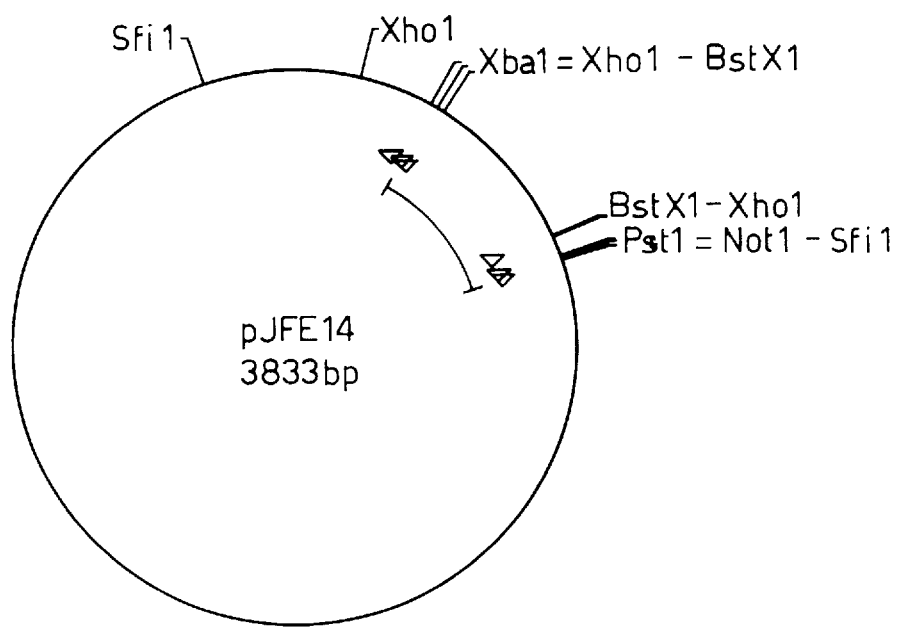
FIG. 2—Vector pJFE14.

COS-7 cells were cultured in Dulbecco's modified Eagle's medium (DMEM) containing 10% fetal bovine serum (FBS), 1% each of penicillin and streptomycin (P/S) and 2 mM glutamine in an atmosphere of 5% $CO_2$. The mouse myoblast C2C12 ras cell line was cultured in Eagle's minimal essential medium (EMEM) with 10% FBS, (P/S) and 2 mM glutamine. Full length mouse TIE-2 ligand cDNA clones were obtained by screening a C2C12 ras cDNA library in the pJFE14 vector expressed in COS cells. This vector, as shown in FIG. 2, is a modified version of the vector $pSR_\alpha$ (Takebe, et al. 1988, Mol. Cell. Biol. 8:466–472). The library was created using the two BSTX1 restriction sites in the pJFE14 vector.

COS-7 cells were transiently transfected with either the pJFE14 library or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with PBS with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Two days after transfection the cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody (RB), which consisted of the extracellular domain of TIE-2 fused to the IgG1 constant region. This receptorbody was prepared as set forth in Example 2. A 100 mm dish of transfected, fixed and permeabilized COS cells was probed by incubating them for 30 min with TIE-2 RB. The cells were then washed twice with PBS and incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. For each stained cell, a small area of cells including the stained cell was scraped from the dish using a plastic pipette tip and plasmid DNA was then rescued and used to electroporate bacterial cells. Single bacterial colonies resulting from the electroporation were picked and plasmid DNA prepared from these colonies was used to transfect COS-7 cells which were probed for TIE-2 ligand expression as evidenced by binding to TIE-2 receptorbodies. This allowed identification of single clones coding for TIE-2 ligand. Confirmation of TIE-2 ligand expression was obtained by phosphorylation of the TIE-2 receptor using the method set forth in Example 5. A plasmid clone encoding the TIE-2 ligand was deposited with the ATCC on Oct. 7, 1994 and designated as "pJFE14 encoding TIE-2 ligand" under ATCC Accession No. 75910.

EXAMPLE 7

ISOLATION AND SEQUENCING OF FULL LENGTH cDNA CLONE ENCODING HUMAN TIE-2 LIGAND

Figure 3:
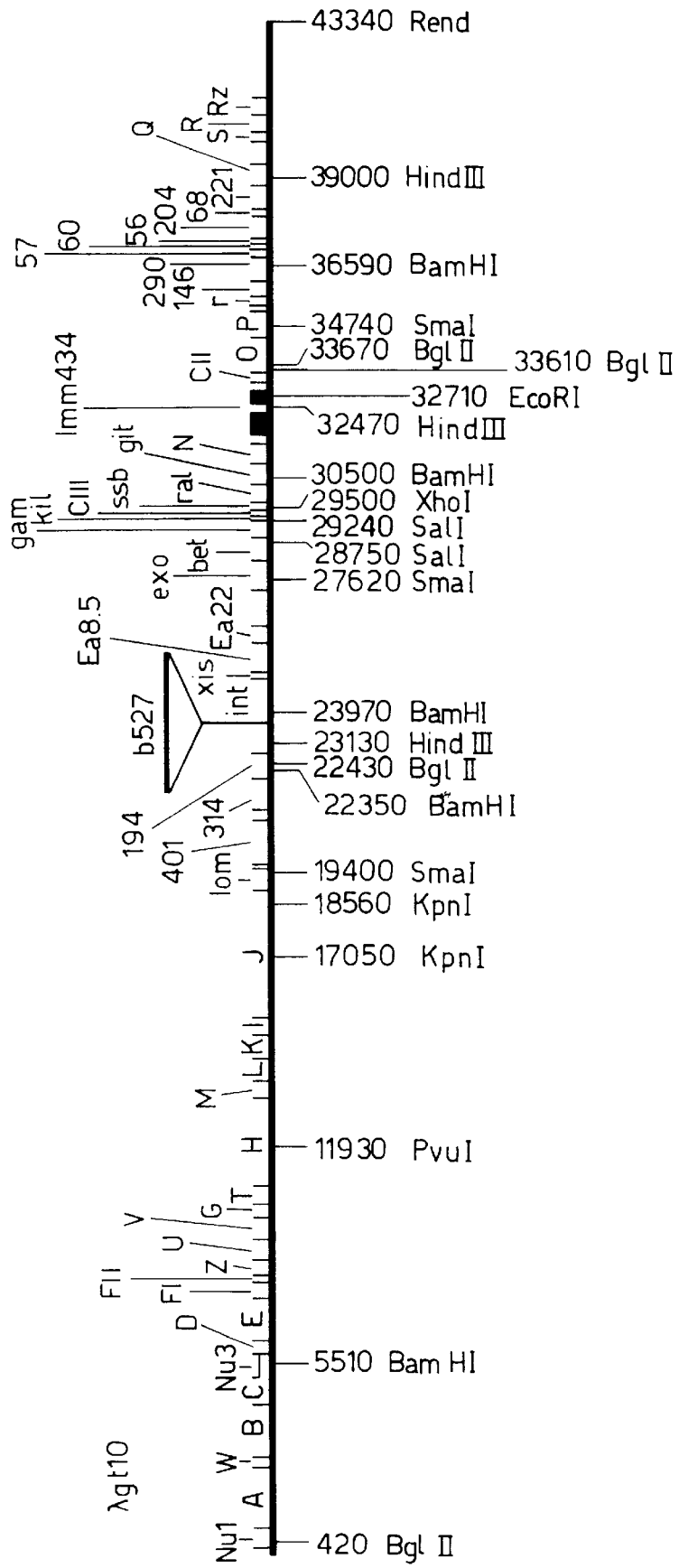
FIG. 3—Restriction map of λgt 10.

A human fetal lung cDNA library in lambda gt-10 (see FIG. 3) was obtained from Clontech Laboratories, Inc. (Palo Alto, Calif.). Plaques were plated at a density of $1.25 \times 10^6$/ 20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.).

Isolation of human tie-2 ligand clones was carried out as follows. A 2.2 kb XhoI fragment from the deposited tie-2 ligand clone (ATCC NO. 75910 - see Example 6 above) was labeled by random priming to a specific activity of approximately $5 \times 10^8$ cpm/ng. Hybridization was carried out at 65° C. in hybridization solution containing 0.5 mg/ml salmon sperm DNA. The filters were washed at 65° C. in 2×SSC, 0.1% SDS and exposed to Kodak XAR-5 film overnight at −70° C. Positive phage were plaque purified. High titre phage lysates of pure phage were used for isolation of DNA via a Qiagen column using standard techniques (Qiagen, Inc., Chatsworth, Calif., 1995 catalog, page 36). Phage DNA was digested with EcoRI to release the cloned cDNA fragment for subsequent subcloning. A lambda phage vector containing human tie-2 ligand DNA was deposited with the ATCC on Oct. 26, 1994 under the designation λgt10 encoding htie-2 ligand 1 (ATCC Accession No. 75928). Phage DNA may be subjected directly to DNA sequence analysis by the dideoxy chain termination method (Sanger, et al., 1977, Proc. Natl. Acad. Sci. U.S.A. 74: 5463–5467).

Subcloning of the human tie-2 ligand DNA into a mammalian expression vector may be accomplished as follows. The clone λgt10 encoding htie-2 ligand 1 contains an EcoRI site located 490 base pairs downstream from the start of the coding sequence for the human TIE-2 ligand. The coding region may be excised using unique restriction sites upstream and downstream of the initiator and stop codons respectively. For example, an SpeI site, located 70 bp 5' to the initiator codon, and a Bpu1102i (also known as BlpI) site, located 265 bp 3' to the stop codon, may be used to excise the complete coding region. This may then be subcloned into the pJFE14 cloning vector, using the XbaI (compatible to the SpeI overhang) and the PstI sites (the PstI and Bpu1102i sites are both made blunt ended).

The coding region from the clone λgt10 encoding htie-2 ligand 1 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone λgt10 encoding htie-2 ligand 1 is shown in FIGS. 4A and 4B (SEQ. ID NOS.1&2).

In addition, full length human tie-2 ligand cDNA clones were obtained by screening a human glioblastoma T98G cDNA library in the pJFE14 vector. Clones encoding human TIE-2 ligand were identified by DNA hybridization using a 2.2 kb XhoI fragment from the deposited tie-2 ligand clone (ATCC NO. 75910) as a probe (see Example 6 above). The coding region was sequenced using the ABI 373A DNA sequencer and Taq Dideoxy Terminator Cycle Sequencing Kit (Applied Biosystems, Inc., Foster City, Calif.). This sequence was nearly identical to that of clone λgt10 encoding htie-2 ligand 1. As shown in FIGS. 4A and 4B (SEQ. ID NOS.1&2), the clone kgt10 encoding htie-2 ligand 1 contains an additional glycine residue which is encoded by nucleotides 1114–1116. The coding sequence of the T98G clone does not contain this glycine residue but otherwise is identical to the coding sequence of the clone λgt10 encoding htie-2 ligand 1. FIGS. 5A and 5B (SEQ. ID NOS.3&4) sets forth the nucleotide and deduced amino acid sequence of human TIE-2 ligand from the T98G clone.

EXAMPLE 8

ISOLATION AND SEQUENCING OF SECOND FULL LENGTH cDNA CLONE A ENCODING HUMAN TIE-2 LIGAND

A human fetal lung cDNA library in lambda gt-10 (see FIG. 3) was obtained from Clontech Laboratories, Inc. (Palo Alto, Calif.). Plaques were plated at a density of $1.25 \times 10^6$/ 20×20 cm plate, and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at low stringency (2×SSC, 55° C.) with probes made to the human TIE-2 ligand 1 sequence. One of the duplicate filters was probed with a 5' probe, encoding amino acids 25–265 of human TIE-2 ligand 1 as set forth in FIGS. 4A and 4B (SEQ. ID NOS.1&2). The second duplicate filter was probed with a 3' probe, encoding amino acids 282–498 of human TIE-2 ligand 1 sequence (see FIGS. 4A and 4B (SEQ. ID NOS.1&2)). Both probes were hybridized at 55° C. in hybridization solution containing 0.5 mg/ml salmon sperm DNA. Filters were washed in 2×SSC at 55° C. and exposed overnight to X-ray film. In addition, duplicate filters were also hybridized at normal stringency (2×SSC, 65° C.) to the full length coding probe of mouse TIE-2 ligand 1 (F3-15, XhoI insert). Three positive clones were picked that fulfilled the following criteria: i. hybridization had not been seen to the full length (mouse) probe at normal stringency, and ii. hybridization was seen at low stringency to both 5' and 3' probes. EcoRI digestion of phage DNA obtained from these clones indicated two independent clones with insert sizes of approximately 2.2 kb and approximately 1.8 kb. The 2.2 kb EcoRI insert was subcloned into the EcoRI sites of both pBluescript KS (Stratagene) and a mammalian expression vector suitable for use in COS cells. Two orientations were identified for the mammalian expression vector. The 2.2 kb insert in pBluescript KS was deposited with the ATCC on December 9, 1994 and designated as pBluescript KS encoding human TIE 2 ligand 2. The start site of the TIE-2 ligand 2 coding sequence is approximately 355 base pairs downstream of the pBluescript EcoRi site.

COS-7 cells were transiently transfected with either the expression vector or control vector by the DEAE-dextran transfection protocol. Briefly, COS-7 cells were plated at a density of $1.0 \times 10^6$ cells/100 mm plate 24 hours prior to transfection. For transfection, the cells were cultured in serum-free DMEM containing 400 μg/ml of DEAE-dextran, 1 μM chloroquine, and 2 mM glutamine, and 1 μg of the appropriate DNA for 3–4 hours at 37° C. in an atmosphere of 5% $CO_2$. The transfection media was aspirated and replaced with phosphate-buffered saline with 10% DMSO for 2–3 min. Following this DMSO "shock", the COS-7 cells were placed into DMEM with 10% FBS, 1% each of penicillin and streptomycin, and 2 mM glutamine for 48 hours.

Because the TIE-2 ligand is secreted it was necessary to permeabilize the cells to detect binding of the receptorbody probe to the ligand. Transfected COS-7 cells were plated at a density of $1.0 \times 10^6$ cells/100 mm plate. The cells were rinsed with PBS and then incubated with PBS containing 1.8% formaldehyde for 15–30 min. at room temperature. Cells were then washed with PBS and incubated for 15 min. with PBS containing 0.1% Triton X-100 and 10% Bovine Calf Serum to permeabilize the cells and block non-specific binding sites.

The screening was conducted by direct localization of staining using a TIE-2 receptorbody, which consisted of the extracellular domain of TIE-2 fused to the IgG1 constant region. This receptorbody was prepared as set forth in Example 2. Transfected COS cells were probed by incubating them for 30 min with TIE-2 receptorbody. The cells were then washed twice with PBS, fixed with methanol, and then incubated for an additional 30 min with PBS/10% Bovine Calf Serum/anti-human IgG-alkaline phosphatase conjugate. After three PBS washes, cells were incubated in alkaline-phosphatase substrate for 30–60 min. The dish was then inspected microscopically for the presence of stained cells. Cells expressing one orientation of the clone, but not the other orientation, were seen to bind the TIE-2 receptorbody.

One of skill in the art will readily see that the described methods may be used to further identify other related members of the TIE ligand family.

The coding region from the clone pBluescript KS encoding human TIE- 2 ligand 2 was sequenced using the ABI 373A DNA sequencer and Taq Dideoxy Terminator Cycle Sequencing Kit (Applied Biosystems, Inc., Foster City, Calif.). The nucleotide and deduced amino acid sequence of human TIE-2 ligand from the clone pBluescript KS encoding human TIE-2 ligand 2 is shown in FIGS. 6A and 6B (SEQ. ID NOS.5&6).

EXAMPLE 9

TIE-2 LIGAND 2 IS A RECEPTOR ANTAGONIST

Conditioned media from COS cells expressing either TIE-2 ligand 2 (TL2) or TIE-2 ligand 1 (TL1) were compared for their ability to activate TIE-2 receptors naturally present in human endothelial cell lines.

Lipofectamine reagent (GIBCO-BRL, Inc.) and recommended protocols were used to transfect COS-7 cells with either the pJFE14 expression vector alone, pJFE14 vector containing the human TIE-2 ligand 1 cDNA, or with a pMT21 expression vector (Kaufman, R. J., 1985, Proc. Natl. Acad. Sci. USA 82: 689–693) containing the human TIE-2 ligand 2 CDNA. COS media containing secreted ligands were harvested after three days and concentrated 20-fold by diafiltration (DIAFLO ultrafiltration membranes, Amicon, Inc.). The quantity of active TIE-2 ligand 1 and TIE-2 ligand 2 present in these media was determined and expressed as the amount (in resonance units, R.U.) of TIE-2 receptor specific binding activity measured by a BIAcore binding assay.

Figure 7:
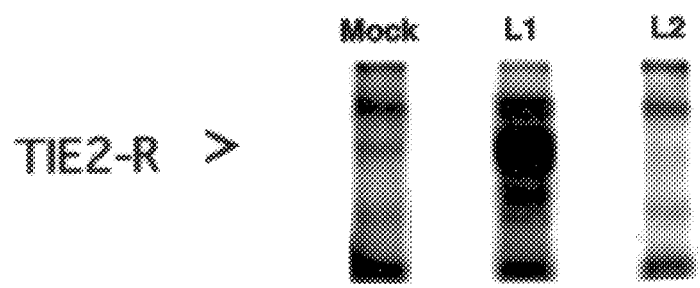
FIG. 7—Western blot showing activation of TIE-2 receptor by TIE-2 ligand 1 (Lane L1) but not by TIE-2 ligand 2 (Lane L2) or control (Mock).

Northern (RNA) analyses revealed significant levels of TIE-2 transcripts in HAEC (Human Aortic Endothelial Cell) human primary endothelial cells (Clonetics, Inc.). Therefore, these cells were used to examine whether TIE-2 receptor is tyrosine-phosphorylated when exposed to COS media containing the TIE-2 ligands. HAEC cells were maintained in a complete endothelial cell growth medium (Clonetics, Inc.) that contained 5% fetal bovine serum, soluble bovine brain extract, 10 ng/ml human EGF, 1 mg/ml hydrocortisone, 50 mg/ml gentamicin and 50 ng/ml amphotericin-B. Assessment of whether TL1 and TL2 could activate TIE-2 receptor in the HAEC cells was done as follows. Semi-confluent HAEC cells were serum-starved for two hours in high-glucose Dulbecco's MEM with added L-glutamine and penicillin-streptomycin at 37° C. followed by replacement of the starvation medium with ligand-containing conditioned COS media for 7 minutes at 37° C. in a 5% CO2 incubator. The cells were subsequently lysed and TIE-2 receptor protein was recovered by immunoprecipitation of the lysates with TIE-2 peptide antiserum, followed by Western blotting with antiphosphotyrosine antiserum, exactly as described in example 1. The results are shown in FIG. 7. Phosphotyrosine levels on the TIE-2 receptor (TIE-2-R) were induced by treatment of HEAC cells with TIE-2 ligand 1 (Lane L1) but not by TIE-2 ligand 2 (Lane L2) conditioned COS media. MOCK is conditioned media from COS transfected with JFE14 empty vector.

Evidence that both TL1 and TL2 specifically bind to the TIE-2 receptor was demonstrated by using a BIAcore to assay the TIE-2 receptor specific binding activities in transfected COS media and by immunostaining of TL1- and TL2-expressing COS cells with TIE-2 receptorbodies.

Because TL2 did not activate the TIE-2 receptor, applicants set out to determine whether TL2 might be capable of serving as an antagonist of TL1 activity. HAEC phosphorylation assays were performed in which cells were first incubated with an "excess" of TL2, followed by addition of dilute TL1. It was reasoned that prior occupancy of TIE-2 receptor due to high levels of TL2 might prevent subsequent stimulation of the receptor following exposure to TL1 present at a limiting concentration.

Figure 8:
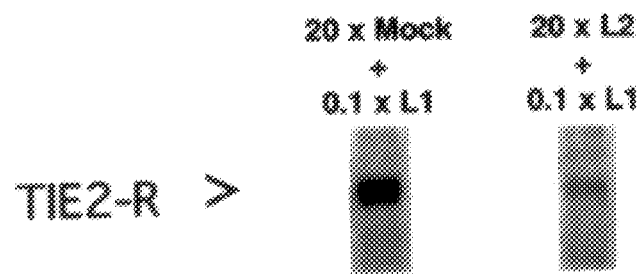
FIG. 8—Western blot showing that prior treatment of HAEC cells with excess TIE-2 ligand 2 (Lane 2) antagonizes the subsequent ability of dilute TIE-2 ligand 1 to activate the TIE-2 receptor (TIE2-R) as compared with prior treatment of HAEC cells with MOCK medium (Lane 1).

Semi-confluent HAEC cells were serum-starved as described above and then incubated for 3 min., at 37° C. with 1–2 ml. of 20×COS/JFE14-TL2 conditioned medium. Control plates were treated with 20×COS/JFE14-only medium (MOCK). The plates were removed from the incubator and various dilutions of COS/JFE14-TL1 medium were then added, followed by further incubation of the plates for 5–7 min. at 37° C. Cells were subsequently rinsed, lysed and TIE-2-specific tyrosine phosphorylation in the lysates was examined by receptor immunoprecipitation and Western blotting, as described above. TL1 dilutions were made using 20×COS/JFE14-TL1 medium diluted to 2×, 0.5×, 0.1×, or 0.02× by addition of 20×COS/JFE14-alone medium. An assay of the initial 20×TL1 and 20× TL2 COS media using BIAcore biosensor technology indicated that they contained similar amounts of TIE-2-specific binding activities, i.e., 445 R.U. and 511 R.U. for TL1 and TL2, respectively. The results of the antiphosphotyrosine Western blot, shown in FIG. 8, indicate that when compared to prior treatment of HAEC cells with MOCK medium (lane 1), prior treatment of HAEC cells with excess TIE-2 ligand 2 (lane 2) antagonizes the subsequent ability of dilute TIE-2 ligand 1 to activate the TIE-2 receptor (TIE-2-R).

Figure 9:
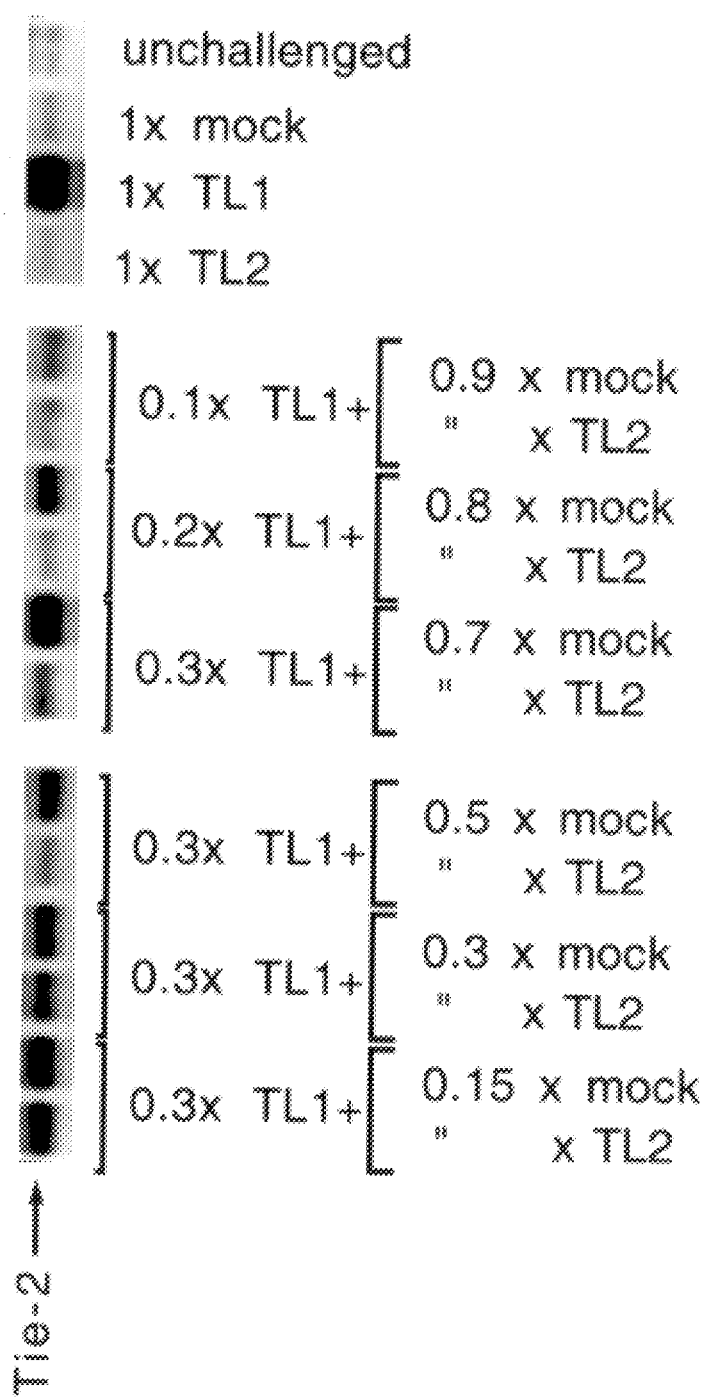
FIG. 9—Western blot demonstrating the ability of TL2 to competitively inhibit TL1 activation of the TIE-2 receptor using the human cell hybrid line, EA.hy926.
Figure 10A:
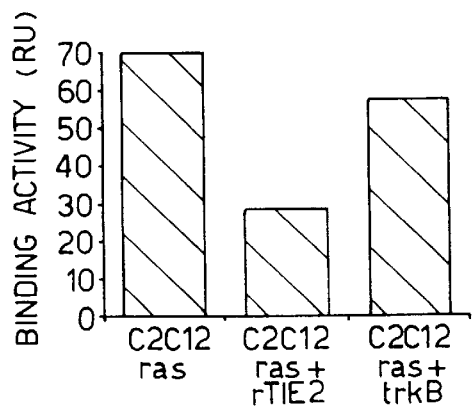
FIG. 10A and 10D—Histogram representation of binding to rat TIE-2 IgG immobilized surface by TIE-2 ligand in C2C12 ras (FIG. 10A), Rat2 ras (FIG. 10B), SHEP (FIG. 10C), and T98G (FIG. 10D) concentrated (10×) conditioned medium. Rat TIE-2 (rTIE2) specific binding is demonstrated by the significant reduction in the binding activity in the presence of 25 μg/ml soluble rat TIE-2 RB as compared to a minor reduction in the presence of soluble trkB RB.
Figure 10B:
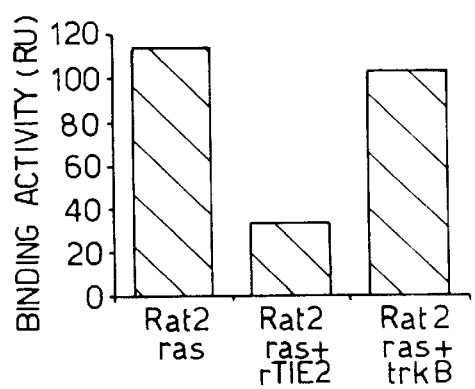
Figure 10C:
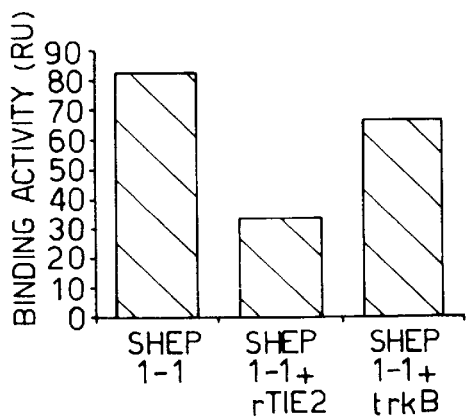
Figure 10D:
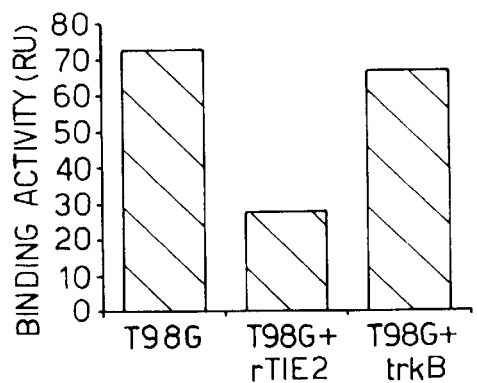
Figure 11A:
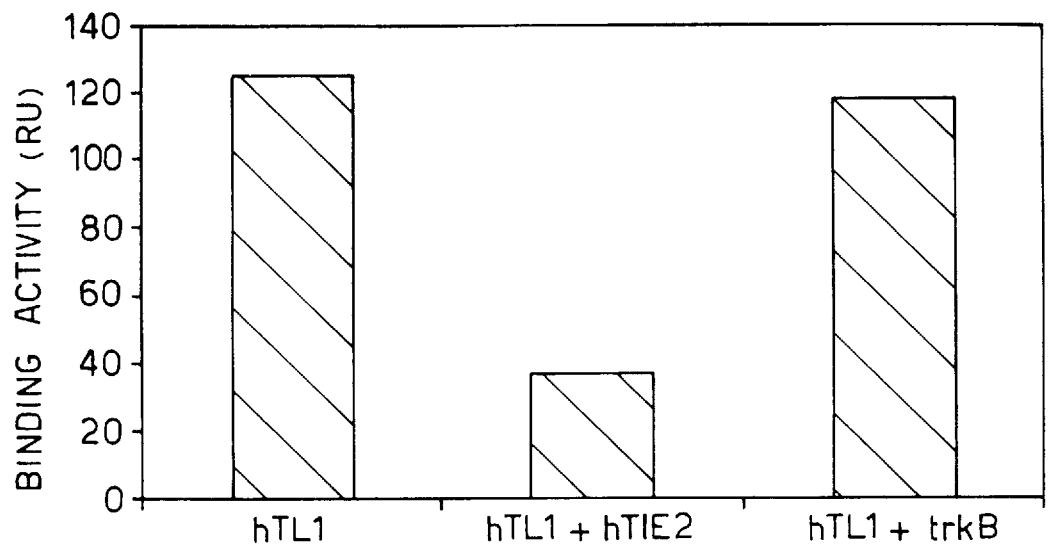
FIG. 11A and 11B—Binding of recombinant human TIE-2 ligand 1 (hTL1)(FIG. 11A) and human TIE-2 ligand 2 (hTL2)(FIG. 11B), in COS cell supernatants, to a human TIE-2 receptorbody (RB) immobilized surface. Human TIE-2-specific binding was determined by incubating the samples with 25 μg/ml of either soluble human TIE-2 RB or trkB RB; significant reduction in the binding activity is observed only for the samples incubated with human TIE-2 RB.
Figure 11B:
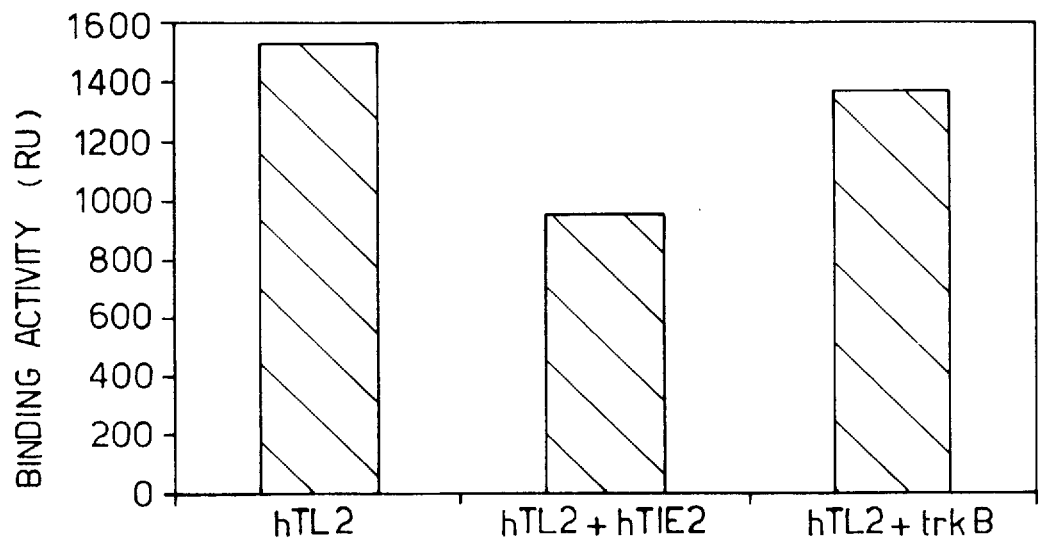

The ability of TL2 to competitively inhibit TL1 activation of the TIE-2-R was further demonstrated using the human cell hybrid line, EA.hy926 (see Example 21 for detailed description of this cell line and its maintenance). Experiments were performed in which unconcentrated COS cell media containing TL1 were mixed at varying dilutions with either MOCK- or TL2- conditioned media and placed on serum-starved EA.hy926 cell monolayers for 5 minutes at 37° C. The media were then removed, the cells were harvested by lysis and TIE-2-specific tyrosine phosphorylation was examined by Western blots, as described above. FIG. 9 shows an experiment which contains three groups of treatments, as viewed from left to right. As shown in the four lanes at the left, treatment of the EA.hy926 cells with 1×COS-TL1 alone robustly activated the endogenous TIE-2-R in these cells, whereas 1×TL2 COS medium was inactive. However, mixture of TL1 with either MOCK or TL2 demonstrated that TL2 can block the activity of TL1 in a dose-dependent fashion. In the central three pairs of lanes the ratio of TL2 (or MOCK) was decreased while the amount of TL1 in the mixture was correspondingly increased from 0.1× to 0.3×. At any of these mixture ratios the TL1:TL2 lanes showed a reduced level of TIE-2-R phosphorylation compared to that of the corresponding TL1:MOCK lanes. When the amount TL1 was held steady and the amount of TL2 (or MOCK) was decreased, however (shown in the three pairs of lanes at the right), a point was reached at which the TL2 in the sample was too dilute to effectively inhibit TL1 activity. The relative amount of each ligand present in these conditioned COS media could be estimated from their binding units as measured by the BIAcore assay and from Western blots of the COS media with ligand-specific antibodies. Consequently, we can infer that only a few-fold molar excess of TL2 is required to effectively block the activity of TL1 in vitro. This is significant because we have observed distinct examples in vivo (see Example 17 and FIG. 16) where TL2 mRNAs achieve considerable abundance relative to those of TL1. Thus, TL2 may be serving an important physiological role in effectively blocking signaling by the TIE-2-R at these sites.

Taken together these data confirm that, unlike TL1, TL2 is unable to stimulate endogenously expressed TIE-2-R on endothelial cells. Furthermore, at a few fold molar excess TL2 can block TL1 stimulation of the TIE-2 receptor, indicating that TL2 is a naturally occurring TIE-2 receptor antagonist.

EXAMPLE 10

IDENTIFICATION OF TIE-2-SPECIFIC BINDING ACTIVITY IN CONDITIONED MEDIUM AND COS CELL SUPERNATANTS

Binding activity of 10×CCM from the cell lines C2C12-ras, Rat2 ras, SHEP, and T98G, or COS cell supernatants after transfection with either human TIE-2 ligand 1 (hTL1) or human TIE-2 ligand 2 (hTL2) was measured using biosensor technology (BIAcore; Pharmacia Biosensor, Piscataway, N.J.) which monitors biomolecular interactions in real-time via surface plasmon resonance (SPR). Purified rat or human TIE-2 RB was covalently coupled through primary amines to the carboxymethyl dextran layer of a CM5 research grade sensor chip (Pharmacia Biosensor; Piscataway, N.J.). The sensor chip surface was activated using a mixture of N-hydroxysuccinimide (NHS) and N-ethyl-N'-(3-dimethylaminopropyl)carbodiimide (EDC), followed by immobilization of TIE-2 RB (25 $\mu$g/mL, pH 4.5) and deactivation of unreacted sites with 1.0M ethanolamine (pH 8.5). In general, 9000–10000 RU of each receptorbody was coupled to the sensor chip.

The running buffer used in the system was HBS (10 mM Hepes, 150 mM NaCl, 0.005% P20 surfactant, pH 7.4). The samples were centrifuged for 15 min at 4° C. and further clarified using a sterile, low protein-binding 0.45 $\mu$m filter (Millipore; Bedford, Mass.). Dextran (2 mg/ml) and P20 surfactant (0.005%) were added to each sample. Aliquots of 40 $\mu$L were injected across the immobilized surface (either rat or human TIE-2) at a flow rate of 5 $\mu$L/min and the receptor binding was monitored for 8 min. The binding activity (resonance units, RU) was measured as the difference between a baseline value determined 30 s prior to the sample injection and a measurement taken at 30 s post-injection. Regeneration of the surface was accomplished with one 15-$\mu$L pulse of 3 M MgCl$_2$.

The CCM samples (C2C12-ras, Rat2-ras, SHEP, T98G) were tested on the rat TIE-2 RB immobilized surface, while the recombinant hTL1 and hTL2 were tested on the human TIE-2 RB immobilized surface. In each case, specific binding to the TIE-2 receptorbody was evaluated by incubating the samples with 25 $\mu$g/ml of either soluble TIE-2 (rat or human) RB or trkB RB prior to assaying the binding activity. As shown in FIGS. 10A–10D and FIGS. 11A and 11B the addition of soluble trkB RB causes a slight decrease in the TIE-2 binding activity, while the addition of soluble TIE-2 RB significantly reduces the binding activity as compared to that measured in the absence of TIE-2 RB.

EXAMPLE 11

TIE-2 RB SPECIFICALLY BLOCKS ACTIVATION OF THE TIE-2 RECEPTOR BY TIE-2 LIGAND 1

The applicants sought to determine whether soluble TIE-2 RB can serve as a competitive inhibitor to block activation of TIE-2 receptor by TIE-2 ligand 1 (TL1). To do this, TL1-containing COS media were preincubated with either TIE-2- or TrkB-RB and then compared for their ability to activate TIE-2 receptors naturally present in a human endothelial cell line.

Conditioned COS media were generated from COS-7 cells transfected with either the pJFE14 expression vector alone (MOCK), or pJFE14 vector containing the human TIE-2 ligand 1 cDNA (TL1) and harvested as described in Example 9 hereinabove, with the exception that the media were sterile filtered but not concentrated. The quantity of TL1 was determined and expressed as the amount (in resonance units, R.U.) of TIE-2 receptor-specific binding activity measured by BIAcore binding assay.

Figure 12:
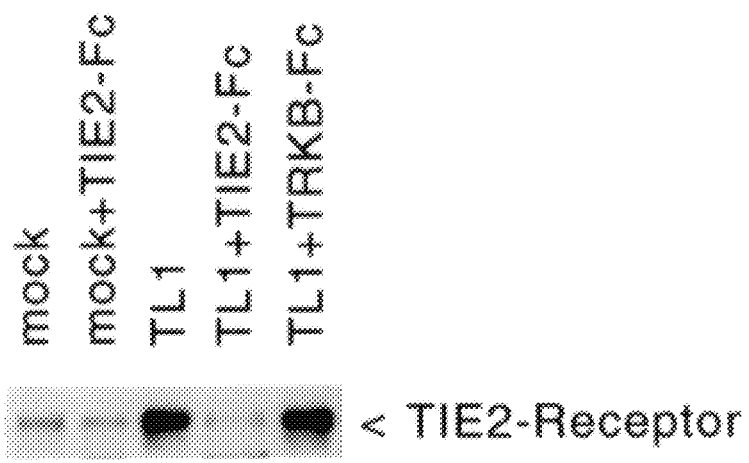
FIG. 12—Western blot showing that TIE-2 receptorbody (denoted TIE-2 RB or, as here, TIE2-Fc) blocks the activation of TIE-2 receptors by TIE-2 ligand 1 (TL1) in HUVEC cells, whereas an unrelated receptorbody (TRKB-fc) does not block this activation.

Northern (RNA) analyses revealed significant levels of tie-2 transcripts in HUVEC (Human Umbilical Vein Endothelial Cell) human primary endothelial cells (Clonetics, Inc.). Therefore, these cells were used to examine whether TIE-2 receptor can be tyrosine-phosphorylated when exposed in the presence of TIE-2- or TrkB-RBs to COS media containing TL1. HUVEC cells were maintained at 37° C., 5% CO$_2$ in a complete endothelial cell growth medium (Clonetics, Inc.) that contained 5% fetal bovine serum, soluble bovine brain extract with 10 $\mu$/ml heparin, 10 ng/ml human EGF, 1 $\mu$g/ml hydrocortisone, 50 $\mu$g/ml gentamicin and 50 ng/ml amphotericin-B. Assessment of whether TL1 could activate TIE-2 receptor in the HUVEC cells was done as follows. Confluent dishes of HUVEC cells were serum-starved for two-to-four hours in low-glucose Dulbecco's MEM at 37° C., 5% CO$_2$, followed by 10 minute incubation in starvation medium that included 0.1 mM sodium orthovanadate, a potent inhibitor of phosphotyrosine phosphatases. Meanwhile, conditioned COS media were preincubated 30 min. at room temperature with either TIE-2- or TrkB-RB added to 50 $\mu$g/ml. The starvation medium was then removed from the HUVEC dishes and incubated with the RB-containing COS media for 7 minutes at 37° C. HUVEC cells were subsequently lysed and TIE-2 receptor protein was recovered by immunoprecipitation with TIE-2 peptide antiserum, followed by Western blotting with an anti-phosphotyrosine antibody, as described in Example 1. The results are shown in FIG. 12. Phosphotyrosine levels on the TIE-2 receptor were induced by treatment of HUVEC cells with TIE-2 ligand 1 (TL1) relative to that seen with control medium (MOCK) and this induction is specifically blocked by prior incubation with TIE-2-RB (TIE-2-Fc) but not by incubation with TrkB-RB (TrkB-Fc). These data indicate that soluble TIE-2 RB can serve as a selective inhibitor to block activation of TIE-2 receptor by TIE-2 ligand 1.

EXAMPLE 12

CONSTRUCTION OF TIE-2 LIGANDBODIES

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the Spodoptera frugiperda SF-21AE insect cell line. Alternatively, the cell line SF-9 (ATCC Accession No. CRL-1711) or the cell line BTI-TN-5b1-4 may be used. DNA encoding the TL2-Fc was cloned as an Eco RI-NotI fragment into the baculovirus transfer plasmid pVL1393. Plasmid DNA was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells (2× 106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 mg/mL X-gal (5-bromo-4-chloro-3-indolyl-b- D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection.

Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5M NaCl until the absorbance at 280 nm decreased to baseline. The column was washed in PBS and eluted with 0.5M acetic acid. Column fractions were immediately neutralized by eluting into tubes containing 1 M Tris pH 9. The peak fractions containing the TL2-Fc were pooled and dialyzed versus PBS.

EXAMPLE 13

EXPRESSION OF TIE-1, TIE-2, TL1, AND TL2 IN RENAL CELL CARCINOMA

In situ hybridization experiments were performed on human renal cell carcinoma tumor tissue using TIE-1, TIE-2, TL1, and TL2 cDNA probes.

TIE-2, TIE-1, TL1, and TL2 expression were all up-regulated in the tumor vasculature. Ligand expression appeared to be localized to either the vascular endothelial cells (TL2) or very near the vascular endothelial cells in the mesenchyme (TL1). VEGF has been shown to be dramatically up-regulated in this tumor tissue. Brown, et al. Am. J. Pathol. 143:1255–1262 (1993).

EXAMPLE 14

EXPRESSION OF TIE-1, TIE-2, TL1, AND TL2 IN WOUND HEALING

In situ hybridization experiments were performed on cross-sectional tissue slices obtained from a rat cutaneous wound model using TIE-1, TIE-2, TL1, and TL2 cDNA probes. The wound healing model involves pressing a small cork bore against the skin of a rat and removing a small, cylindrical plug of skin. As healing begins at the base of the wound, a vertical slice of tissue is taken and used for in situ hybridization. In the tested tissue sample, TL1 and TL2 appeared to be slightly up-regulated by four days post-injury. In contrast to the slightly up-regulated expression of TL1 and TL2 in this tissue, VEGF expression, which may precede TL1 and TL2 expression, is dramatically up-regulated.

EXAMPLE 15

EXPRESSION OF TIE LIGANDS IN FETAL LIVER AND THYMUS

Figure 13:
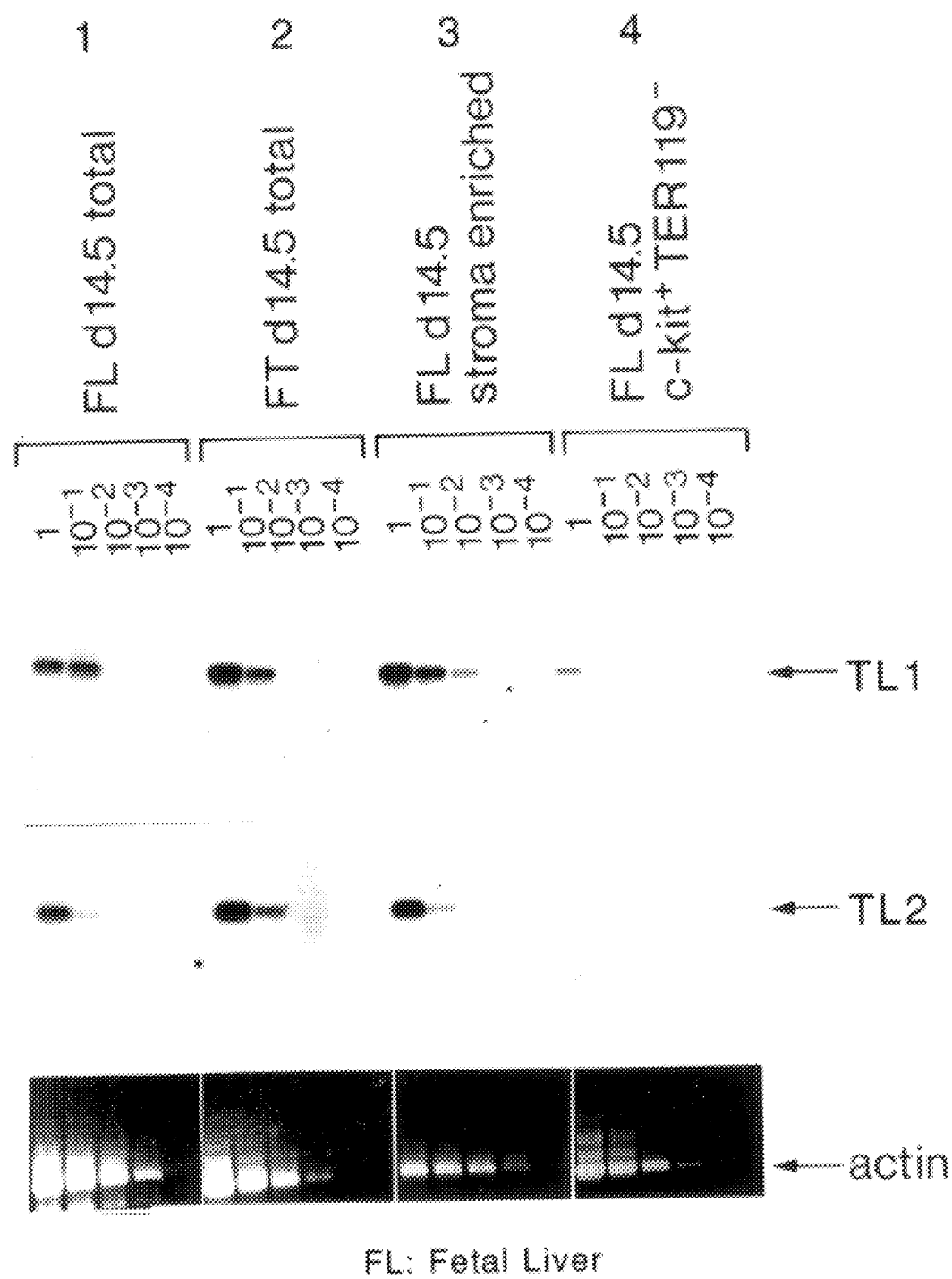
FIG. 13—Agarose gels showing serial dilutions [undiluted (1) to $10^{-4}$] of the TL1 and TL2 RT-PCR products obtained from E14.5 mouse fetal liver (Lanes 1-total, Lanes 3-stromal enriched, and Lanes 4-c-kit$^+$TER119 hematopoietic precursor cells) and E14.5 mouse fetal thymus (Lanes 2-total).
Figure 14:
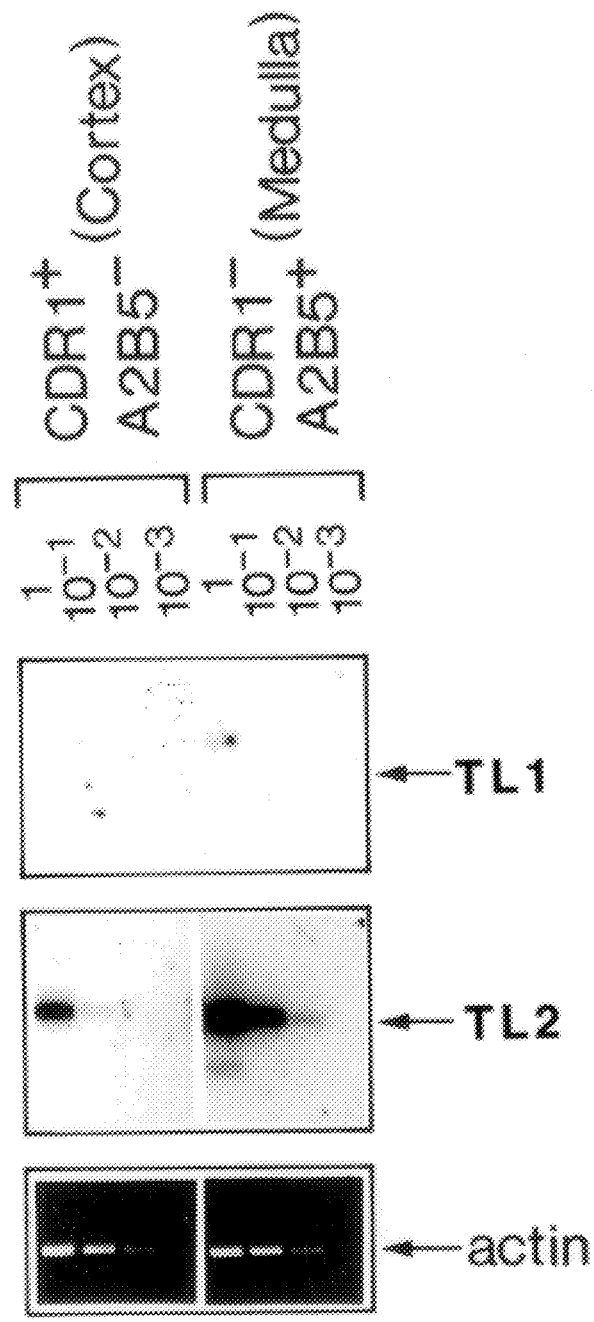
FIG. 14—Agarose gels showing serial dilutions [undiluted (1) to $10^{-3}$] of the TL1 and TL2 RT-PCR products obtained from E17.5 mouse fetal thymus cortical stromal cells (Lanes 1-CDR1+/A2B5−) and medullary stromal cells (Lane CDR1−/A2B5+).

Reverse transcription-PCR (RT-PCR) was performed on mouse E14.5 fetal liver and mouse E17.5 fetal thymus. Agarose gel electrophoresis of the RT-PCR products revealed that in the mouse fetal liver, TIE-2 ligand 1 (TL1) RNA is enriched in the stromal region, but is absent in c-kit$^+$TER119 hematopoietic precursor cells. In this same tissue, TIE-2 ligand 2 (TL2) RNA is enriched in the stromal cells, but absent in the hematopoietic precursor cells (FIG. 13). In the mouse fetal thymus, TL2 is enriched in the stromal cells (FIG. 14).

EXAMPLE 16

THE TIE RECEPTOR/LIGAND SYSTEM IN ANGIOGENESIS

Although the TIE-2/TIE ligand system appears to play an important role in endothelial cell biology, it has not been shown to play a significant, active role in the early to intermediate stages of vascularization (e g angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

Figure 15:
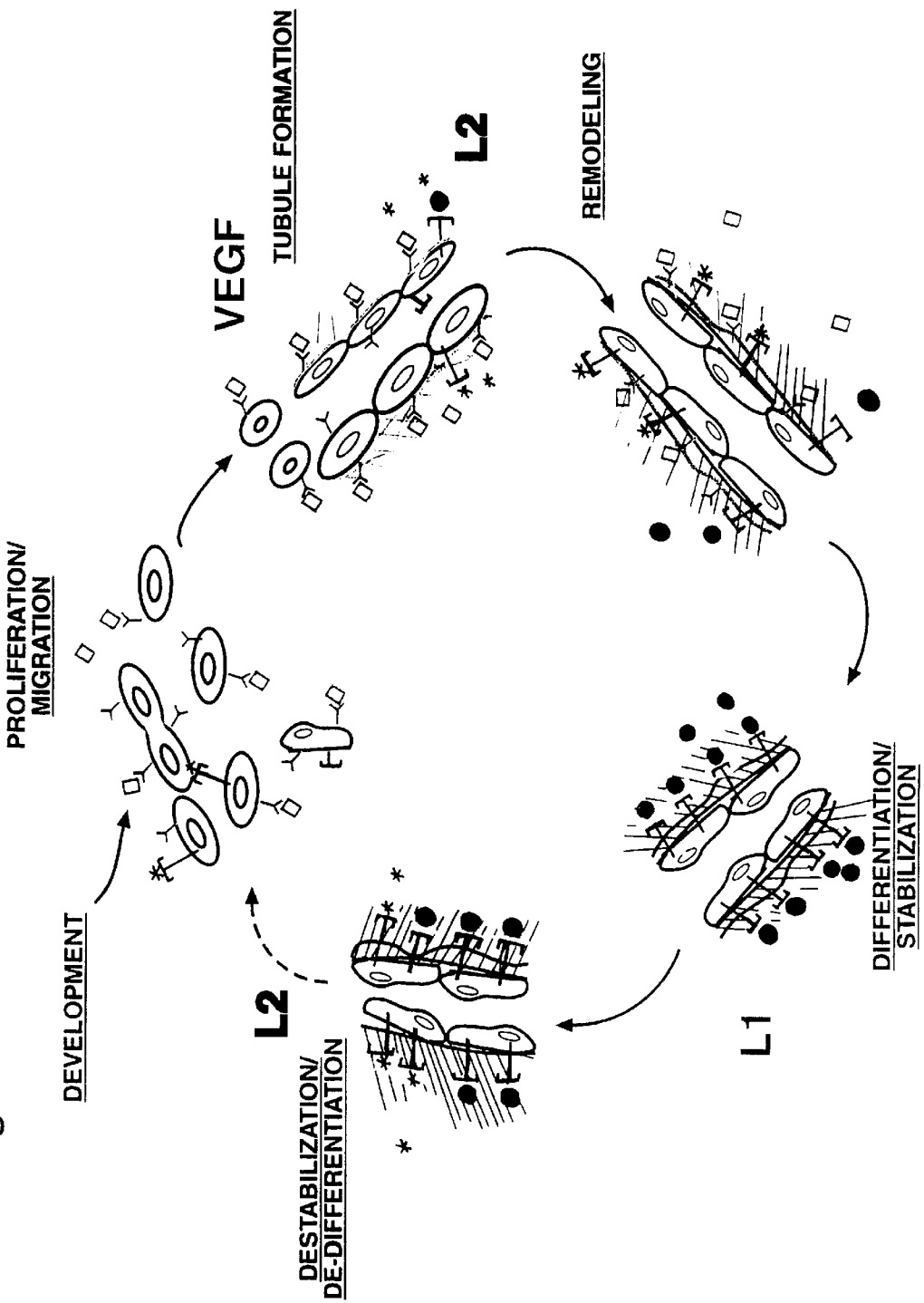
FIG. 15—A schematic representation of the hypothesized role of the TIE-2/TIE ligands in angiogenesis. TL1 is represented by (•), TL2 is represented by (*), TIE-2 is represented by (T), VEGF is represented by ([]), and flk-1 (a VEGF receptor) is represented by (Y).

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/ de-differentiation of mature endothelial cells allowing the formation of new vessels from existing vasculature, inhibition of inappropriate blood vessel formation, and regression/ involution of mature blood vessels). FIG. 15 is a schematic representation of the hypothesized role of the TIE-2/TIE ligands in angiogenesis. In this figure TL1 is represented by (•), TL2 is represented by (*), TIE-2 is represented by (T), VEGF is represented by ([]), and flk-1 (a VEGF receptor) is represented by (Y).

EXAMPLE 17

EXPRESSION OF TIE LIGANDS IN THE FEMALE REPRODUCTIVE SYSTEM: EXPRESSION IN THE OVARY

Figure 16:
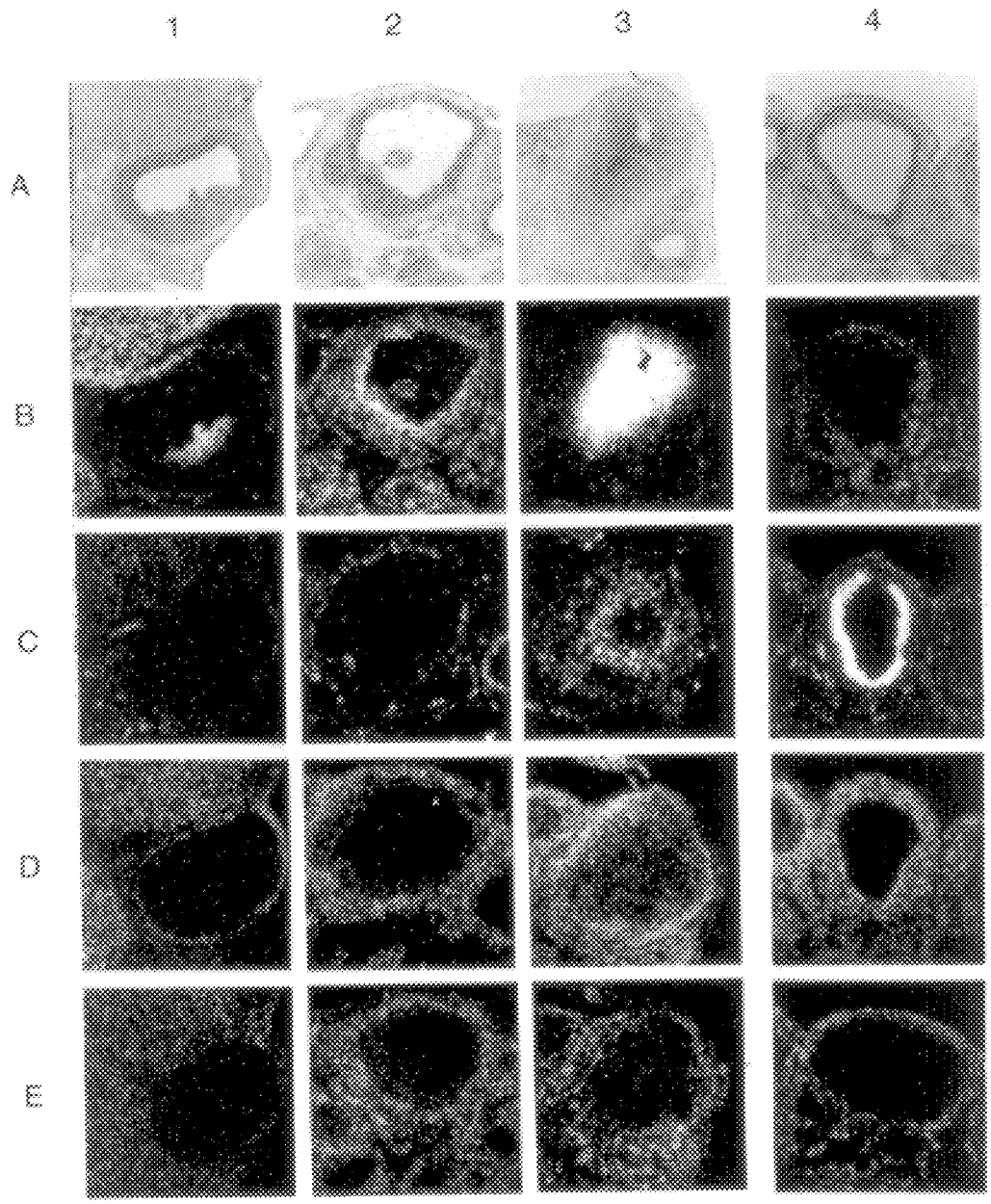
FIG. 16—In situ hybridization slides showing the temporal expression pattern of TIE-2, TL1, TL2, and VEGF during angiogenesis associated with follicular development and corpus luteum formation in the ovary of a rat that was treated with pregnant mare serum. Column 1: Early pre-ovulatory follicle; Column 2: pre-ovulatory follicle; Column 3: early corpus luteum; and Column 4: atretic follicle; Row A: bright field; Row B: VEGF; Row C: TL2; Row D: TL1 and Row E: TIE-2 receptor.

Preliminary observations made in experiments examining the expression of the TIE receptors and ligands in the female reproductive system are consistent with the hypothesis the TL1 plays a role in neovascularization which temporally follows that of VEGF. The pattern of TL2 expression is also consistent with an antagonism of the action of TL1, and a specific role in vascular regression. To verify this, expression of relevant mRNAs can be examined following experimental induction of follicular and luteal development so that their temporal relation to various aspects of neovascularization/vascular regression can be more clearly defined (e.g. in conjunction with endothelial cell staining, vascular fills). Angiogenesis associated with follicular development and corpus luteum formation in staged ovaries of mature, female rats or following induced ovulation in pre-pubertal animals was followed using in situ hybridization. FIG. 16 contains photographs of in situ hybridization slides showing the temporal expression pattern of TIE-2, TL1, TL2, and VEGF during the ovarian cycle [Column 1: Early pre-ovulatory follicle; Column 2: pre-ovulatory follicle; Column 3: early corpus luteum; and Column 4: atretic follicle; Row A:bright field; Row B:VEGF; Row C: TL2; Row D: TL1 and Row E: TIE-2 receptor]. These studies revealed that VEGF, TL1 and TL2 are expressed in a temporally and spatially coordinate fashion with respect to the development and regression of vasculature in the ovary, specifically with respect to the establishment of the vascular system which is generated in the course of the conversion of an ovarian follicle to a corpus luteum (CL).

Briefly, VEGF expression increases in the follicular granule layer prior to its vascularization during the process of luteinization. During the process of CL formation, highest levels of VEGF expression are apparent in the center of the developing CL in the vicinity of luteinizing cells which are not yet vascularized. VEGF levels remain moderately high and are diffusely distributed in the developed CL. In contrast, noticeably enhanced expression of TIE-2 ligand 1 occurs only late in process of CL formation, after a primary vascular plexus has been established. Later, TL1 expression is apparent throughout the CL at which time the definitive capillary network of the CL has been established.

TL2 exhibits a more complex pattern of expression than either VEGF or TL1. In the developing CL, TL2 is expressed at highest levels at the front of the developing capillary plexus- between the central avascuiar region of the CL where VEGF expression is highest, and the most peripheral portion of the CL where TL1 expression is dominant and where the luteinization process is complete and the vascular system is most mature. TL2 also appears to be expressed at high levels in the follicular layer of large follicles which are undergoing atresia. While TL1 is also apparent in atretic follicles, VEGF is not expressed.

The pattern of expression described above is most consistent with a role for VEGF in the initiation of angiogenesis, with TL1 acting late in this process-for example in modeling and/or stabilization of the definitive vascular network. In contrast, TL2 is present both in areas of active expansion of a newly forming vascular network (during CL formation), and in regions which fail to establish a new vasculature and vascular regression is in progress (atretic follicles). This suggests a more dynamic and complex role for TL2, possibly involving destabilization of existing vasculature (necessary for regression) or developing vasculature (necessary for the dynamic modeling of newly forming vessels).

EXAMPLE 18

CONSTRUCTION AND CHARACTERIZATION OF THE CYS-TL1 MUTANT

The TIE-2 ligands have two major structural domains, one described as a "coiled-coil" domain comprising the approximate C-terminal third of the protein and the other a "fibrinogen-like" domain comprising the approximate N-terminal two-thirds of the protein. Although the TIE-2 ligands, designated TL1 and TL2, share similar structural homology, they exhibit different physical and biological properties. Under non-reducing electrophoretic conditions, both proteins exhibit covalent, multimeric structures, with TL1 existing primarily as a trimer and TL2 existing primarily as a dimer. FIG. 17 is a schematic representation of how the TIE-2 ligands may be interacting to form multimers. In terms of biological activity, TL1 has been shown to be an agonist of the TIE-2 receptor, as demonstrated by induction of phosphorylation in TIE-2 expressing cells. TL2, on the other hand, appears to be a competitive inhibitor of TL1. Investigations into what factors might be contributing to the different physical and biological properties of the two molecules revealed the presence of a cysteine residue (CYS265) preceding the fibrinogen-like domain in TL1 but absent in TL2. This CYS265 residue in TL1 is encoded by TGC and is located at about nucleotides 1102–1104 at the approximate junction between the coiled-coil and fibrinogen-like domains. Because cysteine residues are generally involved in disulfide bond formation, the presence of which can contribute to both the tertiary structure and biological properties of a molecule, it was thought the perhaps the presence of the CYS265 in TL1 might be at least partially responsible for the different properties of the two molecules. To test this hypothesis, an expression plasmid was constructed which contained a mutation in TL1 in which the CYS was replaced with an amino acid which does not form disulfide bonds. In addition to this TL1/CYS$^-$ mutant, a second expression plasmid was constructed which mutated the corresponding position in TL2 so that this residue was now a cysteine. Both non-mutated and mutated expression plasmids of TL1 and TL2 were transiently transfected into COS cells. Cell supernatants containing the recombinant proteins were harvested and samples subjected to both reducing and non-reducing SDS/PAGE electrophoresis and subsequent western blotting. FIGS. 18A and 18B contains western blots of both non-mutated and mutated TL1 and TL2 proteins under revealing that the TL1/CYS$^-$ mutant behaves more TL2-like in that it runs as a dimer and that the TL2/CYS$_+$ mutant behaves more TL1-like in that it is able to form a trimer as well as higher-order multimers. Interestingly, when the two mutant proteins were tested for their ability to induce phosphorylation in TIE-2 expressing cells, the TL1/CYS$^-$ mutant was able to activate the TIE-2 receptor, whereas the TL2/CYS$^+$ mutant did not gain any activating activity.

EXAMPLE 19

CONSTRUCTION AND CHARACTERIZATION OF FIBRINOGEN-LIKE DOMAIN ONLY MUTANTS

In order to test whether the fibrinogen-like domain (F-domain) of the TIE-2 ligands contained TIE-2 activating activity, expression plasmids were constructed which deleted the coiled-coil domain, leaving only that portion of the DNA sequence encoding the F-domain (beginning at about nucleotide 1159, amino acid residue ARG284). This mutant construct was transiently transfected into COS cells. The supernatant containing the recombinant protein was harvested. The TL1/F-domain mutant was tested for it's ability to bind the TIE-2 receptor. The results showed that, as a monomer, the TL1/F-domain mutant was not able to bind TIE-2 at a detectable level. However, when the TL1/F-domain monomer was myc-tagged and subsequently clustered with an antibody directed against the myc tag, it did exhibit detectable binding to TIE-2. However, the antibody-clustered TL1/F-domain mutant was not able to induce phosphorylation in a TIE-2 expressing cell line. FIG. 17 shows a schematic representation of the F-domain construct and its binding ability plus and minus antibody clustering.

EXAMPLE 20

A RECEPTORBODY BINDING ASSAY AND A LIGAND BINDING AND COMPETITION ASSAY

Figure 19:
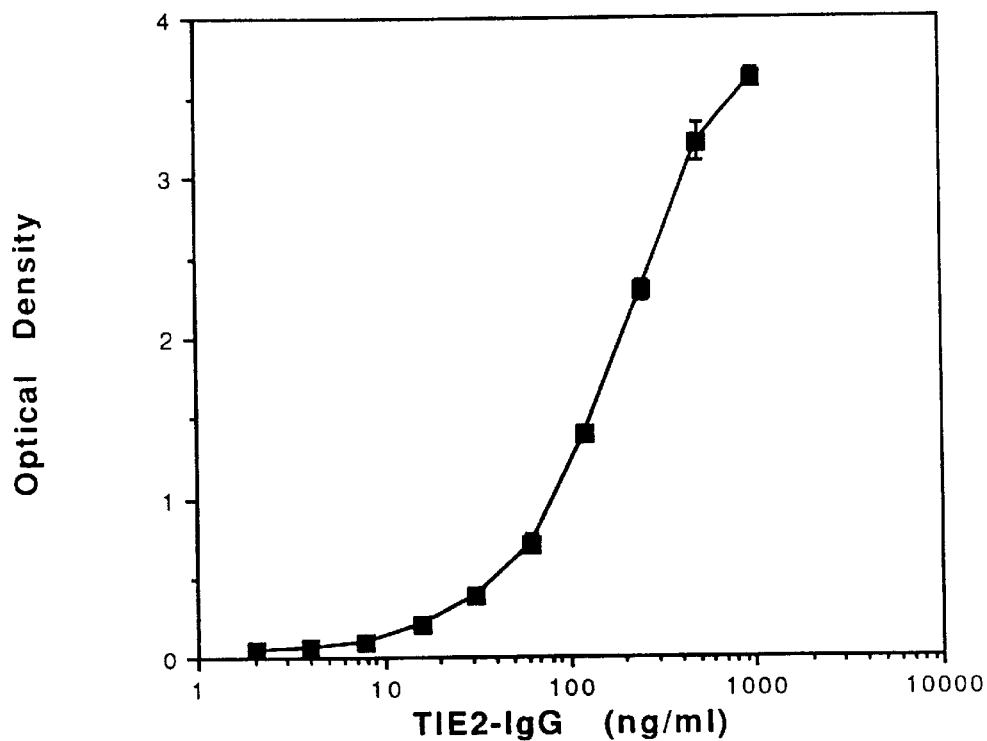
FIG. 19—A typical curve of TIE-2-IgG binding to immobilized TL1 in a quantitative cell-free binding assay.
Figure 20:
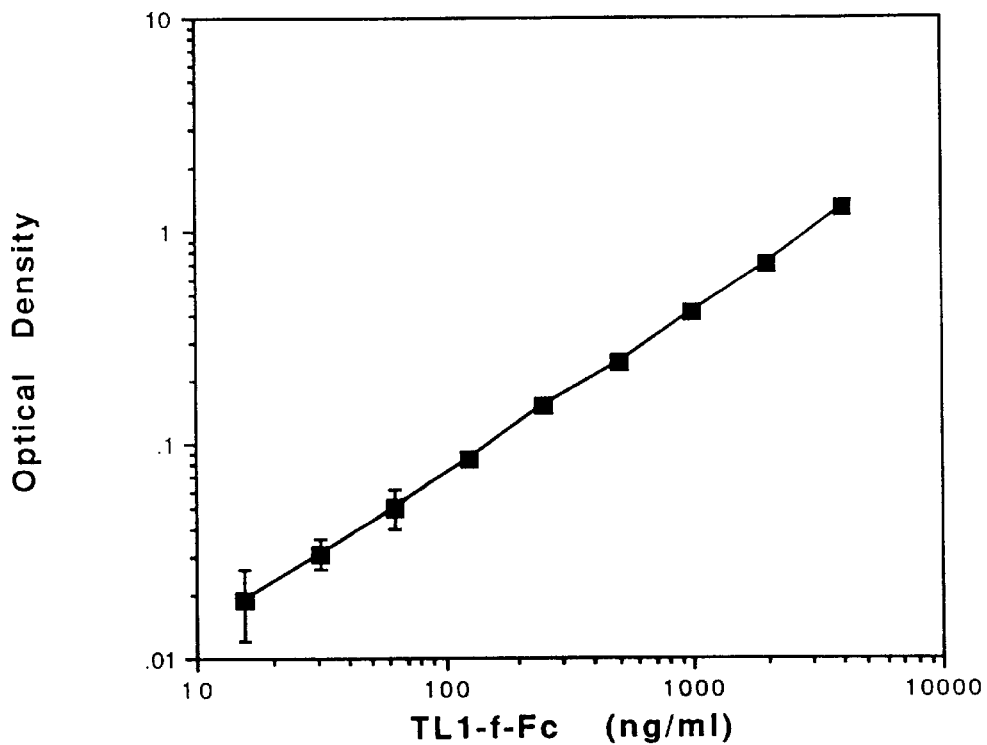
FIG. 20—A typical curve showing TIE-2 ligand 1 ligandbody comprising the fibrinogen-like domain of the ligand bound to the Fc domain of IgG (TL1-fFc) binding to immobilized TIE-2 ectodomain in a quantitative cell-free binding assay.

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific anti-human Fc antibody which is alkaline phosphatase tagged. Excess reporter antibody is washed away, then the AP reaction is developed using a colored substrate. The assay is quantitated using a spectrophotometer. FIG. 19 shows a typical TIE-2-IgG binding curve. This assay has been used to evaluate the integrity of TIE-2-lgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 20 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 21

EA.hy926 CELL LINE CAN BE USED AS A REPORTER CELL LINE FOR TIE LIGAND ACTIVITY

EA.hy926 is a cell hybrid line that was established by fusion of HUVEC with the human lung carcinoma-derived line, A549 [Edgell, et al. Proc. Natl. Acad. Sci. (USA) 80, 3734–3737 (1983). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1×hypoxanthine-aminopterinthymidine (HAT, Gibco/BRL). After three to four days of growth, the cells are passaged once again at 1.5×10⁶ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

EXAMPLE 22

ISOLATION AND SEQUENCING OF FULL LENGTH cDNA CLONE ENCODING MAMMALIAN TIE LIGAND-3

TIE ligand-3 (TL3) was cloned from a mouse BAC genomic library (Research Genetics) by hybridizing library duplicates, with either mouse TL1 or mouse TL2 probes corresponding to the entire coding sequence of those genes. Each copy of the library was hybridized using phosphate buffer at 55° C. overnight. After hybridization, the filters were washed using 2×SSC, 0.1% SDS at 60° C., followed by exposure of X ray film to the filters. Strong hybridization signals were identified corresponding to mouse TL1 and mouse TL2. In addition, signals were identified which weakly hybridized to both mouse TL1 and mouse TL2. DNA corresponding to these clones was purified, then digested with restriction enzymes, and two fragments which hybridized to the original probes were subcloned into a bacterial plasmid and sequenced. The sequence of the fragments contained two exons with homology to both mouse TL1 and mouse TL2. Primers specific for these sequences were used as PCR primers to identify tissues containing transcripts corresponding to TL3. A PCR band corresponding to TL3 was identified in a mouse uterus cDNA library in lambda gt-11. (Clontech Laboratories, Inc., Palo Alto, Calif.). Plaques were plated at a density of 1.25×10⁶/20×20 cm plate and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at "normal" stringency (2×SSC, 65° C.) with a 200 bp PCR radioactive probe made to the mouse TL3 sequence. Hybridization was at 65° C. in a solution containing 0.5 mg/ml salmon sperm DNA. Filters were washed in 2×SSC at 65° C. and exposed for 6 hours to X-ray film. Two positive clones that hybridized in duplicate were picked. EcoRI digestion of phage DNA obtained from these clones indicated two independent clones with insert sizes of approximately 1.2 kb and approximately 2.2 kb. The 2.2 kb EcoRI insert was subcloned into the EcoRI site of pBluescript KS (Stratagene). Sequence analysis showed that the longer clone was lacking an initiator methionine and signal peptide but otherwise encoded a probe homologous to both mouse TL1 and mouse TL2.

Two TL3-specific PCR primers were then synthesised as follows:

US2: cctctgggctcgccagtttgttagg

US1: ccagctggcagatatcagg

The following PCR reactions were performed using expression libraries derived from the mouse cell lines C2C12ras and MG87. In the primary PCR reaction, the specific primer US2 was used in conjunction with vector-specific oligos to allow amplification in either orientation. PCR was in a total volume of 100 ml using 35 cycles of 94° C., 1 min; 42° C. or 48° C. for 1 min; 72° C., 1 min. The secondary PCR reaction included the second specific primer, US1, which is contained within the primary PCR product, in conjunction with the same vector oligos. The secondary reactions were for 30 cycles, using the same temperatures and times as previous. PCR products were gel isolated and submitted for sequence analysis. On the basis of sequences obtained from a total of four independent PCR reactions using two different cDNA libraries, the 5' end of the TL3 sequence was deduced. Northern analysis revealed moderate to low levels of mouse TL3 transcript in mouse placenta. The expression of mouse TL3 consisted of a transcript of approximately 3 kb. The full length TL3 coding sequence is set forth in FIGS. 21A and 21B (SEQ. ID NOS.7&8).

The mouse TL3 sequence may then be used to obtain a human clone containing the coding sequence of human TL3 by hybridizing either a human genomic or cDNA library with a probe corresponding to mouse TL3 as has been described previously, for example, in Example 8 supra.

DEPOSITS

The following have been deposited with the American Type Culture Collection, 12301 Parklawn Drive, Rockville, Md. 20852 in accordance with the Budapest Treaty. A plasmid clone encoding a TIE-2 ligand was deposited with the ATCC on Oct. 7, 1994 and designated as "pJFE14 encoding TIE-2 ligand" under ATCC Accession No. 75910. Recombinant *Autographa californica* baculovirus encoding TIE-2 receptorbody was deposited with the ATCC on Oct. 7, 1994 and designated as "vTIE-2 receptorbody" under ATCC Accession No. VR2484. A lambda phage vector containing human tie-2 ligand DNA was deposited with the ATCC on Oct. 26, 1994 and designated as λgt10 encoding htie-2 ligand 1 under ATCC Accession No. 75928. A plasmid clone encoding a second TIE-2 ligand was deposited with the ATCC on Dec. 9, 1994 and designated as "pBluescript KS encoding human TIE 2 ligand 2" under ATCC Accession No. 75963.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated nucleic acid molecule comprising a nucleotide sequence encoding TIE ligand-3, wherein the nucleotide sequence is selected from the group consisting of:

(a) the nucleotide sequence encoding TIE ligand-3 as set forth in FIGS. 21A and 21B (SEQ. ID NO.7); and (b) a nucleotide sequence that, as a result of the degeneracy of the genetic code, differs from the nucleotide sequence of (a) and encodes a ligand that binds TIE-2 receptor.

2. A vector which comprises the nucleic acid molecule of claim 1.

3. A vector according to claim 2, wherein the nucleic acid molecule is operatively linked to an expression control sequence capable of directing expression of the ligand in a host cell.

4. A vector according to claim 3, which is a plasmid.

5. Isolated TIE ligand-3 encoded by a nucleic acid molecule according to claim 1.

6. A host-vector system for the production of TIE ligand-3 which comprises a vector of claim 3, in a host cell.

7. A host-vector system according to claim 6, wherein the host cell is a bacterial, yeast, insect or mammalian cell.

8. A host-vector system comprising the host-vector system of claim 6, and a nucleic acid encoding the TIE-2 receptor.

9. A method of producing TIE ligand-3 which comprises growing cells of the host-vector system of claim 6, under conditions permitting production of the TIE ligand-3, and recovering the TIE ligand-3 so produced.

10. A conjugate comprising the ligand of claim 5, conjugated to a cytotoxic agent.

11. The conjugate according to claim 10, wherein the cytotoxic agent is a radioisotope or toxin.

12. A composition comprising the ligand of claim 5 and a carrier.

13. A composition comprising the conjugate of claim 10 and a carrier.

14. A ligandbody which comprises the ligand of claim 5, fused to an immunoglobulin constant region.

15. The ligandbody of claim 14, wherein the immunoglobulin constant region is the Fc portion of human IgG1.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 2149 base pairs
( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 310..1806

( x i ) SEQUENCE DESCRIPTION: SEQ ID NO:1:

```
CAGCTGACTC  AGGCAGGCTC  CATGCTGAAC  GGTCACACAG  AGAGGAAACA  ATAAATCTCA        60

GCTACTATGC  AATAAATATC  TCAAGTTTTA  ACGAAGAAAA  ACATCATTGC  AGTGAAATAA       120

AAAATTTTAA  AATTTTAGAA  CAAAGCTAAC  AAATGGCTAG  TTTTCTATGA  TTCTTCTTCA       180

AACGCTTTCT  TTGAGGGGGA  AAGAGTCAAA  CAAACAAGCA  GTTTTACCTG  AAATAAAGAA       240

CTAGTTTTAG  AGGTCAGAAG  AAAGGAGCAA  GTTTTGCGAG  AGGCACGGAA  GGAGTGTGCT       300

GGCAGTACA   ATG  ACA  GTT  TTC  CTT  TCC  TTT  GCT  TTC  CTC  GCT  GCC  ATT   348
            Met  Thr  Val  Phe  Leu  Ser  Phe  Ala  Phe  Leu  Ala  Ala  Ile
             1                    5                        10

CTG  ACT  CAC  ATA  GGG  TGC  AGC  AAT  CAG  CGC  CGA  AGT  CCA  GAA  AAC  AGT  396
Leu  Thr  His  Ile  Gly  Cys  Ser  Asn  Gln  Arg  Arg  Ser  Pro  Glu  Asn  Ser
          15                   20                       25

GGG  AGA  AGA  TAT  AAC  CGG  ATT  CAA  CAT  GGG  CAA  TGT  GCC  TAC  ACT  TTC  444
Gly  Arg  Arg  Tyr  Asn  Arg  Ile  Gln  His  Gly  Gln  Cys  Ala  Tyr  Thr  Phe
     30                    35                       40                    45

ATT  CTT  CCA  GAA  CAC  GAT  GGC  AAC  TGT  CGT  GAG  AGT  ACG  ACA  GAC  CAG  492
Ile  Leu  Pro  Glu  His  Asp  Gly  Asn  Cys  Arg  Glu  Ser  Thr  Thr  Asp  Gln
                        50                   55                        60

TAC  AAC  ACA  AAC  GCT  CTG  CAG  AGA  GAT  GCT  CCA  CAC  GTG  GAA  CCG  GAT  540
Tyr  Asn  Thr  Asn  Ala  Leu  Gln  Arg  Asp  Ala  Pro  His  Val  Glu  Pro  Asp
               65                        70                   75

TTC  TCT  TCC  CAG  AAA  CTT  CAA  CAT  CTG  GAA  CAT  GTG  ATG  GAA  AAT  TAT  588
Phe  Ser  Ser  Gln  Lys  Leu  Gln  His  Leu  Glu  His  Val  Met  Glu  Asn  Tyr
          80                        85                   90

ACT  CAG  TGG  CTG  CAA  AAA  CTT  GAG  AAT  TAC  ATT  GTG  GAA  AAC  ATG  AAG  636
Thr  Gln  Trp  Leu  Gln  Lys  Leu  Glu  Asn  Tyr  Ile  Val  Glu  Asn  Met  Lys
     95                   100                       105

TCG  GAG  ATG  GCC  CAG  ATA  CAG  CAG  AAT  GCA  GTT  CAG  AAC  CAC  ACG  GCT  684
Ser  Glu  Met  Ala  Gln  Ile  Gln  Gln  Asn  Ala  Val  Gln  Asn  His  Thr  Ala
110                        115                       120                  125

ACC  ATG  CTG  GAG  ATA  GGA  ACC  AGC  CTC  CTC  TCT  CAG  ACT  GCA  GAG  CAG  732
Thr  Met  Leu  Glu  Ile  Gly  Thr  Ser  Leu  Leu  Ser  Gln  Thr  Ala  Glu  Gln
                    130                       135                  140

ACC  AGA  AAG  CTG  ACA  GAT  GTT  GAG  ACC  CAG  GTA  CTA  AAT  CAA  ACT  TCT  780
Thr  Arg  Lys  Leu  Thr  Asp  Val  Glu  Thr  Gln  Val  Leu  Asn  Gln  Thr  Ser
               145                       150                  155

CGA  CTT  GAG  ATA  CAG  CTG  CTG  GAG  AAT  TCA  TTA  TCC  ACC  TAC  AAG  CTA  828
Arg  Leu  Glu  Ile  Gln  Leu  Leu  Glu  Asn  Ser  Leu  Ser  Thr  Tyr  Lys  Leu
          160                       165                  170

GAG  AAG  CAA  CTT  CTT  CAA  CAG  ACA  AAT  GAA  ATC  TTG  AAG  ATC  CAT  GAA  876
Glu  Lys  Gln  Leu  Leu  Gln  Gln  Thr  Asn  Glu  Ile  Leu  Lys  Ile  His  Glu
```

-continued

|   |   |   | 175 |   |   |   |   | 180 |   |   |   |   | 185 |   |   |   |
|---|---|---|---|---|---|---|---|---|---|---|---|---|---|---|---|---|

```
AAA AAC AGT TTA TTA GAA CAT AAA ATC TTA GAA ATG GAA GGA AAA CAC      924
Lys Asn Ser Leu Leu Glu His Lys Ile Leu Glu Met Glu Gly Lys His
190             195                 200                 205

AAG GAA GAG TTG GAC ACC TTA AAG GAA GAG AAA GAG AAC CTT CAA GGC      972
Lys Glu Glu Leu Asp Thr Leu Lys Glu Glu Lys Glu Asn Leu Gln Gly
                210                 215                 220

TTG GTT ACT CGT CAA ACA TAT ATA ATC CAG GAG CTG GAA AAG CAA TTA     1020
Leu Val Thr Arg Gln Thr Tyr Ile Ile Gln Glu Leu Glu Lys Gln Leu
            225                 230                 235

AAC AGA GCT ACC ACC AAC AAC AGT GTC CTT CAG AAG CAG CAA CTG GAG     1068
Asn Arg Ala Thr Thr Asn Asn Ser Val Leu Gln Lys Gln Gln Leu Glu
        240                 245                 250

CTG ATG GAC ACA GTC CAC AAC CTT GTC AAT CTT TGC ACT AAA GAA GGT     1116
Leu Met Asp Thr Val His Asn Leu Val Asn Leu Cys Thr Lys Glu Gly
255                 260                 265

GTT TTA CTA AAG GGA GGA AAA AGA GAG GAA GAG AAA CCA TTT AGA GAC     1164
Val Leu Leu Lys Gly Gly Lys Arg Glu Glu Glu Lys Pro Phe Arg Asp
270                 275                 280                 285

TGT GCA GAT GTA TAT CAA GCT GGT TTT AAT AAA AGT GGA ATC TAC ACT     1212
Cys Ala Asp Val Tyr Gln Ala Gly Phe Asn Lys Ser Gly Ile Tyr Thr
                290                 295                 300

ATT TAT ATT AAT AAT ATG CCA GAA CCC AAA AAG GTG TTT TGC AAT ATG     1260
Ile Tyr Ile Asn Asn Met Pro Glu Pro Lys Lys Val Phe Cys Asn Met
            305                 310                 315

GAT GTC AAT GGG GGA GGT TGG ACT GTA ATA CAA CAT CGT GAA GAT GCA     1308
Asp Val Asn Gly Gly Gly Trp Thr Val Ile Gln His Arg Glu Asp Ala
        320                 325                 330

AGT CTA GAT TTC CAA AGA GGC TGG AAG GAA TAT AAA ATG GGT TTT GGA     1356
Ser Leu Asp Phe Gln Arg Gly Trp Lys Glu Tyr Lys Met Gly Phe Gly
335                 340                 345

AAT CCC TCC GGT GAA TAT TGG CTG GGG AAT GAG TTT ATT TTT GCC ATT     1404
Asn Pro Ser Gly Glu Tyr Trp Leu Gly Asn Glu Phe Ile Phe Ala Ile
350                 355                 360                 365

ACC AGT CAG AGG CAG TAC ATG CTA AGA ATT GAG TTA ATG GAC TGG GAA     1452
Thr Ser Gln Arg Gln Tyr Met Leu Arg Ile Glu Leu Met Asp Trp Glu
                370                 375                 380

GGG AAC CGA GCC TAT TCA CAG TAT GAC AGA TTC CAC ATA GGA AAT GAA     1500
Gly Asn Arg Ala Tyr Ser Gln Tyr Asp Arg Phe His Ile Gly Asn Glu
            385                 390                 395

AAG CAA AAC TAT AGG TTG TAT TTA AAA GGT CAC ACT GGG ACA GCA GGA     1548
Lys Gln Asn Tyr Arg Leu Tyr Leu Lys Gly His Thr Gly Thr Ala Gly
        400                 405                 410

AAA CAG AGC AGC CTG ATC TTA CAC GGT GCT GAT TTC AGC ACT AAA GAT     1596
Lys Gln Ser Ser Leu Ile Leu His Gly Ala Asp Phe Ser Thr Lys Asp
415                 420                 425

GCT GAT AAT GAC AAC TGT ATG TGC AAA TGT GCC CTC ATG TTA ACA GGA     1644
Ala Asp Asn Asp Asn Cys Met Cys Lys Cys Ala Leu Met Leu Thr Gly
430                 435                 440                 445

GGA TGG TGG TTT GAT GCT TGT GGC CCC TCC AAT CTA AAT GGA ATG TTC     1692
Gly Trp Trp Phe Asp Ala Cys Gly Pro Ser Asn Leu Asn Gly Met Phe
                450                 455                 460

TAT ACT GCG GGA CAA AAC CAT GGA AAA CTG AAT GGG ATA AAG TGG CAC     1740
Tyr Thr Ala Gly Gln Asn His Gly Lys Leu Asn Gly Ile Lys Trp His
            465                 470                 475

TAC TTC AAA GGG CCC AGT TAC TCC TTA CGT TCC ACA ACT ATG ATG ATT     1788
Tyr Phe Lys Gly Pro Ser Tyr Ser Leu Arg Ser Thr Thr Met Met Ile
        480                 485                 490

CGA CCT TTA GAT TTT TGA AAGCGCAATG TCAGAAGCGA TTATGAAAGC            1836
Arg Pro Leu Asp Phe  *
```

-continued

```
        4 9 5

AACAAAGAAA  TCCGGAGAAG  CTGCCAGGTG  AGAAACTGTT  TGAAAACTTC  AGAAGCAAAC     1896

AATATTGTCT  CCCTTCCAGC  AATAAGTGGT  AGTTATGTGA  AGTCACCAAG  GTTCTTGACC     1956

GTGAATCTGG  AGCCGTTTGA  GTTCACAAGA  GTCTCTACTT  GGGGTGACAG  TGCTCACGTG     2016

GCTCGACTAT  AGAAAACTCC  ACTGACTGTC  GGGCTTTAAA  AAGGGAAGAA  ACTGCTGAGC     2076

TTGCTGTGCT  TCAAACTACT  ACTGGACCTT  ATTTTGGAAC  TATGGTAGCC  AGATGATAAA     2136

TATGGTTAAT  TTC                                                            2149
```

( 2 ) INFORMATION FOR SEQ ID NO:2:

( i ) SEQUENCE CHARACTERISTICS:
        ( A ) LENGTH: 498 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Val  Phe  Leu  Ser  Phe  Ala  Phe  Leu  Ala  Ala  Ile  Leu  Thr  His
 1                   5                  10                       15

Ile  Gly  Cys  Ser  Asn  Gln  Arg  Arg  Ser  Pro  Glu  Asn  Ser  Gly  Arg  Arg
                20                      25                      30

Tyr  Asn  Arg  Ile  Gln  His  Gly  Gln  Cys  Ala  Tyr  Thr  Phe  Ile  Leu  Pro
               35                      40                      45

Glu  His  Asp  Gly  Asn  Cys  Arg  Glu  Ser  Thr  Thr  Asp  Gln  Tyr  Asn  Thr
         50                      55                      60

Asn  Ala  Leu  Gln  Arg  Asp  Ala  Pro  His  Val  Glu  Pro  Asp  Phe  Ser  Ser
 65                      70                      75                       80

Gln  Lys  Leu  Gln  His  Leu  Glu  His  Val  Met  Glu  Asn  Tyr  Thr  Gln  Trp
                    85                      90                      95

Leu  Gln  Lys  Leu  Glu  Asn  Tyr  Ile  Val  Glu  Asn  Met  Lys  Ser  Glu  Met
               100                     105                     110

Ala  Gln  Ile  Gln  Gln  Asn  Ala  Val  Gln  Asn  His  Thr  Ala  Thr  Met  Leu
          115                     120                     125

Glu  Ile  Gly  Thr  Ser  Leu  Leu  Ser  Gln  Thr  Ala  Glu  Gln  Thr  Arg  Lys
     130                     135                     140

Leu  Thr  Asp  Val  Glu  Thr  Gln  Val  Leu  Asn  Gln  Thr  Ser  Arg  Leu  Glu
145                      150                     155                     160

Ile  Gln  Leu  Leu  Glu  Asn  Ser  Leu  Ser  Thr  Tyr  Lys  Leu  Glu  Lys  Gln
                    165                     170                     175

Leu  Leu  Gln  Gln  Thr  Asn  Glu  Ile  Leu  Lys  Ile  His  Glu  Lys  Asn  Ser
               180                     185                     190

Leu  Leu  Glu  His  Lys  Ile  Leu  Glu  Met  Glu  Gly  Lys  His  Lys  Glu  Glu
          195                     200                     205

Leu  Asp  Thr  Leu  Lys  Glu  Glu  Lys  Glu  Asn  Leu  Gln  Gly  Leu  Val  Thr
     210                     215                     220

Arg  Gln  Thr  Tyr  Ile  Ile  Gln  Glu  Leu  Glu  Lys  Gln  Leu  Asn  Arg  Ala
225                      230                     235                     240

Thr  Thr  Asn  Asn  Ser  Val  Leu  Gln  Lys  Gln  Gln  Leu  Glu  Leu  Met  Asp
                    245                     250                     255

Thr  Val  His  Asn  Leu  Val  Asn  Leu  Cys  Thr  Lys  Glu  Gly  Val  Leu  Leu
               260                     265                     270

Lys  Gly  Gly  Lys  Arg  Glu  Glu  Glu  Lys  Pro  Phe  Arg  Asp  Cys  Ala  Asp
          275                     280                     285
```

-continued

| Val | Tyr | Gln | Ala | Gly | Phe | Asn | Lys | Ser | Gly | Ile | Tyr | Thr | Ile | Tyr | Ile |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Asn | Asn | Met | Pro | Glu | Pro | Lys | Lys | Val | Phe | Cys | Asn | Met | Asp | Val | Asn |
| 305 |     |     |     |     | 310 |     |     |     |     | 315 |     |     |     |     | 320 |

| Gly | Gly | Gly | Trp | Thr | Val | Ile | Gln | His | Arg | Glu | Asp | Ala | Ser | Leu | Asp |
|     |     |     |     | 325 |     |     |     |     | 330 |     |     |     |     | 335 |     |

| Phe | Gln | Arg | Gly | Trp | Lys | Glu | Tyr | Lys | Met | Gly | Phe | Gly | Asn | Pro | Ser |
|     |     |     | 340 |     |     |     |     | 345 |     |     |     |     | 350 |     |     |

| Gly | Glu | Tyr | Trp | Leu | Gly | Asn | Glu | Phe | Ile | Phe | Ala | Ile | Thr | Ser | Gln |
|     |     | 355 |     |     |     |     | 360 |     |     |     |     | 365 |     |     |     |

| Arg | Gln | Tyr | Met | Leu | Arg | Ile | Glu | Leu | Met | Asp | Trp | Glu | Gly | Asn | Arg |
|     | 370 |     |     |     |     | 375 |     |     |     |     | 380 |     |     |     |     |

| Ala | Tyr | Ser | Gln | Tyr | Asp | Arg | Phe | His | Ile | Gly | Asn | Glu | Lys | Gln | Asn |
| 385 |     |     |     |     | 390 |     |     |     |     | 395 |     |     |     |     | 400 |

| Tyr | Arg | Leu | Tyr | Leu | Lys | Gly | His | Thr | Gly | Thr | Ala | Gly | Lys | Gln | Ser |
|     |     |     |     | 405 |     |     |     |     | 410 |     |     |     |     | 415 |     |

| Ser | Leu | Ile | Leu | His | Gly | Ala | Asp | Phe | Ser | Thr | Lys | Asp | Ala | Asp | Asn |
|     |     |     | 420 |     |     |     |     | 425 |     |     |     |     | 430 |     |     |

| Asp | Asn | Cys | Met | Cys | Lys | Cys | Ala | Leu | Met | Leu | Thr | Gly | Gly | Trp | Trp |
|     |     | 435 |     |     |     |     | 440 |     |     |     |     | 445 |     |     |     |

| Phe | Asp | Ala | Cys | Gly | Pro | Ser | Asn | Leu | Asn | Gly | Met | Phe | Tyr | Thr | Ala |
|     | 450 |     |     |     |     | 455 |     |     |     |     | 460 |     |     |     |     |

| Gly | Gln | Asn | His | Gly | Lys | Leu | Asn | Gly | Ile | Lys | Trp | His | Tyr | Phe | Lys |
| 465 |     |     |     |     | 470 |     |     |     |     | 475 |     |     |     |     | 480 |

| Gly | Pro | Ser | Tyr | Ser | Leu | Arg | Ser | Thr | Thr | Met | Met | Ile | Arg | Pro | Leu |
|     |     |     |     | 485 |     |     |     |     | 490 |     |     |     |     | 495 |     |

| Asp | Phe |
|-----|-----|

( 2 ) INFORMATION FOR SEQ ID NO:3:

( i ) SEQUENCE CHARACTERISTICS:
        ( A ) LENGTH: 2146 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 310..1803

( x i ) SEQUENCE DESCRIPTION: SEQ ID NO:3:

| CAGCTGACTC | AGGCAGGCTC | CATGCTGAAC | GGTCACACAG | AGAGGAAACA | ATAAATCTCA | 60 |
| GCTACTATGC | AATAAATATC | TCAAGTTTTA | ACGAAGAAAA | ACATCATTGC | AGTGAAATAA | 120 |
| AAAATTTTAA | AATTTTAGAA | CAAAGCTAAC | AAATGGCTAG | TTTTCTATGA | TTCTTCTTCA | 180 |
| AACGCTTTCT | TTGAGGGGGA | AAGAGTCAAA | CAAACAAGCA | GTTTTACCTG | AAATAAAGAA | 240 |
| CTAGTTTTAG | AGGTCAGAAG | AAAGGAGCAA | GTTTTGCGAG | AGGCACGGAA | GGAGTGTGCT | 300 |

| GGCAGTACA | ATG | ACA | GTT | TTC | CTT | TCC | TTT | GCT | TTC | CTC | GCT | GCC | ATT | 348 |
|           | Met | Thr | Val | Phe | Leu | Ser | Phe | Ala | Phe | Leu | Ala | Ala | Ile |     |
|           | 1   |     |     |     | 5   |     |     |     |     | 10  |     |     |     |     |

| CTG | ACT | CAC | ATA | GGG | TGC | AGC | AAT | CAG | CGC | CGA | AGT | CCA | GAA | AAC | AGT | 396 |
| Leu | Thr | His | Ile | Gly | Cys | Ser | Asn | Gln | Arg | Arg | Ser | Pro | Glu | Asn | Ser |     |
|     | 15  |     |     |     |     | 20  |     |     |     |     | 25  |     |     |     |     |     |

| GGG | AGA | AGA | TAT | AAC | CGG | ATT | CAA | CAT | GGG | CAA | TGT | GCC | TAC | ACT | TTC | 444 |
| Gly | Arg | Arg | Tyr | Asn | Arg | Ile | Gln | His | Gly | Gln | Cys | Ala | Tyr | Thr | Phe |     |
|     | 30  |     |     |     | 35  |     |     |     |     | 40  |     |     |     |     | 45  |     |

```
ATT CTT CCA GAA CAC GAT GGC AAC TGT CGT GAG AGT ACG ACA GAC CAG       492
Ile Leu Pro Glu His Asp Gly Asn Cys Arg Glu Ser Thr Thr Asp Gln
                50              55                      60

TAC AAC ACA AAC GCT CTG CAG AGA GAT GCT CCA CAC GTG GAA CCG GAT       540
Tyr Asn Thr Asn Ala Leu Gln Arg Asp Ala Pro His Val Glu Pro Asp
            65              70                      75

TTC TCT TCC CAG AAA CTT CAA CAT CTG GAA CAT GTG ATG GAA AAT TAT       588
Phe Ser Ser Gln Lys Leu Gln His Leu Glu His Val Met Glu Asn Tyr
        80              85                      90

ACT CAG TGG CTG CAA AAA CTT GAG AAT TAC ATT GTG GAA AAC ATG AAG       636
Thr Gln Trp Leu Gln Lys Leu Glu Asn Tyr Ile Val Glu Asn Met Lys
    95              100                     105

TCG GAG ATG GCC CAG ATA CAG CAG AAT GCA GTT CAG AAC CAC ACG GCT       684
Ser Glu Met Ala Gln Ile Gln Gln Asn Ala Val Gln Asn His Thr Ala
110             115                     120                 125

ACC ATG CTG GAG ATA GGA ACC AGC CTC CTC TCT CAG ACT GCA GAG CAG       732
Thr Met Leu Glu Ile Gly Thr Ser Leu Leu Ser Gln Thr Ala Glu Gln
                130                     135                 140

ACC AGA AAG CTG ACA GAT GTT GAG ACC CAG GTA CTA AAT CAA ACT TCT       780
Thr Arg Lys Leu Thr Asp Val Glu Thr Gln Val Leu Asn Gln Thr Ser
            145                     150                 155

CGA CTT GAG ATA CAG CTG CTG GAG AAT TCA TTA TCC ACC TAC AAG CTA       828
Arg Leu Glu Ile Gln Leu Leu Glu Asn Ser Leu Ser Thr Tyr Lys Leu
        160                     165                 170

GAG AAG CAA CTT CTT CAA CAG ACA AAT GAA ATC TTG AAG ATC CAT GAA       876
Glu Lys Gln Leu Leu Gln Gln Thr Asn Glu Ile Leu Lys Ile His Glu
    175                     180                 185

AAA AAC AGT TTA TTA GAA CAT AAA ATC TTA GAA ATG GAA GGA AAA CAC       924
Lys Asn Ser Leu Leu Glu His Lys Ile Leu Glu Met Glu Gly Lys His
190                     195                 200                 205

AAG GAA GAG TTG GAC ACC TTA AAG GAA GAG AAA GAG AAC CTT CAA GGC       972
Lys Glu Glu Leu Asp Thr Leu Lys Glu Glu Lys Glu Asn Leu Gln Gly
                210                     215                 220

TTG GTT ACT CGT CAA ACA TAT ATA ATC CAG GAG CTG GAA AAG CAA TTA      1020
Leu Val Thr Arg Gln Thr Tyr Ile Ile Gln Glu Leu Glu Lys Gln Leu
            225                     230                 235

AAC AGA GCT ACC ACC AAC AAC AGT GTC CTT CAG AAG CAG CAA CTG GAG      1068
Asn Arg Ala Thr Thr Asn Asn Ser Val Leu Gln Lys Gln Gln Leu Glu
        240                     245                 250

CTG ATG GAC ACA GTC CAC AAC CTT GTC AAT CTT TGC ACT AAA GAA GTT      1116
Leu Met Asp Thr Val His Asn Leu Val Asn Leu Cys Thr Lys Glu Val
    255                     260                 265

TTA CTA AAG GGA GGA AAA AGA GAG GAA GAC AAA CCA TTT AGA GAC TGT      1164
Leu Leu Lys Gly Gly Lys Arg Glu Glu Asp Lys Pro Phe Arg Asp Cys
270                     275                 280                 285

GCA GAT GTA TAT CAA GCT GGT TTT AAT AAA AGT GGA ATC TAC ACT ATT      1212
Ala Asp Val Tyr Gln Ala Gly Phe Asn Lys Ser Gly Ile Tyr Thr Ile
                290                     295                 300

TAT ATT AAT AAT ATG CCA GAA CCC AAA AAG GTG TTT TGC AAT ATG GAT      1260
Tyr Ile Asn Asn Met Pro Glu Pro Lys Lys Val Phe Cys Asn Met Asp
            305                     310                 315

GTC AAT GGG GGA GGT TGG ACT GTA ATA CAA CAT CGT GAA GAT GGA AGT      1308
Val Asn Gly Gly Gly Trp Thr Val Ile Gln His Arg Glu Asp Gly Ser
        320                     325                 330

CTA GAT TTC CAA AGA GGC TGG AAG GAA TAT AAA ATG GGT TTT GGA AAT      1356
Leu Asp Phe Gln Arg Gly Trp Lys Glu Tyr Lys Met Gly Phe Gly Asn
    335                     340                 345

CCC TCC GGT GAA TAT TGG CTG GGG AAT GAG TTT ATT TTT GCC ATT ACC      1404
Pro Ser Gly Glu Tyr Trp Leu Gly Asn Glu Phe Ile Phe Ala Ile Thr
350                     355                 360                 365
```

| | | | | | | | | | | | | | | | | |
|---|---|---|---|---|---|---|---|---|---|---|---|---|---|---|---|---|
| AGT | CAG | AGG | CAG | TAC | ATG | CTA | AGA | ATT | GAG | TTA | ATG | GAC | TGG | GAA | GGG | 1452 |
| Ser | Gln | Arg | Gln | Tyr 370 | Met | Leu | Arg | Ile | Glu 375 | Leu | Met | Asp | Trp | Glu 380 | Gly | |
| AAC | CGA | GCC | TAT | TCA | CAG | TAT | GAC | AGA | TTC | CAC | ATA | GGA | AAT | GAA | AAG | 1500 |
| Asn | Arg | Ala | Tyr 385 | Ser | Gln | Tyr | Asp | Arg 390 | Phe | His | Ile | Gly | Asn 395 | Glu | Lys | |
| CAA | AAC | TAT | AGG | TTG | TAT | TTA | AAA | GGT | CAC | ACT | GGG | ACA | GCA | GGA | AAA | 1548 |
| Gln | Asn | Tyr 400 | Arg | Leu | Tyr | Leu | Lys 405 | Gly | His | Thr | Gly | Thr 410 | Ala | Gly | Lys | |
| CAG | AGC | AGC | CTG | ATC | TTA | CAC | GGT | GCT | GAT | TTC | AGC | ACT | AAA | GAT | GCT | 1596 |
| Gln | Ser | Ser 415 | Leu | Ile | Leu | His 420 | Gly | Ala | Asp | Phe | Ser 425 | Thr | Lys | Asp | Ala | |
| GAT | AAT | GAC | AAC | TGT | ATG | TGC | AAA | TGT | GCC | CTC | ATG | TTA | ACA | GGA | GGA | 1644 |
| Asp 430 | Asn | Asp | Asn | Cys | Met 435 | Cys | Lys | Cys | Ala | Leu 440 | Met | Leu | Thr | Gly | Gly 445 | |
| TGG | TGG | TTT | GAT | GCT | TGT | GGC | CCC | TCC | AAT | CTA | AAT | GGA | ATG | TTC | TAT | 1692 |
| Trp | Trp | Phe | Asp | Ala 450 | Cys | Gly | Pro | Ser | Asn 455 | Leu | Asn | Gly | Met | Phe 460 | Tyr | |
| ACT | GCG | GGA | CAA | AAC | CAT | GGA | AAA | CTG | AAT | GGG | ATA | AAG | TGG | CAC | TAC | 1740 |
| Thr | Ala | Gly | Gln | Asn 465 | His | Gly | Lys | Leu | Asn 470 | Gly | Ile | Lys | Trp | His 475 | Tyr | |
| TTC | AAA | GGG | CCC | AGT | TAC | TCC | TTA | CGT | TCC | ACA | ACT | ATG | ATG | ATT | CGA | 1788 |
| Phe | Lys | Gly 480 | Pro | Ser | Tyr | Ser | Leu 485 | Arg | Ser | Thr | Thr | Met 490 | Met | Ile | Arg | |
| CCT | TTA | GAT | TTT | TGA | AAGCGCAATG | TCAGAAGCGA | TTATGAAAGC | AACAAAGAAA | | | | | | | | 1843 |
| Pro | Leu | Asp 495 | Phe | * | | | | | | | | | | | | |

| | | |
|---|---|---|
| TCCGGAGAAG CTGCCAGGTG AGAAACTGTT TGAAAACTTC AGAAGCAAAC AATATTGTCT | | 1903 |
| CCCTTCCAGC AATAAGTGGT AGTTATGTGA AGTCACCAAG GTTCTTGACC GTGAATCTGG | | 1963 |
| AGCCGTTTGA GTTCACAAGA GTCTCTACTT GGGGTGACAG TGCTCACGTG GCTCGACTAT | | 2023 |
| AGAAAACTCC ACTGACTGTC GGGCTTTAAA AAGGGAAGAA ACTGCTGAGC TTGCTGTGCT | | 2083 |
| TCAAACTACT ACTGGACCTT ATTTTGGAAC TATGGTAGCC AGATGATAAA TATGGTTAAT | | 2143 |
| TTC | | 2146 |

(2) INFORMATION FOR SEQ ID NO:4:

(i) SEQUENCE CHARACTERISTICS:
        (A) LENGTH: 497 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met 1 | Thr | Val | Phe | Leu 5 | Ser | Phe | Ala | Phe | Leu 10 | Ala | Ala | Ile | Leu | Thr His 15 |
| Ile | Gly | Cys | Ser 20 | Asn | Gln | Arg | Arg | Ser 25 | Pro | Glu | Asn | Ser | Gly 30 | Arg Arg |
| Tyr | Asn | Arg 35 | Ile | Gln | His | Gly | Gln 40 | Cys | Ala | Tyr | Thr | Phe 45 | Ile | Leu Pro |
| Glu | His 50 | Asp | Gly | Asn | Cys | Arg 55 | Glu | Ser | Thr | Thr | Asp 60 | Gln | Tyr | Asn Thr |
| Asn 65 | Ala | Leu | Gln | Arg | Asp 70 | Ala | Pro | His | Val | Glu 75 | Pro | Asp | Phe | Ser Ser 80 |
| Gln | Lys | Leu | Gln | His 85 | Leu | Glu | His | Val | Met 90 | Glu | Asn | Tyr | Thr | Gln 95 Trp |
| Leu | Gln | Lys | Leu 100 | Glu | Asn | Tyr | Ile | Val 105 | Glu | Asn | Met | Lys | Ser 110 | Glu Met |

Ala  Gln  Ile  Gln  Gln  Asn  Ala  Val  Gln  Asn  His  Thr  Ala  Thr  Met  Leu
          115                      120                 125

Glu  Ile  Gly  Thr  Ser  Leu  Leu  Ser  Gln  Thr  Ala  Glu  Gln  Thr  Arg  Lys
          130                      135                 140

Leu  Thr  Asp  Val  Glu  Thr  Gln  Val  Leu  Asn  Gln  Thr  Ser  Arg  Leu  Glu
145                      150                      155                      160

Ile  Gln  Leu  Leu  Glu  Asn  Ser  Leu  Ser  Thr  Tyr  Lys  Leu  Glu  Lys  Gln
               165                      170                      175

Leu  Leu  Gln  Gln  Thr  Asn  Glu  Ile  Leu  Lys  Ile  His  Glu  Lys  Asn  Ser
          180                      185                 190

Leu  Leu  Glu  His  Lys  Ile  Leu  Glu  Met  Glu  Gly  Lys  His  Lys  Glu  Glu
          195                      200                 205

Leu  Asp  Thr  Leu  Lys  Glu  Glu  Lys  Glu  Asn  Leu  Gln  Gly  Leu  Val  Thr
     210                      215                 220

Arg  Gln  Thr  Tyr  Ile  Ile  Gln  Glu  Leu  Glu  Lys  Gln  Leu  Asn  Arg  Ala
225                           230                 235                      240

Thr  Thr  Asn  Asn  Ser  Val  Leu  Gln  Lys  Gln  Gln  Leu  Glu  Leu  Met  Asp
                    245                      250                      255

Thr  Val  His  Asn  Leu  Val  Asn  Leu  Cys  Thr  Lys  Glu  Val  Leu  Leu  Lys
               260                      265                      270

Gly  Gly  Lys  Arg  Glu  Glu  Asp  Lys  Pro  Phe  Arg  Asp  Cys  Ala  Asp  Val
          275                      280                 285

Tyr  Gln  Ala  Gly  Phe  Asn  Lys  Ser  Gly  Ile  Tyr  Thr  Ile  Tyr  Ile  Asn
     290                      295                 300

Asn  Met  Pro  Glu  Pro  Lys  Lys  Val  Phe  Cys  Asn  Met  Asp  Val  Asn  Gly
305                      310                 315                           320

Gly  Gly  Trp  Thr  Val  Ile  Gln  His  Arg  Glu  Asp  Gly  Ser  Leu  Asp  Phe
               325                      330                      335

Gln  Arg  Gly  Trp  Lys  Glu  Tyr  Lys  Met  Gly  Phe  Gly  Asn  Pro  Ser  Gly
               340                      345                 350

Glu  Tyr  Trp  Leu  Gly  Asn  Glu  Phe  Ile  Phe  Ala  Ile  Thr  Ser  Gln  Arg
          355                      360                 365

Gln  Tyr  Met  Leu  Arg  Ile  Glu  Leu  Met  Asp  Trp  Glu  Gly  Asn  Arg  Ala
     370                      375                 380

Tyr  Ser  Gln  Tyr  Asp  Arg  Phe  His  Ile  Gly  Asn  Glu  Lys  Gln  Asn  Tyr
385                      390                 395                           400

Arg  Leu  Tyr  Leu  Lys  Gly  His  Thr  Gly  Thr  Ala  Gly  Lys  Gln  Ser  Ser
               405                      410                 415

Leu  Ile  Leu  His  Gly  Ala  Asp  Phe  Ser  Thr  Lys  Asp  Ala  Asp  Asn  Asp
               420                      425                 430

Asn  Cys  Met  Cys  Lys  Cys  Ala  Leu  Met  Leu  Thr  Gly  Gly  Trp  Trp  Phe
          435                      440                 445

Asp  Ala  Cys  Gly  Pro  Ser  Asn  Leu  Asn  Gly  Met  Phe  Tyr  Thr  Ala  Gly
     450                      455                 460

Gln  Asn  His  Gly  Lys  Leu  Asn  Gly  Ile  Lys  Trp  His  Tyr  Phe  Lys  Gly
465                      470                 475                           480

Pro  Ser  Tyr  Ser  Leu  Arg  Ser  Thr  Thr  Met  Met  Ile  Arg  Pro  Leu  Asp
               485                      490                      495

Phe ( 2 ) INFORMATION FOR SEQ ID NO:5:

( i ) SEQUENCE CHARACTERISTICS:
    ( A ) LENGTH: 2282 base pairs ( B ) TYPE: nucleic acid
( C ) STRANDEDNESS: double
( D ) TOPOLOGY: unknown ( i i ) MOLECULE TYPE: DNA (genomic)

( i x ) FEATURE:
( A ) NAME/KEY: CDS
( B ) LOCATION: 357..1847

( x i ) SEQUENCE DESCRIPTION: SEQ ID NO:5:

```
GAATTCCTGG  GTTGGTGTTT  ATCTCCTCCC  AGCCTTGAGG  GAGGGAACAA  CACTGTAGGA        60

TCTGGGGAGA  GAGGAACAAA  GGACCGTGAA  AGCTGCTCTG  TAAAAGCTGA  CACAGCCCTC       120

CCAAGTGAGC  AGGACTGTTC  TTCCCACTGC  AATCTGACAG  TTTACTGCAT  GCCTGGAGAG       180

AACACAGCAG  TAAAAACCAG  GTTTGCTACT  GGAAAAAGAG  GAAAGAGAAG  ACTTTCATTG       240

ACGGACCCAG  CCATGGCAGC  GTAGCAGCCC  TGCGTTTCAG  ACGGCAGCAG  CTCGGGACTC       300

TGGACGTGTG  TTTGCCCTCA  AGTTTGCTAA  GCTGCTGGTT  TATTACTGAA  GAAAGA          356
```

| | | | | | | | | | | | | | | | | |
|---|---|---|---|---|---|---|---|---|---|---|---|---|---|---|---|---|
| ATG | TGG | CAG | ATT | GTT | TTC | TTT | ACT | CTG | AGC | TGT | GAT | CTT | GTC | TTG | GCC | 404 |
| Met | Trp | Gln | Ile | Val | Phe | Phe | Thr | Leu | Ser | Cys | Asp | Leu | Val | Leu | Ala | |
| 1 | | | | 5 | | | | | 10 | | | | | 15 | | |

| GCA | GCC | TAT | AAC | AAC | TTT | CGG | AAG | AGC | ATG | GAC | AGC | ATA | GGA | AAG | AAG | 452 |
|---|---|---|---|---|---|---|---|---|---|---|---|---|---|---|---|---|
| Ala | Ala | Tyr | Asn | Asn | Phe | Arg | Lys | Ser | Met | Asp | Ser | Ile | Gly | Lys | Lys | |
| | | | 20 | | | | | 25 | | | | | 30 | | | |

| CAA | TAT | CAG | GTC | CAG | CAT | GGG | TCC | TGC | AGC | TAC | ACT | TTC | CTC | CTG | CCA | 500 |
|---|---|---|---|---|---|---|---|---|---|---|---|---|---|---|---|---|
| Gln | Tyr | Gln | Val | Gln | His | Gly | Ser | Cys | Ser | Tyr | Thr | Phe | Leu | Leu | Pro | |
| | | 35 | | | | | 40 | | | | | 45 | | | | |

| GAG | ATG | GAC | AAC | TGC | CGC | TCT | TCC | TCC | AGC | CCC | TAC | GTG | TCC | AAT | GCT | 548 |
|---|---|---|---|---|---|---|---|---|---|---|---|---|---|---|---|---|
| Glu | Met | Asp | Asn | Cys | Arg | Ser | Ser | Ser | Ser | Pro | Tyr | Val | Ser | Asn | Ala | |
| | 50 | | | | | 55 | | | | | 60 | | | | | |

| GTG | CAG | AGG | GAC | GCG | CCG | CTC | GAA | TAC | GAT | GAC | TCG | GTG | CAG | AGG | CTG | 596 |
|---|---|---|---|---|---|---|---|---|---|---|---|---|---|---|---|---|
| Val | Gln | Arg | Asp | Ala | Pro | Leu | Glu | Tyr | Asp | Asp | Ser | Val | Gln | Arg | Leu | |
| 65 | | | | | 70 | | | | | 75 | | | | | 80 | |

| CAA | GTG | CTG | GAG | AAC | ATC | ATG | GAA | AAC | AAC | ACT | CAG | TGG | CTA | ATG | AAG | 644 |
|---|---|---|---|---|---|---|---|---|---|---|---|---|---|---|---|---|
| Gln | Val | Leu | Glu | Asn | Ile | Met | Glu | Asn | Asn | Thr | Gln | Trp | Leu | Met | Lys | |
| | | | | 85 | | | | | 90 | | | | | 95 | | |

| CTT | GAG | AAT | TAT | ATC | CAG | GAC | AAC | ATG | AAG | AAA | GAA | ATG | GTA | GAG | ATA | 692 |
|---|---|---|---|---|---|---|---|---|---|---|---|---|---|---|---|---|
| Leu | Glu | Asn | Tyr | Ile | Gln | Asp | Asn | Met | Lys | Lys | Glu | Met | Val | Glu | Ile | |
| | | | 100 | | | | | 105 | | | | | 110 | | | |

| CAG | CAG | AAT | GCA | GTA | CAG | AAC | CAG | ACG | GCT | GTG | ATG | ATA | GAA | ATA | GGG | 740 |
|---|---|---|---|---|---|---|---|---|---|---|---|---|---|---|---|---|
| Gln | Gln | Asn | Ala | Val | Gln | Asn | Gln | Thr | Ala | Val | Met | Ile | Glu | Ile | Gly | |
| | | 115 | | | | | 120 | | | | | 125 | | | | |

| ACA | AAC | CTG | TTG | AAC | CAA | ACA | GCT | GAG | CAA | ACG | CGG | AAG | TTA | ACT | GAT | 788 |
|---|---|---|---|---|---|---|---|---|---|---|---|---|---|---|---|---|
| Thr | Asn | Leu | Leu | Asn | Gln | Thr | Ala | Glu | Gln | Thr | Arg | Lys | Leu | Thr | Asp | |
| | 130 | | | | | 135 | | | | | 140 | | | | | |

| GTG | GAA | GCC | CAA | GTA | TTA | AAT | CAG | ACC | ACG | AGA | CTT | GAA | CTT | CAG | CTC | 836 |
|---|---|---|---|---|---|---|---|---|---|---|---|---|---|---|---|---|
| Val | Glu | Ala | Gln | Val | Leu | Asn | Gln | Thr | Thr | Arg | Leu | Glu | Leu | Gln | Leu | |
| 145 | | | | | 150 | | | | | 155 | | | | | 160 | |

| TTG | GAA | CAC | TCC | CTC | TCG | ACA | AAC | AAA | TTG | GAA | AAA | CAG | ATT | TTG | GAC | 884 |
|---|---|---|---|---|---|---|---|---|---|---|---|---|---|---|---|---|
| Leu | Glu | His | Ser | Leu | Ser | Thr | Asn | Lys | Leu | Glu | Lys | Gln | Ile | Leu | Asp | |
| | | | | 165 | | | | | 170 | | | | | 175 | | |

| CAG | ACC | AGT | GAA | ATA | AAC | AAA | TTG | CAA | GAT | AAG | AAC | AGT | TTC | CTA | GAA | 932 |
|---|---|---|---|---|---|---|---|---|---|---|---|---|---|---|---|---|
| Gln | Thr | Ser | Glu | Ile | Asn | Lys | Leu | Gln | Asp | Lys | Asn | Ser | Phe | Leu | Glu | |
| | | | 180 | | | | | 185 | | | | | 190 | | | |

| AAG | AAG | GTG | CTA | GCT | ATG | GAA | GAC | AAG | CAC | ATC | ATC | CAA | CTA | CAG | TCA | 980 |
|---|---|---|---|---|---|---|---|---|---|---|---|---|---|---|---|---|
| Lys | Lys | Val | Leu | Ala | Met | Glu | Asp | Lys | His | Ile | Ile | Gln | Leu | Gln | Ser | |
| | | 195 | | | | | 200 | | | | | 205 | | | | |

| ATA | AAA | GAA | GAG | AAA | GAT | CAG | CTA | CAG | GTG | TTA | GTA | TCC | AAG | CAA | AAT | 1028 |
|---|---|---|---|---|---|---|---|---|---|---|---|---|---|---|---|---|
| Ile | Lys | Glu | Glu | Lys | Asp | Gln | Leu | Gln | Val | Leu | Val | Ser | Lys | Gln | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| TCC | ATC | ATT | GAA | GAA | CTA | GAA | AAA | AAA | ATA | GTG | ACT | GCC | ACG | GTG | AAT | 1076 |
| Ser 225 | Ile | Ile | Glu | Glu | Leu 230 | Glu | Lys | Lys | Ile 235 | Val | Thr | Ala | Thr | Val | Asn 240 | |
| AAT | TCA | GTT | CTT | CAA | AAG | CAG | CAA | CAT | GAT | CTC | ATG | GAG | ACA | GTT | AAT | 1124 |
| Asn | Ser | Val | Leu | Gln 245 | Lys | Gln | Gln | His | Asp 250 | Leu | Met | Glu | Thr | Val 255 | Asn | |
| AAC | TTA | CTG | ACT | ATG | ATG | TCC | ACA | TCA | AAC | TCA | GCT | AAG | GAC | CCC | ACT | 1172 |
| Asn | Leu | Leu | Thr 260 | Met | Met | Ser | Thr | Ser 265 | Asn | Ser | Ala | Lys | Asp 270 | Pro | Thr | |
| GTT | GCT | AAA | GAA | GAA | CAA | ATC | AGC | TTC | AGA | GAC | TGT | GCT | GAA | GTA | TTC | 1220 |
| Val | Ala | Lys 275 | Glu | Glu | Gln | Ile | Ser 280 | Phe | Arg | Asp | Cys | Ala 285 | Glu | Val | Phe | |
| AAA | TCA | GGA | CAC | ACC | ACA | AAT | GGC | ATC | TAC | ACG | TTA | ACA | TTC | CCT | AAT | 1268 |
| Lys | Ser 290 | Gly | His | Thr | Thr | Asn 295 | Gly | Ile | Tyr | Thr | Leu 300 | Thr | Phe | Pro | Asn | |
| TCT | ACA | GAA | GAG | ATC | AAG | GCC | TAC | TGT | GAC | ATG | GAA | GCT | GGA | GGA | GGC | 1316 |
| Ser 305 | Thr | Glu | Glu | Ile 310 | Lys | Ala | Tyr | Cys | Asp 315 | Met | Glu | Ala | Gly | Gly 320 | Gly | |
| GGG | TGG | ACA | ATT | ATT | CAG | CGA | CGT | GAG | GAT | GGC | AGC | GTT | GAT | TTT | CAG | 1364 |
| Gly | Trp | Thr | Ile | Ile 325 | Gln | Arg | Arg | Glu | Asp 330 | Gly | Ser | Val | Asp | Phe 335 | Gln | |
| AGG | ACT | TGG | AAA | GAA | TAT | AAA | GTG | GGA | TTT | GGT | AAC | CCT | TCA | GGA | GAA | 1412 |
| Arg | Thr | Trp | Lys 340 | Glu | Tyr | Lys | Val | Gly 345 | Phe | Gly | Asn | Pro | Ser 350 | Gly | Glu | |
| TAT | TGG | CTG | GGA | AAT | GAG | TTT | GTT | TCG | CAA | CTG | ACT | AAT | CAG | CAA | CGC | 1460 |
| Tyr | Trp | Leu 355 | Gly | Asn | Glu | Phe | Val 360 | Ser | Gln | Leu | Thr | Asn 365 | Gln | Gln | Arg | |
| TAT | GTG | CTT | AAA | ATA | CAC | CTT | AAA | GAC | TGG | GAA | GGG | AAT | GAG | GCT | TAC | 1508 |
| Tyr | Val | Leu | Lys 370 | Ile | His | Leu | Lys 375 | Asp | Trp | Glu | Gly | Asn 380 | Glu | Ala | Tyr | |
| TCA | TTG | TAT | GAA | CAT | TTC | TAT | CTC | TCA | AGT | GAA | GAA | CTC | AAT | TAT | AGG | 1556 |
| Ser 385 | Leu | Tyr | Glu | His | Phe 390 | Tyr | Leu | Ser | Ser | Glu 395 | Glu | Leu | Asn | Tyr | Arg 400 | |
| ATT | CAC | CTT | AAA | GGA | CTT | ACA | GGG | ACA | GCC | GGC | AAA | ATA | AGC | AGC | ATC | 1604 |
| Ile | His | Leu | Lys | Gly 405 | Leu | Thr | Gly | Thr | Ala 410 | Gly | Lys | Ile | Ser | Ser 415 | Ile | |
| AGC | CAA | CCA | GGA | AAT | GAT | TTT | AGC | ACA | AAG | GAT | GGA | GAC | AAC | GAC | AAA | 1652 |
| Ser | Gln | Pro | Gly 420 | Asn | Asp | Phe | Ser | Thr 425 | Lys | Asp | Gly | Asp | Asn 430 | Asp | Lys | |
| TGT | ATT | TGC | AAA | TGT | TCA | CAA | ATG | CTA | ACA | GGA | GGC | TGG | TGG | TTT | GAT | 1700 |
| Cys | Ile | Cys 435 | Lys | Cys | Ser | Gln | Met 440 | Leu | Thr | Gly | Gly | Trp 445 | Trp | Phe | Asp | |
| GCA | TGT | GGT | CCT | TCC | AAC | TTG | AAC | GGA | ATG | TAC | TAT | CCA | CAG | AGG | CAG | 1748 |
| Ala | Cys 450 | Gly | Pro | Ser | Asn | Leu 455 | Asn | Gly | Met | Tyr | Tyr 460 | Pro | Gln | Arg | Gln | |
| AAC | ACA | AAT | AAG | TTC | AAC | GGC | ATT | AAA | TGG | TAC | TAC | TGG | AAA | GGC | TCA | 1796 |
| Asn | Thr | Asn | Lys 465 | Phe | Asn | Gly | Ile | Lys 470 | Trp | Tyr | Tyr | Trp | Lys 475 | Gly | Ser 480 | |
| GGC | TAT | TCG | CTC | AAG | GCC | ACA | ACC | ATG | ATG | ATC | CGA | CCA | GCA | GAT | TTC | 1844 |
| Gly | Tyr | Ser | Leu | Lys 485 | Ala | Thr | Thr | Met | Met 490 | Ile | Arg | Pro | Ala | Asp 495 | Phe | |

| | | | | | |
|---|---|---|---|---|---|
| TAA * | ACATCCCAGT | CCACCTGAGG | AACTGTCTCG | AACTATTTC | AAAGACTTAA | 1897 |
| GCCCAGTGCA | CTGAAAGTCA | CGGCTGCGCA | CTGTGTCCTC | TTCCACCACA | GAGGGCGTGT | 1957 |
| GCTCGGTGCT | GACGGGACCC | ACATGCTCCA | GATTAGAGCC | TGTAAACTTT | ATCACTTAAA | 2017 |
| CTTGCATCAC | TTAACGGACC | AAAGCAAGAC | CCTAAACATC | CATAATTGTG | ATTAGACAGA | 2077 |
| ACACCTATGC | AAAGATGAAC | CCGAGGCTGA | GAATCAGACT | GACAGTTTAC | AGACGCTGCT | 2137 |
| GTCACAACCA | AGAATGTTAT | GTGCAAGTTT | ATCAGTAAAT | AACTGGAAAA | CAGAACACTT | 2197 |

```
ATGTTATACA ATACAGATCA TCTTGGAACT GCATTCTTCT GAGCACTGTT TATACACTGT      2257

GTAAATACCC ATATGTCCTG AATTC                                            2282
```

( 2 ) INFORMATION FOR SEQ ID NO:6:

( i ) SEQUENCE CHARACTERISTICS:
        ( A ) LENGTH: 496 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Trp  Gln  Ile  Val  Phe  Phe  Thr  Leu  Ser  Cys  Asp  Leu  Val  Leu  Ala
 1                   5                        10                       15

Ala  Ala  Tyr  Asn  Asn  Phe  Arg  Lys  Ser  Met  Asp  Ser  Ile  Gly  Lys  Lys
               20                       25                       30

Gln  Tyr  Gln  Val  Gln  His  Gly  Ser  Cys  Ser  Tyr  Thr  Phe  Leu  Leu  Pro
          35                       40                       45

Glu  Met  Asp  Asn  Cys  Arg  Ser  Ser  Ser  Pro  Tyr  Val  Ser  Asn  Ala
     50                       55                       60

Val  Gln  Arg  Asp  Ala  Pro  Leu  Glu  Tyr  Asp  Ser  Val  Gln  Arg  Leu
 65                       70                       75                        80

Gln  Val  Leu  Glu  Asn  Ile  Met  Glu  Asn  Asn  Thr  Gln  Trp  Leu  Met  Lys
                    85                       90                       95

Leu  Glu  Asn  Tyr  Ile  Gln  Asp  Asn  Met  Lys  Lys  Glu  Met  Val  Glu  Ile
                    100                      105                      110

Gln  Gln  Asn  Ala  Val  Gln  Asn  Gln  Thr  Ala  Val  Met  Ile  Glu  Ile  Gly
               115                      120                      125

Thr  Asn  Leu  Leu  Asn  Gln  Thr  Ala  Glu  Gln  Thr  Arg  Lys  Leu  Thr  Asp
     130                      135                      140

Val  Glu  Ala  Gln  Val  Leu  Asn  Gln  Thr  Thr  Arg  Leu  Glu  Leu  Gln  Leu
145                      150                      155                      160

Leu  Glu  His  Ser  Leu  Ser  Thr  Asn  Lys  Leu  Glu  Lys  Gln  Ile  Leu  Asp
                    165                      170                      175

Gln  Thr  Ser  Glu  Ile  Asn  Lys  Leu  Gln  Asp  Lys  Asn  Ser  Phe  Leu  Glu
                    180                      185                      190

Lys  Lys  Val  Leu  Ala  Met  Glu  Asp  Lys  His  Ile  Ile  Gln  Leu  Gln  Ser
               195                      200                      205

Ile  Lys  Glu  Glu  Lys  Asp  Gln  Leu  Gln  Val  Leu  Val  Ser  Lys  Gln  Asn
     210                      215                      220

Ser  Ile  Ile  Glu  Glu  Leu  Glu  Lys  Lys  Ile  Val  Thr  Ala  Thr  Val  Asn
225                      230                      235                      240

Asn  Ser  Val  Leu  Gln  Lys  Gln  Gln  His  Asp  Leu  Met  Glu  Thr  Val  Asn
                    245                      250                      255

Asn  Leu  Leu  Thr  Met  Met  Ser  Thr  Ser  Asn  Ser  Ala  Lys  Asp  Pro  Thr
               260                      265                      270

Val  Ala  Lys  Glu  Glu  Gln  Ile  Ser  Phe  Arg  Asp  Cys  Ala  Glu  Val  Phe
          275                      280                      285

Lys  Ser  Gly  His  Thr  Thr  Asn  Gly  Ile  Tyr  Thr  Leu  Thr  Phe  Pro  Asn
     290                      295                      300

Ser  Thr  Glu  Glu  Ile  Lys  Ala  Tyr  Cys  Asp  Met  Glu  Ala  Gly  Gly  Gly
305                      310                      315                      320

Gly  Trp  Thr  Ile  Ile  Gln  Arg  Arg  Glu  Asp  Gly  Ser  Val  Asp  Phe  Gln
                    325                      330                      335
```

| | | | | | | | | | | | | | | |
|---|---|---|---|---|---|---|---|---|---|---|---|---|---|---|
| Arg | Thr | Trp | Lys<br>340 | Glu | Tyr | Lys | Val | Gly<br>345 | Phe | Gly | Asn | Pro | Ser<br>350 | Gly | Glu |
| Tyr | Trp | Leu | Gly<br>355 | Asn | Glu | Phe | Val<br>360 | Ser | Gln | Leu | Thr | Asn<br>365 | Gln | Gln | Arg |
| Tyr | Val<br>370 | Leu | Lys | Ile | His | Leu<br>375 | Lys | Asp | Trp | Glu | Gly<br>380 | Asn | Glu | Ala | Tyr |
| Ser | Leu | Tyr | Glu | His | Phe<br>390 | Tyr | Leu | Ser | Ser | Glu<br>395 | Glu | Leu | Asn | Tyr | Arg<br>400 |
| Ile | His | Leu | Lys | Gly<br>405 | Leu | Thr | Gly | Thr | Ala<br>410 | Gly | Lys | Ile | Ser | Ser<br>415 | Ile |
| Ser | Gln | Pro | Gly<br>420 | Asn | Asp | Phe | Ser | Thr<br>425 | Lys | Asp | Gly | Asp | Asn<br>430 | Asp | Lys |
| Cys | Ile | Cys<br>435 | Lys | Cys | Ser | Gln | Met<br>440 | Leu | Thr | Gly | Gly | Trp<br>445 | Trp | Phe | Asp |
| Ala | Cys<br>450 | Gly | Pro | Ser | Asn | Leu<br>455 | Asn | Gly | Met | Tyr | Tyr<br>460 | Pro | Gln | Arg | Gln |
| Asn<br>465 | Thr | Asn | Lys | Phe | Asn<br>470 | Gly | Ile | Lys | Trp | Tyr<br>475 | Tyr | Trp | Lys | Gly | Ser<br>480 |
| Gly | Tyr | Ser | Leu | Lys<br>485 | Ala | Thr | Thr | Met | Met<br>490 | Ile | Arg | Pro | Ala | Asp<br>495 | Phe |

( 2 ) INFORMATION FOR SEQ ID NO:7:

( i ) SEQUENCE CHARACTERISTICS:
        ( A ) LENGTH: 1849 base pairs
        ( B ) TYPE: nucleic acid
        ( C ) STRANDEDNESS: double
        ( D ) TOPOLOGY: unknown ( i i ) MOLECULE TYPE: DNA (genomic)

( i x ) FEATURE:
        ( A ) NAME/KEY: CDS
        ( B ) LOCATION: 47..1573

( x i ) SEQUENCE DESCRIPTION: SEQ ID NO:7:

```
CTGTCCTGGT ACCTGACAAG ACCACCTCAC CACCACTTGG TCTCAG ATG CTC TGC         55
                                                  Met Leu Cys
                                                   1

CAG CCA GCT ATG CTA CTA GAT GGC CTC CTC CTG CTG GCC ACC ATG GCT      103
Gln Pro Ala Met Leu Leu Asp Gly Leu Leu Leu Leu Ala Thr Met Ala
     5                  10                  15

GCA GCC CAG CAC AGA GGG CCA GAA GCC GGT GGG CAC CGC CAG ATT CAC      151
Ala Ala Gln His Arg Gly Pro Glu Ala Gly Gly His Arg Gln Ile His
 20                  25                  30                  35

CAG GTC CGG CGT GGC CAG TGC AGC TAC ACC TTT GTG GTG CCG GAG CCT      199
Gln Val Arg Arg Gly Gln Cys Ser Tyr Thr Phe Val Val Pro Glu Pro
             40                  45                  50

GAT ATC TGC CAG CTG GCG CCG ACA GCG GCG CCT GAG GCT TTG GGG GGC      247
Asp Ile Cys Gln Leu Ala Pro Thr Ala Ala Pro Glu Ala Leu Gly Gly
         55                  60                  65

TCC AAT AGC CTC CAG AGG GAC TTG CCT GCC TCG AGG CTG CAC CTA ACA      295
Ser Asn Ser Leu Gln Arg Asp Leu Pro Ala Ser Arg Leu His Leu Thr
     70                  75                  80

GAC TGG CGA GCC CAG AGG GCC CAG CGG GCC CAG CGT GTG AGC CAG CTG      343
Asp Trp Arg Ala Gln Arg Ala Gln Arg Ala Gln Arg Val Ser Gln Leu
 85                  90                  95

GAG AAG ATA CTA GAG AAT AAC ACT CAG TGG CTG CTG AAG CTG GAG CAG      391
Glu Lys Ile Leu Glu Asn Asn Thr Gln Trp Leu Leu Lys Leu Glu Gln
100                 105                 110                 115

TCC ATC AAG GTG AAC TTG AGG TCA CAC CTG GTG CAG GCC AGC AGG AC      439
```

```
         Ser  Ile  Lys  Val  Asn  Leu  Arg  Ser  His  Leu  Val  Gln  Ala  Gln  Gln  Asp
                        120                      125                     130

ACA  ATC  CAG  AAC  CAG  ACA  ACT  ACC  ATG  CTG  GCA  CTG  GGT  GCC  AAC  CTC       487
         Thr  Ile  Gln  Asn  Gln  Thr  Thr  Thr  Met  Leu  Ala  Leu  Gly  Ala  Asn  Leu
                        135                      140                     145

ATG  AAC  CAG  ACC  AAA  GCT  CAG  ACC  CAC  AAG  CTG  ACT  GCT  GTG  GAG  GCA       535
         Met  Asn  Gln  Thr  Lys  Ala  Gln  Thr  His  Lys  Leu  Thr  Ala  Val  Glu  Ala
                        150                      155                     160

CAG  GTC  CTA  AAC  CAG  ACA  TTG  CAC  ATG  AAG  ACC  CAA  ATG  CTG  GAG  AAC       583
         Gln  Val  Leu  Asn  Gln  Thr  Leu  His  Met  Lys  Thr  Gln  Met  Leu  Glu  Asn
                        165                      170                     175

TCA  CTG  TCC  ACC  AAC  AAG  CTG  GAG  CGG  CAG  ATG  CTG  ATG  CAG  AGC  CGA       631
         Ser  Leu  Ser  Thr  Asn  Lys  Leu  Glu  Arg  Gln  Met  Leu  Met  Gln  Ser  Arg
         180                 185                      190                     195

GAG  CTG  CAG  CGG  CTG  CAG  GGT  CGC  AAC  AGG  GCC  CTG  GAG  ACC  AGG  CTG       679
         Glu  Leu  Gln  Arg  Leu  Gln  Gly  Arg  Asn  Arg  Ala  Leu  Glu  Thr  Arg  Leu
                             200                      205                     210

CAG  GCA  CTG  GAA  GCA  CAA  CAT  CAG  GCC  CAG  CTT  AAC  AGC  CTC  CAA  GAG       727
         Gln  Ala  Leu  Glu  Ala  Gln  His  Gln  Ala  Gln  Leu  Asn  Ser  Leu  Gln  Glu
                        215                      220                     225

AAG  AGG  GAA  CAA  CTG  CAC  AGT  CTC  CTG  GGC  CAT  CAG  ACC  GGG  ACC  CTG       775
         Lys  Arg  Glu  Gln  Leu  His  Ser  Leu  Leu  Gly  His  Gln  Thr  Gly  Thr  Leu
                        230                      235                     240

GCT  AAC  CTG  AAG  CAC  AAT  CTG  CAC  GCT  CTC  AGC  AGC  ATT  TCC  AGC  TCC       823
         Ala  Asn  Leu  Lys  His  Asn  Leu  His  Ala  Leu  Ser  Ser  Ile  Ser  Ser  Ser
                        245                      250                     255

CTG  CAG  CAG  CAG  CAG  CAG  CAA  CTG  ACG  GAG  TTT  GTA  CAG  CGC  CTG  GTA       871
         Leu  Gln  Gln  Gln  Gln  Gln  Gln  Leu  Thr  Glu  Phe  Val  Gln  Arg  Leu  Val
         260                 265                      270                     275

CGG  ATT  GTA  GCC  CAG  GAC  CAG  CAT  CCG  GTT  TCC  TTA  AAG  ACA  CCT  AAG       919
         Arg  Ile  Val  Ala  Gln  Asp  Gln  His  Pro  Val  Ser  Leu  Lys  Thr  Pro  Lys
                             280                      285                     290

CCA  GTG  TTC  CAG  GAC  TGT  GCA  GAG  ATC  AAG  CGC  TCC  GGG  GTT  AAT  ACC       967
         Pro  Val  Phe  Gln  Asp  Cys  Ala  Glu  Ile  Lys  Arg  Ser  Gly  Val  Asn  Thr
                             295                      300                     305

AGC  GGT  GTC  TAT  ACC  ATC  TAT  GAG  ACC  AAC  ATG  ACA  AAG  CCT  CTC  AAG      1015
         Ser  Gly  Val  Tyr  Thr  Ile  Tyr  Glu  Thr  Asn  Met  Thr  Lys  Pro  Leu  Lys
                        310                      315                     320

GTG  TTC  TGT  GAC  ATG  GAG  ACT  GAT  GGA  GGT  GGC  TGG  ACC  CTC  ATC  CAG      1063
         Val  Phe  Cys  Asp  Met  Glu  Thr  Asp  Gly  Gly  Gly  Trp  Thr  Leu  Ile  Gln
         325                      330                     335

CAC  CGG  GAG  GAT  GGA  AGC  GTA  AAT  TTC  CAG  AGG  ACC  TGG  GAA  GAA  TAC      1111
         His  Arg  Glu  Asp  Gly  Ser  Val  Asn  Phe  Gln  Arg  Thr  Trp  Glu  Glu  Tyr
         340                      345                     350                     355

AAA  GAG  GGT  TTT  GGT  AAT  GTG  GCC  AGA  GAG  CAC  TGG  CTG  GGC  AAT  GAG      1159
         Lys  Glu  Gly  Phe  Gly  Asn  Val  Ala  Arg  Glu  His  Trp  Leu  Gly  Asn  Glu
                             360                      365                     370

GCT  GTG  CAC  CGC  CTC  ACC  AGC  AGA  ACG  GCC  TAC  TTG  CTA  CGC  GTG  GAA      1207
         Ala  Val  His  Arg  Leu  Thr  Ser  Arg  Thr  Ala  Tyr  Leu  Leu  Arg  Val  Glu
                        375                      380                     385

CTG  CAT  GAC  TGG  GAA  GGC  CGC  CAG  ACC  TCC  ATC  CAG  TAT  GAG  AAC  TTC      1255
         Leu  His  Asp  Trp  Glu  Gly  Arg  Gln  Thr  Ser  Ile  Gln  Tyr  Glu  Asn  Phe
                        390                      395                     400

CAG  CTG  GGC  AGC  GAG  AGG  CAG  CGG  TAC  AGC  CTC  TCT  GTG  AAT  GAC  AGC      1303
         Gln  Leu  Gly  Ser  Glu  Arg  Gln  Arg  Tyr  Ser  Leu  Ser  Val  Asn  Asp  Ser
                        405                      410                     415

AGC  AGT  TCA  GCA  GGG  CGC  AAG  AAC  AGC  CTG  GCT  CCT  CAG  GGC  ACC  AAG      1351
         Ser  Ser  Ser  Ala  Gly  Arg  Lys  Asn  Ser  Leu  Ala  Pro  Gln  Gly  Thr  Lys
         420                      425                     430                     435

TTC  AGC  ACC  AAA  GAC  ATG  GAC  AAT  GAT  AAC  TGC  ATG  TGT  AAA  TGT  GCT      1399
```

```
Phe  Ser  Thr  Lys  Asp  Met  Asp  Asn  Asp  Asn  Cys  Met  Cys  Lys  Cys  Ala
               440                 445                      450

CAG  ATG  CTG  TCT  GGA  GGG  TGG  TGG  TTT  GAT  GCC  TGT  GGC  CTC  TCC  AAC        1447
Gln  Met  Leu  Ser  Gly  Gly  Trp  Trp  Phe  Asp  Ala  Cys  Gly  Leu  Ser  Asn
               455                      460                      465

CTC  AAT  GGC  ATC  TAC  TAT  TCA  GTT  CAT  CAG  CAC  TTG  CAC  AAG  ATC  AAT        1495
Leu  Asn  Gly  Ile  Tyr  Tyr  Ser  Val  His  Gln  His  Leu  His  Lys  Ile  Asn
               470                 475                      480

GGC  ATC  CGC  TGG  CAC  TAC  TTC  CGA  GGC  CCC  AGC  TAC  TCA  CTG  CAC  GGC        1543
Gly  Ile  Arg  Trp  His  Tyr  Phe  Arg  Gly  Pro  Ser  Tyr  Ser  Leu  His  Gly
          485                      490                 495

ACA  CGC  ATG  ATG  CTG  AGG  CCA  ATG  GGT  GCC  TGACACAG   CCCTGCAGAG              1593
Thr  Arg  Met  Met  Leu  Arg  Pro  Met  Gly  Ala    *
500                      505

ACTGATGCCG  TAGGAGGATT  CTCAACCCAG  GTGACTCTGT  GCACGCTGGG  CCCTGCCCAG               1653

AAATCAGTGC  CCAGGGCTCA  TCTTGACATT  CTGGAACATC  GGAACCAGCT  TACCTTGCCC               1713

CTGAATTACA  AGAATTCACC  TGCCTCCCTG  TTGCCCTCTA  ATTGTGAAAT  GCTGGGTGC                1773

TTGAAGGCAC  CTGCCTCTGT  TGGAACCATA  CTCTTTCCCC  CTCCTGCTGC  ATGCCCGGGA               1833

ATCCCTGCCA  TGAACT                                                                   1849
```

( 2 ) INFORMATION FOR SEQ ID NO:8:

( i ) SEQUENCE CHARACTERISTICS:
    ( A ) LENGTH: 509 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met  Leu  Cys  Gln  Pro  Ala  Met  Leu  Leu  Asp  Gly  Leu  Leu  Leu  Leu  Ala
 1                   5                   10                      15

Thr  Met  Ala  Ala  Ala  Gln  His  Arg  Gly  Pro  Glu  Ala  Gly  Gly  His  Arg
               20                  25                      30

Gln  Ile  His  Gln  Val  Arg  Arg  Gly  Gln  Cys  Ser  Tyr  Thr  Phe  Val  Val
          35                  40                      45

Pro  Glu  Pro  Asp  Ile  Cys  Gln  Leu  Ala  Pro  Thr  Ala  Ala  Pro  Glu  Ala
     50                  55                      60

Leu  Gly  Gly  Ser  Asn  Ser  Leu  Gln  Arg  Asp  Leu  Pro  Ala  Ser  Arg  Leu
65                  70                       75                           80

His  Leu  Thr  Asp  Trp  Arg  Ala  Gln  Arg  Ala  Gln  Arg  Ala  Gln  Arg  Val
               85                       90                       95

Ser  Gln  Leu  Glu  Lys  Ile  Leu  Glu  Asn  Asn  Thr  Gln  Trp  Leu  Leu  Lys
               100                 105                     110

Leu  Glu  Gln  Ser  Ile  Lys  Val  Asn  Leu  Arg  Ser  His  Leu  Val  Gln  Ala
          115                     120                     125

Gln  Gln  Asp  Thr  Ile  Gln  Asn  Gln  Thr  Thr  Thr  Met  Leu  Ala  Leu  Gly
     130                      135                 140

Ala  Asn  Leu  Met  Asn  Gln  Thr  Lys  Ala  Gln  Thr  His  Lys  Leu  Thr  Ala
145                      150                     155                          160

Val  Glu  Ala  Gln  Val  Leu  Asn  Gln  Thr  Leu  His  Met  Lys  Thr  Gln  Met
               165                      170                     175

Leu  Glu  Asn  Ser  Leu  Ser  Thr  Asn  Lys  Leu  Glu  Arg  Gln  Met  Leu  Met
               180                     185                     190

Gln  Ser  Arg  Glu  Leu  Gln  Arg  Leu  Gln  Gly  Arg  Asn  Arg  Ala  Leu  Glu
          195                      200                     205
```

-continued

| | | | | | | | | | | | | | |
|---|---|---|---|---|---|---|---|---|---|---|---|---|---|
| Thr | Arg 210 | Leu | Gln | Ala | Leu | Glu 215 | Ala | Gln | His | Gln | Ala 220 | Gln | Leu | Asn | Ser |
| Leu 225 | Gln | Glu | Lys | Arg | Glu 230 | Gln | Leu | His | Ser | Leu 235 | Leu | Gly | His | Gln | Thr 240 |
| Gly | Thr | Leu | Ala | Asn 245 | Leu | Lys | His | Asn | Leu 250 | His | Ala | Leu | Ser | Ser 255 | Ile |
| Ser | Ser | Ser | Leu 260 | Gln | Gln | Gln | Gln | Gln 265 | Gln | Leu | Thr | Glu | Phe 270 | Val | Gln |
| Arg | Leu | Val 275 | Arg | Ile | Val | Ala | Gln 280 | Asp | Gln | His | Pro | Val 285 | Ser | Leu | Lys |
| Thr | Pro 290 | Lys | Pro | Val | Phe | Gln 295 | Asp | Cys | Ala | Glu | Ile 300 | Lys | Arg | Ser | Gly |
| Val 305 | Asn | Thr | Ser | Gly | Val 310 | Tyr | Thr | Ile | Tyr | Glu 315 | Thr | Asn | Met | Thr | Lys 320 |
| Pro | Leu | Lys | Val | Phe 325 | Cys | Asp | Met | Glu | Thr 330 | Asp | Gly | Gly | Gly | Trp 335 | Thr |
| Leu | Ile | Gln | His 340 | Arg | Glu | Asp | Gly | Ser 345 | Val | Asn | Phe | Gln | Arg 350 | Thr | Trp |
| Glu | Glu | Tyr 355 | Lys | Glu | Gly | Phe | Gly 360 | Asn | Val | Ala | Arg | Glu 365 | His | Trp | Leu |
| Gly | Asn 370 | Glu | Ala | Val | His | Arg 375 | Leu | Thr | Ser | Arg | Thr 380 | Ala | Tyr | Leu | Leu |
| Arg 385 | Val | Glu | Leu | His | Asp 390 | Trp | Glu | Gly | Arg | Gln 395 | Thr | Ser | Ile | Gln | Tyr 400 |
| Glu | Asn | Phe | Gln | Leu 405 | Gly | Ser | Glu | Arg | Gln 410 | Arg | Tyr | Ser | Leu | Ser 415 | Val |
| Asn | Asp | Ser | Ser 420 | Ser | Ser | Ala | Gly | Arg 425 | Lys | Asn | Ser | Leu | Ala 430 | Pro | Gln |
| Gly | Thr | Lys 435 | Phe | Ser | Thr | Lys | Asp 440 | Met | Asp | Asn | Asp | Asn 445 | Cys | Met | Cys |
| Lys | Cys 450 | Ala | Gln | Met | Leu | Ser 455 | Gly | Gly | Trp | Trp | Phe 460 | Asp | Ala | Cys | Gly |
| Leu 465 | Ser | Asn | Leu | Asn | Gly 470 | Ile | Tyr | Tyr | Ser | Val 475 | His | Gln | His | Leu | His 480 |
| Lys | Ile | Asn | Gly | Ile 485 | Arg | Trp | His | Tyr | Phe 490 | Arg | Gly | Pro | Ser | Tyr 495 | Ser |
| Leu | His | Gly | Thr 500 | Arg | Met | Met | Leu | Arg 505 | Pro | Met | Gly | Ala | | | |